US011260182B2

(12) United States Patent
Udagawa et al.

(10) Patent No.: US 11,260,182 B2
(45) Date of Patent: Mar. 1, 2022

(54) CHEMICAL LIQUID INJECTOR, METHOD FOR CONTROLLING CHEMICAL LIQUID INJECTOR, AND COMPUTER PROGRAM

(71) Applicant: Nemoto Kyorindo Co., Ltd., Tokyo (JP)

(72) Inventors: Makoto Udagawa, Tokyo (JP); Hirofumi Uchizono, Tokyo (JP); Shigeru Nemoto, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 1032 days.

(21) Appl. No.: 15/566,513

(22) PCT Filed: Apr. 14, 2016

(86) PCT No.: PCT/JP2016/062043
§ 371 (c)(1),
(2) Date: Jan. 10, 2018

(87) PCT Pub. No.: WO2016/167330
PCT Pub. Date: Oct. 20, 2016

(65) Prior Publication Data
US 2018/0140778 A1    May 24, 2018

(30) Foreign Application Priority Data

Apr. 16, 2015  (JP) ............................. JP2015-084504

(51) Int. Cl.
*A61M 5/315* (2006.01)
*A61M 5/168* (2006.01)
(Continued)

(52) U.S. Cl.
CPC .......... *A61M 5/3159* (2013.01); *A61M 5/007* (2013.01); *A61M 5/142* (2013.01);
(Continued)

(58) Field of Classification Search
CPC .... A61M 5/3159; A61M 5/007; A61M 5/142; A61M 5/145; A61M 5/168; A61M 5/172; A61M 5/20; A61M 5/31578
(Continued)

(56) References Cited

U.S. PATENT DOCUMENTS 5,662,612 A     9/1997 Niehoff
5,868,710 A  *  2/1999 Battiato ............ A61M 5/14546
                                                              604/123
(Continued)

FOREIGN PATENT DOCUMENTS

CN       102172420 A      9/2011
JP       2005270629 A    10/2005
(Continued)

OTHER PUBLICATIONS

Notification of First Office Action, CN Patent Application No. 201680034934.4, dated Dec. 18, 2019 (English translation attached).
(Continued)

*Primary Examiner* — Phillip A Gray
(74) *Attorney, Agent, or Firm* — Knobbe, Martens, Olson & Bear, LLP

(57) ABSTRACT

A chemical-liquid injector includes a piston-driving mechanism (130) that moves a piston member of a syringe containing a contrast medium, which includes an actuator and a ram member which is moved back and forth by the actuator, a control circuit (150) which is electrically connected to the actuator, and an operating knob unit (170) which includes an operating knob that is to be operated by an operator, and a rotation sensor that outputs an electric signal corresponding to a rotation of the operating knob. The control circuit is configured to generate a predetermined control signal
(Continued)

accordingly, on the basis of a signal from the rotation sensor, and the piston-driving mechanism is operated according to the control signal.

14 Claims, 46 Drawing Sheets

(51) Int. Cl.
| | | |
|---|---|---|
| *A61M 5/142* | (2006.01) | |
| *A61M 5/145* | (2006.01) | |
| *A61M 5/00* | (2006.01) | |
| *A61M 5/172* | (2006.01) | |
| *A61M 5/20* | (2006.01) | |
| *A61M 5/31* | (2006.01) | |

(52) U.S. Cl.
CPC ............ *A61M 5/145* (2013.01); *A61M 5/168* (2013.01); *A61M 5/172* (2013.01); *A61M 5/20* (2013.01); *A61M 5/31578* (2013.01); *A61M 2005/3126* (2013.01); *A61M 2205/10* (2013.01); *A61M 2205/33* (2013.01); *A61M 2205/36* (2013.01); *A61M 2205/587* (2013.01)

(58) Field of Classification Search
USPC ........................................................ 604/151
See application file for complete search history.

(56) References Cited

U.S. PATENT DOCUMENTS

| | | | |
|---|---|---|---|
| 6,004,292 A | | 12/1999 | Battiato et al. |
| 2014/0128843 A1* | | 5/2014 | Baker .................... A61M 5/24 |
| | | | 604/506 |

FOREIGN PATENT DOCUMENTS

| | | |
|---|---|---|
| JP | 5492873 B2 | 5/2014 |
| JP | 2014520617 A | 8/2014 |
| JP | 2015029839 A | 2/2015 |
| WO | WO 96/32973 A1 | 4/1996 |

OTHER PUBLICATIONS

Supplementary European Search Report in corresponding European Application No. EP 16 78 0121, dated Dec. 19, 2018.
Notice of Reasons for Refusal, Japanese Patent Application No. 2017-512585 dated Feb. 18, 2020.
European Office Action received in European Application No. 16780121.6 dated Oct. 22, 2021 in 4 pages.

* cited by examiner

705

(a)

(b)

(a)

(b)

(a)

(b)

(c)

(a)            (b)

CHEMICAL LIQUID INJECTOR, METHOD FOR CONTROLLING CHEMICAL LIQUID INJECTOR, AND COMPUTER PROGRAM

TECHNICAL FIELD

The present invention relates to a chemical-liquid injector that automatically injects a chemical liquid such as a contrast medium, a method for controlling chemical-liquid injector, and a computer program. The present invention, in particular, relates to a chemical-liquid injector which improves a displacement flexibility of an operating knob in an injection head, and furthermore, is capable of carrying out more diverse operation control of a piston-driving mechanism.

BACKGROUND ART

Currently, as medical imaging diagnosis apparatuses, apparatuses such as CT (Computed Tomography) scanners, MRI (Magnetic Resonance Imaging) apparatuses, PET (Positron Emission Tomography) apparatuses, ultrasonic diagnosis apparatuses, and angiographic imaging apparatuses have been known. While using such imaging apparatuses, a chemical liquid such as a contrast medium and a physiological saline (hereinafter, simply referred to as 'a chemical liquid') is often injected into a patient's body.

As an apparatus that automatically injects a chemical liquid, various apparatuses have hitherto been known. Although a configuration and performance of an apparatus varies depending on as to for what type of test that apparatus is to be used (in other words, depending on as to with which type of an imaging apparatus that apparatus is to be used), in general, in chemical-liquid injectors for angiography, an operating knob that is to be operated manually is provided to an injection head in many chemical-liquid injectors.

In Patent Document 1 for instance, an injection head including an operating knob mechanically connected to a driving-force transmission mechanism of a piston-driving mechanism has been disclosed. By this operating knob being manually turned a little in a predetermined direction by an operator, a rain member of the piston-driving mechanism advances, thereby making it possible to push out a small volume of a chemical liquid from a syringe. Such an operating knob, as an example, is operated for venting (extracting) air from a chemical-liquid tube.

An 'angiography' is a test in which a catheter is introduced into a blood vessel, and after positioning a distal-end of the catheter near a target portion of the blood vessel to be checked, a chemical liquid such as a contrast medium is allowed to flow into the blood vessel, and shooting is carried out by using an imaging apparatus. The blood vessel that has been contrastradiographed is projected on a display and the like, and a medical staff carries out diagnosis and treatment while observing the images. In angiography, injecting of a chemical liquid being carried out through a fine catheter, it has a characteristic that an injection pressure (infusion pressure) becomes extremely high. This point is one of the major differences between a chemical-liquid injector for angiography, and a chemical-liquid injector for CT scanning and a chemical-liquid injector for MR scanning.

PRIOR ART DOCUMENT

Patent Document

Patent Document 1: Japanese Patent No. 5586310

SUMMARY OF THE INVENTION

Problems to be Solved by the Invention

Incidentally, although it was possible to carry out the chemical-liquid injection adequately favorably even by an operating knob of the conventional injection head, the operating knob being mechanically connected to the driving-force transmission mechanism, there was a room for improvement at the following points: (i) a problem that there is a limitation to certain extent on a position at which the operating knob is disposed, and (ii) a movement of the operating knob and the driving-force transmission mechanism being interlocked all the time, a problem that there is a possibility of occurrence of a breakdown or a malfunction of the apparatus due to the operating knob being turned under unforeseen circumstances by the operator.

The present invention has been made in view of the abovementioned problematic points, and an object of the present invention is to provide a chemical-liquid injector which improves a displacement flexibility of the operating knob in an injection head, and furthermore, is capable of carrying out more diverse operation control of the piston-driving mechanism.

Means for Solving the Problems

An invention according to an aspect of the present invention for solving the abovementioned issues is as follows:
A chemical-liquid injector including
 a piston-driving mechanism that moves a piston member of a syringe containing a contrast medium, which has an actuator and a ram member which is moved back and forth by the actuator,
 a control circuit which is electrically connected to the actuator, and
 an operating knob unit which includes an operating knob that is to be operated by an operator, and a rotation sensor that outputs an electric signal corresponding to a rotation of the operating knob, wherein
 the control circuit operates the piston-driving mechanism accordingly, on the basis of the signal from the rotation sensor.
(Description of Terminology)
 'Chemical-liquid injector' refers to a chemical-liquid injector that injects a chemical liquid, and in the present specification, refers to an apparatus that injects at least a contrast medium (particularly, a contrast medium that is used in angiography). The chemical-liquid injector may inject a chemical-liquid through a catheter.

The chemical-liquid injector may include (some of or all of the following components: one or a plurality of piston-driving mechanisms, one or a plurality of control circuits (may be a control section and the like), one or a plurality of head displays and one or a plurality of displays. In a case in which the chemical-liquid injector includes an injection head and a console, (a) the injection head may be equipped with the piston-driving mechanism and the head display, and the console may be equipped with the control section and the display. (b) Both the injection head and the console may be equipped with the control section. A configuration in which a control circuit is disposed at an interior of the injection head and another control circuit is disposed in the console is an example of such configuration.

Moreover, there may be another unit (control box), and a control circuit may be provided thereto. Another unit (control box) is to be connected to the injection head and/or the console.

'Chemical liquid' refers to a contrast medium, a physiological saline, a predetermined, medicinal agent, and a mixture thereof.

'Connection' in the present specification, in a case in which predetermined equipment is connected to another equipment, may be one of a wired connection and a wireless connection.

'Electrical connection' refers to components being connected in order to carry out transmission of an electric signal in one direction or both directions, and may be one of the wired connection or the wireless connection. Moreover, in addition to the components being connected directly, a case in which components are connected indirectly via another component is also included.

Specific examples of 'contrast medium' include (i) a contrast medium with iodine concentration of 240 mg/ml (for example, viscosity 3.3 mPa·s and specific gravity 1.268 to 1.296 at 37° C.), (ii) a contrast medium with iodine concentration of 300 mg/ml (for example, viscosity 6.1 mPa·s and specific gravity 1.335 to 1.371 at 37° C.), (iii) a contrast medium with iodine concentration of 350 mg/ml (for example, viscosity 10.6 mPa·s and specific gravity 1.392 to 1.433 at 37° C.). It is also possible to use a contrast medium with iodine concentration of 370 mg/ml or more.

Specific examples of 'physiological saline' include a physiological saline in which, 20 mL of physiological saline contains 180 mg of sodium chloride (for example, viscosity 0.9595 mPa·s and specific gravity 1.004 to 1.006 at 20° C.).

Effects of the Invention

According to the present invention, it is possible to provide a chemical-liquid injector, a control method, and a computer program, which further improves a displacement flexibility of the operating knob in an injection head, and furthermore, is capable of carrying out more diverse operation control of a piston-driving mechanism.

BRIEF DESCRIPTION OF THE DRAWINGS

FIG. 32 is a diagram of a state in which the flexible substrate having the plurality of light sources disposed thereon is unfolded (another light-emission pattern);

EMBODIMENT FOR CARRYING OUT THE INVENTION

An embodiment of the present invention will be described below by referring to the accompanying diagrams. Although a specific example of a chemical-liquid injector is disclosed below, the present invention is not necessarily limited to these specific arrangements.

Figure 2A:
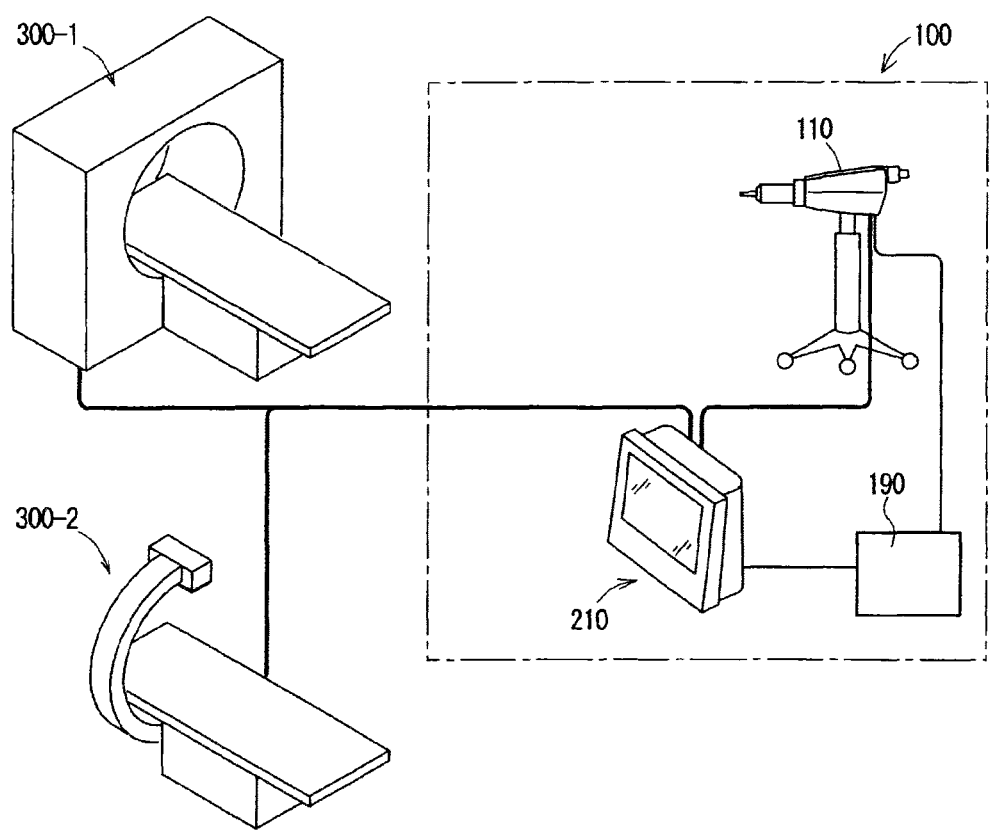
FIG. 2A is a diagram showing schematically a system in which a chemical-liquid injector and an imaging apparatus are connected.

A chemical-liquid injector 100 of the present embodiment includes an injection head 110, and a console 210 electrically connected to the injection head 110 as shown in an example in FIG. 2A. Moreover, a power-supply unit 190 which supplies an electric power by being wired, to the injection head 110 and the console 210, may be provided. Although imaging apparatuses 300-1 and 300-2 (also simply referred to as an imaging apparatus 300) are illustrated in FIG. 2A, the description thereof will be made later. The power-supply unit 190 may have a built-in control circuit. The control circuit is connected to at least one of the injection head and the console, and carries out an exchange of data in one direction or both directions.

Figure 2B:
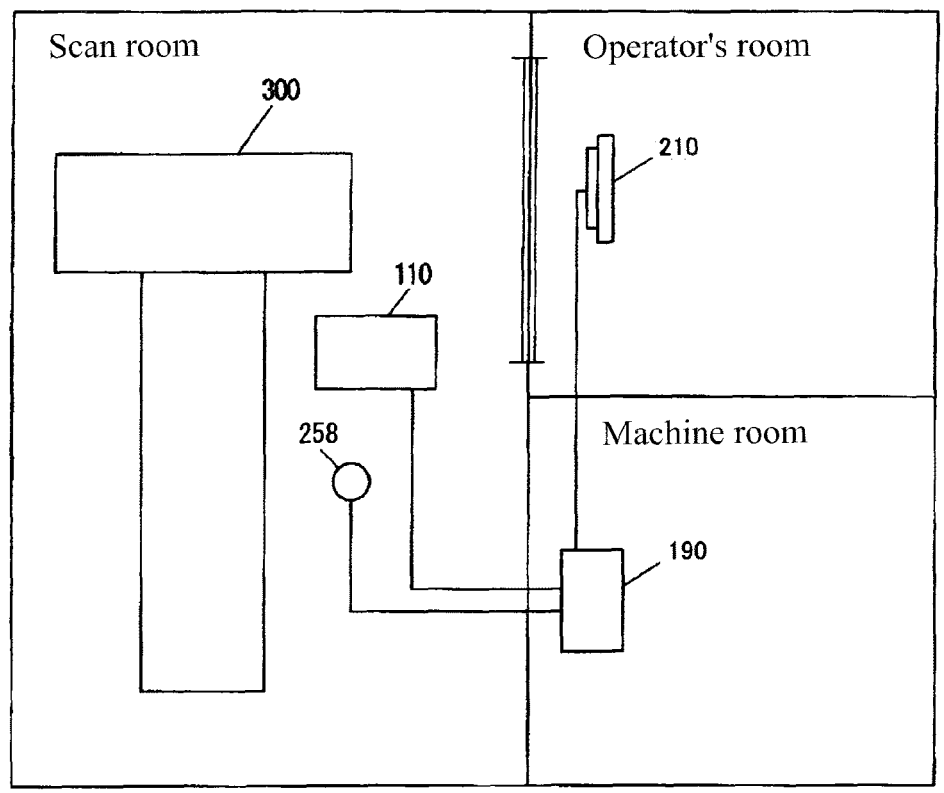
FIG. 2B is a diagram showing an example of arrangement of equipment of the chemical-liquid injector.

Although it is not limited, regarding an arrangement of these instruments, for example, as shown in FIG. 2B, the imaging apparatus 300 and the injection head 110 may be disposed in a scan room, the console 210 may be disposed in an operator's room, and the power-supply unit 190 may be disposed in a machine room. Each room may have been partitioned by walls, and a window may have been provided between the scan room and the operator's room. Regarding a position of disposing the power-supply unit 190, in another embodiment, the power-supply unit 190 may have been disposed in the operator's room. Or, the power-supply unit 190 may have been disposed in the scan room. The power-supply unit 190 may have an AC/DC convertor that supplies an electric power via a cable to each instrument upon converting an alternate current to a direct current. The power-supply unit 190 may have a storage battery (battery, not shown in the diagram). Or, the power-supply unit 190 may be a combination thereof.

An electric power-supply unit with a storage battery as an electric power supply may be integrated with the injection head 110, or may be disposed near the injection head 110. Moreover, an electric power-supply unit with a storage battery as an electric power supply may be integrated with the console 210, or may be disposed nearby. Or as a combination of these, an electric power-supply unit of a storage battery type may be provided to each of the plurality of components in the system.

As other components, a remote controller for switching an operation of the injection head may have been provided. The remote controller may have a light-emitting portion that transmits a signal. A light-receiving portion may have been provided to one or a plurality of the injection head, the console, and the electric power-supply unit. A signal from the remote controller is received, and operations such as an injection-start and injection-stop of injection head are controlled. As a matter of course, an arrangement may have been such that, apart from the injection-start and the injection-stop, other operations such as a forward-moving and a backward-moving are controlled.

As a member that holds the injection head 110, it may be a movable stand/or may be a rail stand that is to be fitted to a portion of the imaging apparatus, or may be an arm-type holder which hangs down from a ceiling. As an example of the movable stand, it may be a stand which includes a base portion 103 having a plurality of casters, a supporting column 102a extended upward from the base portion 103, and a head holding member 102b provided at an upper portion of the supporting column 102a. In this example, the head holding member 102b is pivotably arranged around a substantially vertical axis. The head holding member 102b holds the injection head 110 to be pivotable around a substantially horizontal axis.

Figure 2C:
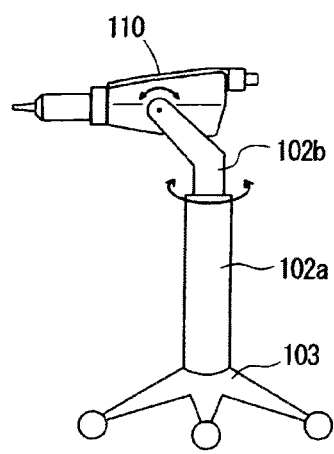
FIG. 2C is a schematic diagram showing an example of a movable stand.
Figure 2D:
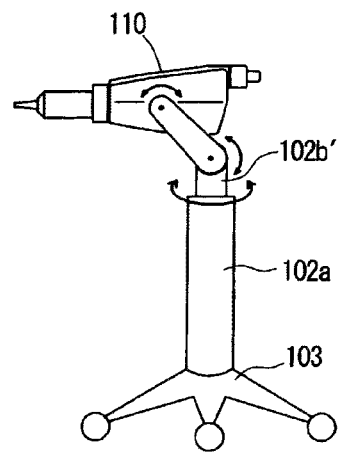
FIG. 2D is a schematic diagram showing another example of a movable stand.

In addition, the member that holds the injection head 110 may be a movable stand which includes the base portion 103, the supporting column 102a extended upward from the base portion 103, and a head holding member 102b' provided at the upper portion of the supporting column 102a as shown schematically in FIG. 2D. The head holding member 102b' has multiple joints. In other words, the head holding member 102b' includes a first member which is pivotable around a substantially vertical axis, and a second member which is pivotably connected to the first member. The second member is pivotable around a substantially horizontal axis in an example, with respect to the first member. Similarly as the head holding member 102b, the second member of the head holding member 102b' holds the injection head at a distal-end portion thereof, to be pivotable around a substantially horizontal axis. Such multiple-joint structure, in addition to being applicable to the movable stand, is also applicable to the rail stand (a rail stand of which a supporting-column lower portion it so be fitted to a portion of a medical instrument or an imaging apparatus).

As still another example, the member that holds the injection head 110 may be extended in an upward inclined direction from the upper portion of the supporting column 102a as in the head holding member 102b in FIG. 2C, but a connecting portion thereof with the supporting column 102a is not pivotable. Specifically, the holding member may include the first member extended in the upward inclined direction, connected to the supporting column 102a, and the second member which is pivotably connected (around a substantially vertical axis) to a distal-end portion of the first member. The injection head is held to be pivotable around the substantially horizontal axis, by a portion of the second member. As a further modified example, it is also possible to let the holding member to be a member having the above-mentioned arrangement, and with the first member pivotably connected to the supporting column 102a.

The chemical-liquid injector and the syringe will be described below in order.

[1. Syringe for Angiography]

Figure 3:
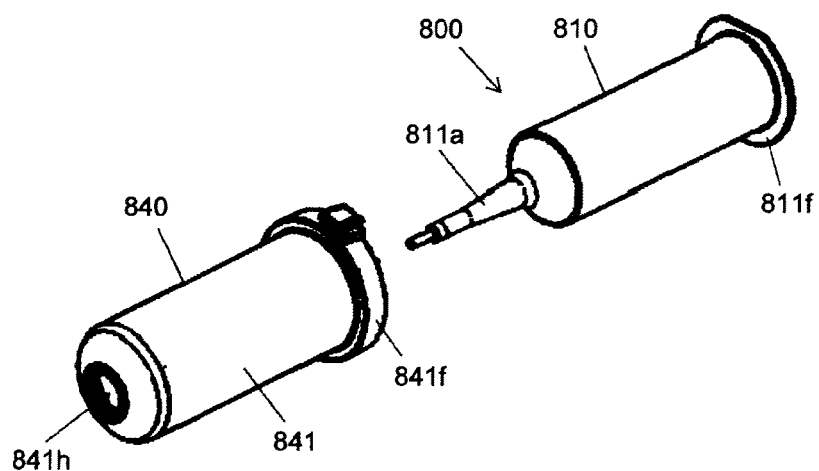
FIG. 3 is a perspective view of a protective case and a syringe.
Figure 4:
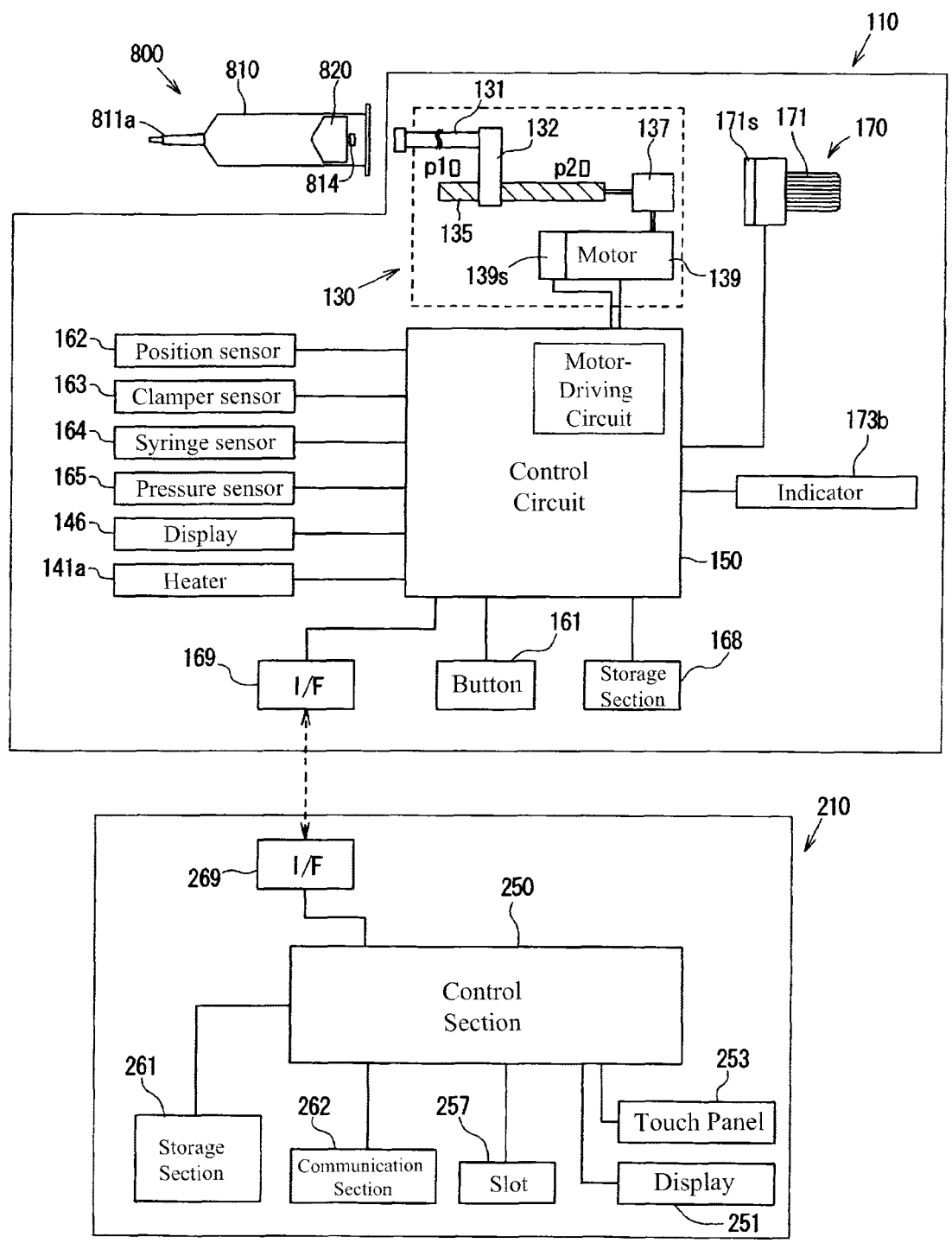
FIG. 4 is a block diagram of the chemical-liquid injector.

Regarding the syringe for angiography and a protective case thereof, as an example, heretofore known syringe and protective case can be used. Since it is necessary for describing an arrangement of the injection head, these will be described first. As shown in FIG. 3 and FIG. 4, a syringe 800 for angiography includes a cylinder member 810 in the form of a tube, and a piston member 820 slidably inserted into an interior of the cylinder member 810 (refer to FIG. 4). A volume of the cylinder 800 is not limited, and may be about 50 ml to 300 ml or about 100 ml to 200 ml for example ('a to b' implies that not less than a and not more than b). The piston member will also be referred to as a plunger (plunger member) sometimes.

A material of the cylinder member 810 may be a resin, a glass, or a metal etc. The cylinder member 810 may have a flange portion 811$f$ formed at a proximal-end portion thereof, or near the proximal-end portion thereof. A contour shape of the flange portion 811$f$ may be any shape. It may be a shape such as a circular shape, an elliptical shape, or a polygonal shape. Moreover, it may be a shape with a partially cut-off linearly at an outer peripheral portion, and specifically, a shape with a partially cut-off linearly (mutually parallel straight lines) at two locations on left and right of the outer peripheral portion.

A conduit portion (nozzle portion) 811$a$ protruded to be elongated may have been formed at a distal-end portion of the cylinder member 810. A luer-lock structure for connecting a chemical-liquid tube may have been formed at a distal-end of the conduit portion 811$a$.

The piston member 820 (refer to FIG. 4), may be a flange of so-called rod-less type. A latching protrusion 814 to which a predetermined rod (not shown in the diagram) or a ram member (details described below) of a piston-driving mechanism can be connected may have been formed on a rear surface of the piston member 820. A shape of the latching protrusion 814 may be any shape. As an example, the latching protrusion 814 may include a shaft member extended in an axial direction of the syringe, and a plate-like portion formed at an end portion of the shaft member. A material of the piston member 820 is not limited in particular, and may be a resin, a metal, or a combination of these with rubber.

Generally, a proof pressure of a product is set for the syringe 800 for angiography. The proof pressure, as an example, may be 600 psi or more, 800 psi or more, or 1000 psi or more. The syringe 800 may be a syringe to be distributed as a sterilized disposable product. The syringe 800 may be accommodated in a packaging bag as a single item or in combination with a predetermined accessary. The syringe may be of a pre-filled type having a chemical liquid (a contrast medium or a physiological saline) filled in advance, or may be of a suction type to be used upon sucking in a chemical liquid in an empty syringe.

Although it is not limited, in an embodiment of the present invention, it is preferable that the syringe for angiography has an configuration such that a certain volume of chemical liquid (4 ml or more, 5 ml or more, or 6 ml or more) remains in the conduit portion 811$a$ when the piston member 820 has been moved up to the most advanced position thereof. This is for reducing further a possibility of injecting air into the patient's body. In other words, in a configuration in which a chemical liquid does not remain at all for example, supposedly when a few cc of air is introduced into the chemical liquid, the air is pushed to an outside of the cylinder when the piston member 820 is moved up to the most advanced position (usually, injecting is carried out by directing a distal-end side of the syringe downward). In a case in which, a length of an extension tube or a catheter is adequately long, it does not pose a problem, but when the length of the extension tube or the catheter is short, there is a possibility that the air reaches the patient (patient's body). Particularly, a diameter of the catheter being fine, the volume is about 1 cc per meter, and it is envisaged that such a problem is susceptible to be apparent.

Whereas, in a case of an arrangement in which a certain volume of a chemical liquid remains as a buffer as in the abovementioned configuration, even when the piston member 820 has been pushed fully, the possibility of the air being discharged out of the syringe is reduced, and such a problem is prevented from arising.

[2. Protective Case]

The syringe 800 for angiography may be mounted on the injection head 110 in a state of being inserted into a protective case 840 as shown in FIG. 3. An example of such protective case 840 is a case which includes a main-body member 841 which is substantially circular cylindrical-shaped and hollow. The main-body member 841 has a distal-end side substantially closed, and a proximal-end side open. The syringe 800 is to be inserted through an opening at a proximal-end side of protective case 840. An opening portion 841$h$ for allowing the conduit portion 811$a$ of the syringe to pass through is formed at a distal-end surface of the main-body member 841. A flange portion 841$f$ may have been formed at a proximal-end portion of the protective case 840. It is preferable that the flange portion 841$f$ has been designed to have a shape and/or strength appropriate to be held by a holding structure (such as a clamper mechanism) on the injection-head side. The flange portion 841$f$ may have an adequate thickness (such as 2 mm or more) for securing the strength, and formed to be substantially circular ring-shaped. A material of the protective case 840 is not limited in particular, and may be a material such as a resin, a glass, and a metal.

The material of the protective case 840, specifically, may be polycarbonate. As an example, a material manufactured by Sumika Styron Polycarbonate Limited may be used. It is preferable to carry out secondary processing such as annealing treatment and/or polishing treatment, after molding. Accordingly, it is possible to facilitate improvement in the proof pressure of the protective case.

[3. Injection Head]

Figure 1A:
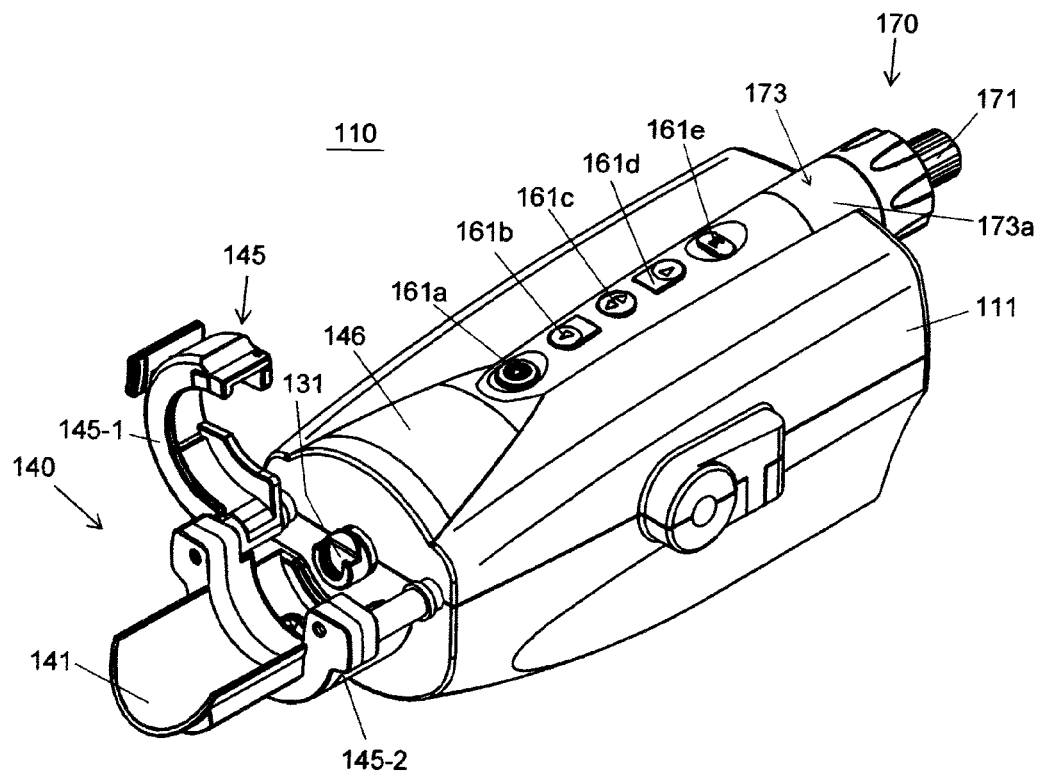
FIG. 1A is a perspective view of an injection head of the present embodiment.
Figure 1B:
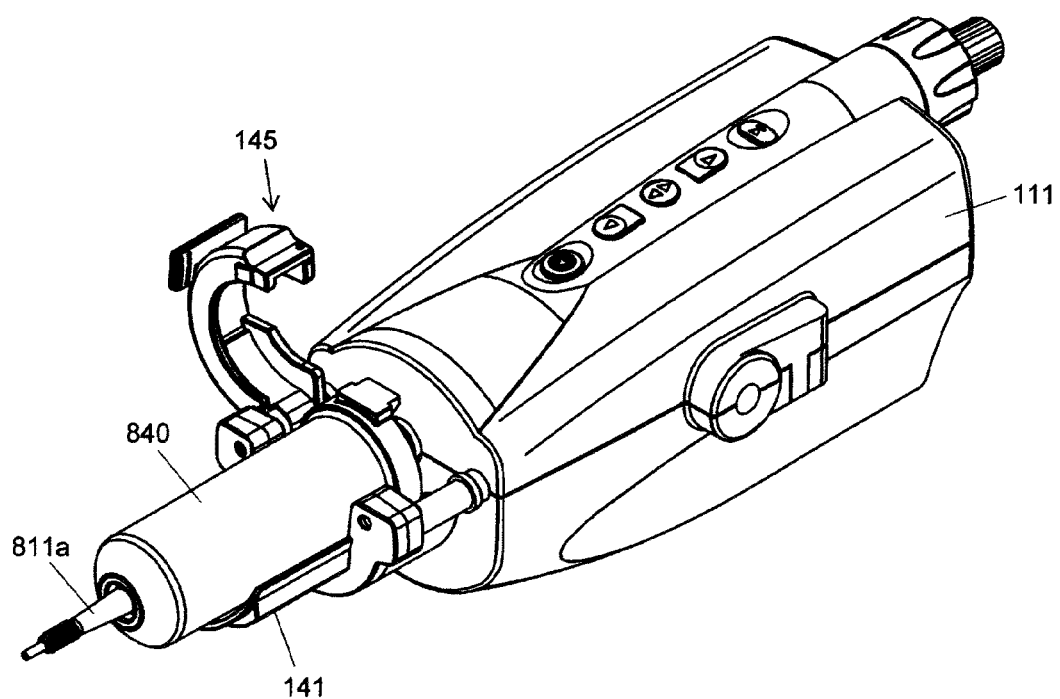
FIG. 1B is s perspective view of the injection head in a state of a syringe mounted.
Figure 1C:
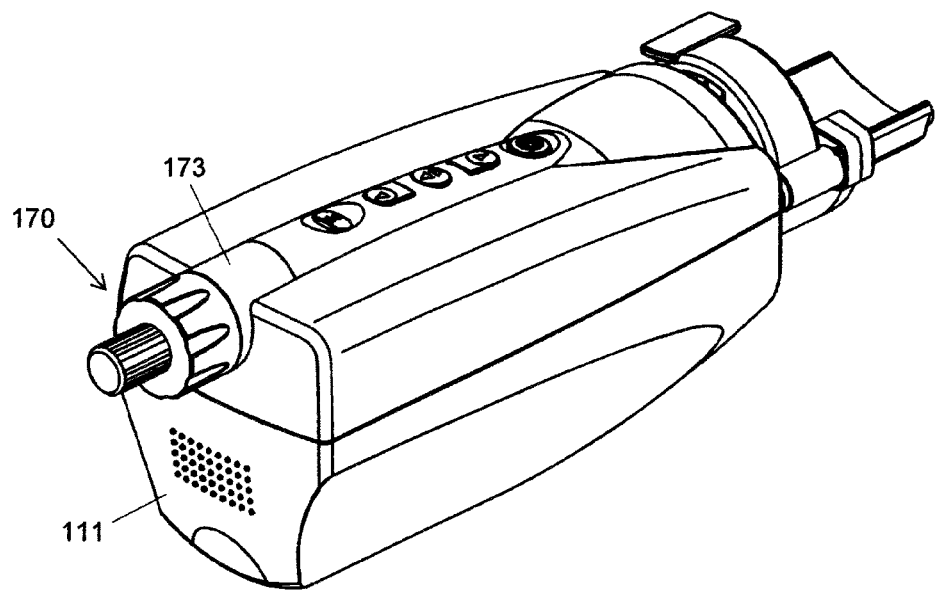
FIG. 1C is a perspective view of the injection head when viewed from a rear side.

The injection head 110, as shown in FIG. 1A to FIG. 1C, includes a housing 111, and the housing may be such that the syringe is to be mounted at a distal-end of the housing 111. The injection head 110 may be an injection head of a single type that holds a single syringe, or may be an injection head of a dual (double-cylinder type) that holds two syringes, or may be of a multiple-cylinder type that holds three or more than three syringes. Here, the injection head of the single type will be described.

The housing 111 of the head may be made of a resin. Although it is not limited, it may be a housing that is formed by combining a housing component of an upper-surface side and a housing component of a lower-surface side component. Although it is not limited, an arrangement may be such that a packing is inserted into a connecting portion of the housing component at the upper-surface side and the housing component at the lower-surface side. An operating knob unit 170 that will be described later, may be is attached to the component of the upper-surface portion. Or instead, the operating knob unit 170 may be attached directly or indirectly to a predetermined frame member (not shown in the diagram) in the housing 111. The frame member is made of a material such as a metal.

The injection head 110, as shown in FIG. 1A and FIG. 1B, may include a syringe holding portion 140 which holds the syringe 800 in a state of being accommodated in the protective case 840, a piston-driving mechanism 130 (refer to FIG. 4), and a control circuit 150 (refer to FIG. 4) which is electrically connected to the piston-driving mechanism 130.

(Syringe Holding Portion)

The syringe holding portion 140 includes a clamper 145 which is provided to a front-surface side of the housing 111 of the head, and a protective case receiver (protective case support) 141 which is provided near the clamper 145.

The clamper 145 is a holding means that holds a portion of the protective case 840. As a holding means, the clamper 145 may have any arrangement provided that it is capable of holding the protective case 840 stably. For example, the clamper 145 may be using a holding method similar to that of a clamper disclosed in Japanese Patent No. 5492873.

Specifically, in the present embodiment, the arrangement is as follows. In other words, the clamper 145 includes a pair of clamper members 145-1 and 145-2 which hold the flange portion 841f of the protective case 840. The clamper member 145-2 which is one of the pair of clamper members 145-1 and 145-2, is provided to be fixed, and the other clamper member 145-1 is provided to be openable and closable with respect to the clamper member 145-2. Each of the clamper members 145-1 and 145-2 has a substantially circular arc shaped (substantially semicircular) recess, and the flange portion 841f of the protective case 840 is to be inserted into this recess (concave portion). The clamper members 145-1 and 145-2 may be metallic members. The clamper member 145-1 has one-end portion thereof pivoted to be pivotable between an open-position at which the syringe and the protective case can be attached or detached, and a closed-position at which the syringe and the protective case are held. When the clamper member 145-1 is at the closed-position, the flange portion 841f of the protective case 840 is surrounded over the entire periphery, and is fixed. When the clamper member 145-1 is at the open-position, the flange portion 841f can be inserted into the recess by moving the protective case 840 vertically downward (it is also a direction parallel to a groove of a clamper recess).

Although not limited, an arrangement in which, when set in such manner, the latching protrusion 814 of the piston member 820 of the syringe (refer to FIG. 4) is engaged into a latching recess (a groove which is open upward) at a distal-end of a ram member 131, may be adopted.

The syringe holding portion 140 further includes a mechanism (not shown in the diagram) that holds the clamper member 145-1 at a position when the clamper member 145-1 is closed up to a predetermined closed-position. Such mechanism may use a ball plunger (not shown in the diagram) for example. When the clamper member 145-1 is at the closed-position, a ball (not shown in the diagram) of the ball plunger is resiliently engaged into a recess (not shown in the diagram) formed in a portion of the clamper member 145-1, and is in engaged state. A click feeling may be felt at the time of engagement. A ball plunger which includes a ball, a casing which holds (holds to be reciprocatably movable) the ball such that a portion of the ball protrudes, and a spring disposed inside the casing, which applies a bias in a direction of making the ball protrude from the casing, may be used.

The syringe holding portion 140 may have a clamper sensor (not shown in FIG. 1A, refer to reference numeral 163 in FIG. 4) for detecting that the clamper member 145-1 is closed up to a predetermined position. The clamper sensor may be a sensor or a switch of a contact type which makes a contact with a portion of the clamper member 145-1 when the clamper member 145-1 is closed up to the predetermined closed-position. Or, the clamper sensor may be a sensor or a switch of a non-contact type which detects optically or magnetically, the position of a portion of the clamper member 145-1 when the clamper member 145-1 is closed up to the predetermined closed-position. An optical sensor may be of a type having a light-emitting element and a light-receiving element, which detects an object on the basis of a variation in a received light signal. By such clamper sensor having been provided, the control circuit of the chemical-liquid injector is capable of detecting whether or not the clamper 145 has been closed correctly, thereby enabling even safer injecting of a chemical liquid.

(Protective Case Receiver)

The protective case receiver is positioned at a distal-end side of the clamper 145, and includes a recess which holds a portion of an outer peripheral surface of the protective case 840. It is preferable that the recess is formed to be circular arc shaped matching with an outer peripheral surface of the protective case 840. The protective case receiver 141 may be formed of a transparent or a semitransparent material. Or, the protective case 141 may be formed of an opaque material.

In the present embodiment, the protective case receiver 141 may include a holding member 141b that is formed to be circular arc shaped, and a heater 141a in the form of a flexible sheet that is fitted in a bent (curved) state on the holding member 141b. The heater 141a may be a heater for keeping a chemical liquid in the syringe warm at a predetermined temperature.

The heater 141a may be of a surface-heating type, or specifically, a heater of which a surface is heated by supplying an electric power to a conductive film. As an example, the heater 141a may be a transparent heater in which an ITO (indium tin oxide) is let to be the conductive film. Various base materials (substrates) can be used for holding an ITO film, and a film such as a PET (polyethylene terephthalate) film and a PEN (polyethylene naphthalate) film, can be used. The ITO film and a pair of electrodes are formed on such base material, and an ITO-film portion generates heat by applying a voltage between the electrodes.

Figure 5A:
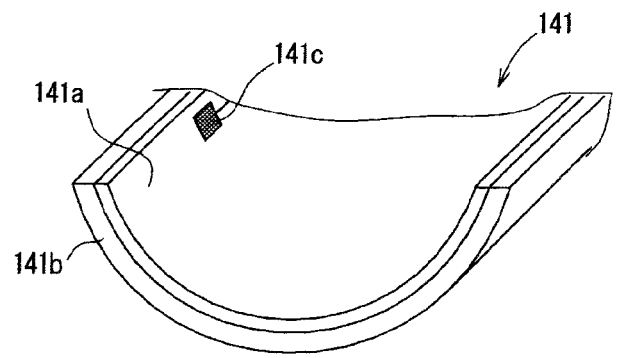
FIG. 5A is a perspective view showing schematically a structure of a protective-case receiver.

According to such heater 141a of surface-heating type, since the overall surface generates heat uniformly, it is possible to heat a chemical liquid in the syringe favorably, and moreover, since it uses a transparent heater such as ITO, as compared to using a resistance wire, it is possible to make the overall surface transparent, and to form a more transparent heater, which is a merit. A light transmittance (transmittance of white light) of the heater 141a may be 70% or more for example, and preferably 80% or more. Similarly, regarding the holding portion 141b (refer to FIG. 5A), the light transmittance thereof may be 70% or more for example, and preferably 80% or more.

In such manner, by arranging the protective case receiver 141 to have a transmittance, it becomes easy to check visually a state of an interior of the syringe 800 (the protective case also has transmittance) mounted. Accordingly, in whichever posture the injection head is, it becomes easy to verify visually whether or not an air bubble is mixed (has entered) inside the syringe. As a result of this, it is possible to prevent a chemical liquid from being injected erroneously without noticing the entry of an air bubble.

For a temperature control of the heater 141a, a thermistor 141c (refer to FIG. 5A) may have been provided to the protective case receiver 141. The thermistor 141c is electrically connected to the control circuit 150. The control circuit 150 controls the temperature of the heater 141a on the basis of a value detected by the thermistor 141c. Accordingly, it becomes easy to position (bring) a temperature of the heater 141a in a predetermined range. Without limiting to a thermistor, it is also possible to use another type of temperature sensor.

Figure 5B:
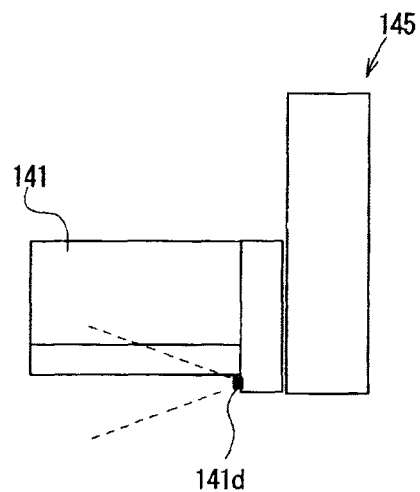
FIG. 5B is a schematic cross-sectional view showing a light-emitting device that illuminates the protective-case receiver.

In order to be able to favorably detect an air bubble inside the syringe, one or a plurality of light-emitting devices 141d (refer to FIG. 5b) that illuminate the protective case receiver 141 may be provided. The light-emitting device 141d may be disposed at a predetermined position on an opposite side of a distal-end side (left side in the diagram) of the protective case receiver 141, light may be irradiated toward the distal-end side of the protective case receiver 141. The light-emitting device 141d may be an LED (light emitting diode) etc. There may be one light-emitting device 141d, or may be disposed in plurality. The protective case receiver 141 being illuminated by a light-emitting device in such manner, the detection of an air bubble inside the syringe can be carried out more easily.

In the abovementioned configuration, although the light-emitting device is disposed to be directed to irradiate light toward the distal-end side of the protective case receiver, the light-emitting device may be disposed to be directed to irradiate light toward a central-axis side (inner side of radial direction). The plurality of light-emitting devices may be disposed along a peripheral direction of the protective case receiver. For example, an arrangement may be such that the plurality of light-emitting devices is disposed in a column near an edge on one side of the protective case receiver.

(Piston-Driving Mechanism)

The piston-driving mechanism 130, as shown in FIG. 4, includes a motor 139 as an actuator, a transmission mechanism that transmits a rotation output of the motor 139, a ball screw 135 that is rotated by the transmission mechanism 137, a ball nut unit 132, the ram member 131 which moves back and forth with the movement of the ball nut unit 132, and a frame (not shown in the diagram) which holds at least some of these components.

As the motor 139, a direct-current motor can be used, and among these, particularly, a direct-current brushless motor can be used preferably. The brushless motor, being with no brush, has a merit of low noise and superior durability. Moreover, the brushless motor being capable of rotating with a higher speed, by making small (reducing) a torque exerted to the motor by making an external gear ratio high, has a merit of being able to make small a current value necessary for injecting a chemical liquid with a desired injection pressure. Generally, a brushless motor has a sensor for detecting a position of a magnet at an interior. Therefore, an arrangement may be made to detect an amount of rotation and a speed of rotation of the motor by using an output from the sensor. Moreover, a rotation sensor 139s for detecting the amount of rotation and/or the speed of rotation of the motor may have been provided separately. Specifically, a sensor such as a rotary encoder and a resolver can be used. For injecting a contrast medium in angiography, it is preferable to use a motor with a high output such as 70 W or more, or 150 W, or 250 W or more.

The output of the motor 139 is transmitted to the ball screw 135 via the transmission mechanism 137. The transmission mechanism 137 may be of any type and, for example, may have a first pulley (not shown in the diagram) connected directly or indirectly to an output shaft of the motor 139, a second pulley (not shown in the diagram) connected directly or indirectly to the ball screw 135, and a belt (not shown in the diagram) put around the two pulleys. A gear unit or a chain transmission mechanism may be used instead of such belt transmission mechanism.

In the piston-driving mechanism 130 arranged as mentioned above, as the motor 139 rotates, the ball screw 135 also rotates by the rotation of the motor 139, and in accordance with a direction of rotation of the ball screw 135, the ball nut unit 132 and the ram member 131 connected to the ball nut unit 132 advances or retreats along the ball screw 135.

(Description of Block Diagram)

Next, each component in a block diagram in FIG. 4 will be described below while referring to other diagrams as well. The injection head 110, as shown in FIG. 4, includes the control circuit 150, a storage section 168, a physical button 161, the operating knob unit 170 as another input device, sensors 162 to 165, a display 146, a heater 141a, and an indicator 173b.

(Control Circuit)

The control circuit 150 may include a CPU (central processing unit) which carries out arithmetic processing, a memory, and an interface, and may realize various functions by executing computer programs stored in the memory. The control circuit 150 may include a processor such as a one-chip microcomputer. The control circuit 150 may have the processor mounted on a predetermined substrate, and various electric circuits (such as a motor-driving circuit) provided on the substrate. The control circuit 150 is electrically connected to various components.

The control circuit 150 may be configured (programmed) to carry out the following processing for example:
  to carry out a predetermined arithmetic processing on the basis of signals from various sensors (details described below),
  to control an operation of transmitting a predetermined motor-control signal to the piston-driving mechanism,
  to display predetermined information on the display (details described below),
  to receive an input from a user via an input unit (details described below) such as the physical button, and
  to control the operation of the heater.

(Various Sensors)

(a1) Position Sensor

The position sensor 162 is for regulating a movable range of the ram member 131. For instance, the position sensor 162 may include a first position sensor which detects that the ram member 131 has moved up to the most advanced position, and a second position sensor which detects that the ram member 131 has moved up to the most retreated position. These sensors may be of contact type or non-contact type. As the sensor of non-contact type, an optical sensor having a light-emitting element and a light-receiving element can be used. Specifically, the sensor may be a photo-interrupter in which an amount of light received by a light-receiving element decreases due to light being shielded by an object to be detected, and the detection is carried out by capturing the decrease in the amount of light received. Or, a reflecting photo-interrupter may be used. The first position sensor may have been disposed at an anterior side (refer to reference numeral p1) in a direction along a direction of movement of the ram member as shown schematically in FIG. 4, and the second position sensor may have been disposed at a posterior side (refer to reference numeral p2). In addition to this, as the position sensor, it is also possible to use sensors such as a contact sensor in which a physical contact is used, an electric sensor which detects an object electrically, a magnetic sensor, a hall sensor, or a proximity sensor.

(a2) Clamper Sensor

A clamper sensor 163 may be a sensor of contact type which is configured such that when the clamper member 145-1 is closed up to a predetermined closed-position, it makes a contact with a part thereof. Or, the clamper sensor 163 may be a sensor of non-contact type which detects optically or magnetically a position of a portion of the clamper member 145-1 when the clamper member 145-1 is closed up to a predetermined closed-position. Details are as mentioned above.

(a3) Syringe Detecting Sensor

A syringe detecting sensor 164 is used for detecting whether or not the syringe and/or the protective case have/has been mounted. Furthermore, the syringe detecting sensor 164 may be capable of making a judgment of as to what type of syringe and/or protective case have/has been mounted. Such a sensor may be of contact type or non-contact type, and it is possible to use the following sensors; a contact sensor in which a physical contact is used, an electric sensor which detects an object electrically, a magnetic sensor, a hall sensor, or a proximity sensor.

Each sensor can be used not only for detection of the syringe but also for detection of the protective cover. For instance, one or a plurality of identification members may be provided to the protective cover, and this may be detected by the sensor. It is possible to use a metal or a magnet as the identification member. Information to be identified may include at least one of a size of the protective cover (a diameter dimension and/or a length dimension. In other words, at least one information of as to with a syringe of which diameter it is compliant, and/or a syringe of what length it is compliant), and information of a chemical liquid in the syringe. Identification of information may be carried out by detecting a difference in a polarity of the magnet. There may be one magnet or a plurality of magnets. Although a position at which the identification member is to be provided is not limited in particular, it may be a flange portion of the protective case, or a surrounding thereof. Specifically, one or a plurality of identification members may have been provided to a portion protruded from the flange portion. The 'portion protruded from the flange portion' may be a substantially plate-shaped structural portion, and may have a shape jutted out by a predetermined length toward an outer side in a radial direction of the flange portion.

As a specific example, it is possible to carry out detection by using the plurality of magnets, where, in a case of both N (north) poles, it will be detected as a first type, in a case of both S (south) poles, it will be detected as a second type, in a case of one N-pole and the other S-pole, it will be detected as a third type, and in a case of one S-pole and the other N-pole, it will be detected as a fourth type. In an embodiment, it is preferable that the chemical-liquid injector is configured to set automatically the movable range of the ram member on the basis of the information read in such manner. Moreover, the chemical-liquid injector may have been configured to identify a type of the chemical liquid or a product name, or whether or not it is a pre-filled syringe.

(a4) Pressure Sensor

A pressure sensor 165 is for calculating a pressure for pushing the piston member 820 of the syringe, and accordingly, it is possible to find an estimated value of the pressure of the chemical liquid. The pressure sensor 165 may be a pressure sensor such as a load cell. The load cell is to be provided at a position where it is capable of detecting the pressure with which the ram member 131 of the piston-driving mechanism 130 pushes the piston member. In a case of finding the estimated value of the pressure of the chemical liquid at the time of injecting the chemical liquid, by using a detection result of the load cell, the calculation may be carried out upon taking into consideration a size of a needle, a concentration of the chemical liquid, and injecting conditions.

(a5) Display

One or a plurality of displays 146 for displaying predetermined information may have been provided to the injection head. In the present embodiment, one display 146 has been provided. The display 146 may be a display in which an organic EL (electro-luminescence) display has been used. Although a size of the display 146 is not limited in particular, and may be determined appropriately upon taking into consideration a size of the injection head 110, it is preferable that a vertical dimension is 10 mm or more, or 15 mm or more. It is preferable that a horizontal dimension is 20 mm or more, or 30 mm or more. Regarding the dimensions, in a case in which the dimensions are excessively small, display of the necessary information becomes difficult and a visibility is degraded, whereas in a case in which the dimensions are excessively large, there is a possibility that the size of the head becomes large.

In a case of the organic EL display, being self-emitting, a backlight such as an LCD (liquid crystal display) is not necessary, and it is advantageous for further thinning and light-weighting. Moreover, with regard to a contrast, in a case of the LCD, as it uses backlight, a brightness of an area that is supposed to be dark originally increases, whereas in a case of the organic EL display, it is possible to display the predetermined information with a high contrast as it has been. For instance, a contrast ratio of a liquid crystal display with backlight is approximately 100 or less, a contrast ratio for an OLED (organic liquid-emitting diode) may reach up to 2000:1. In the present embodiment, it is preferable that the contrast ratio for the organic EL display is 1000 or more, and 1500 or more is more preferable, and 2000 or more is even more preferable.

To use such display which enables to display with high contrast in medical equipment to be used in the scan room is preferable from the following viewpoint. In other words, the scan room in which the chemical-liquid injector of the present embodiment is to be used (particularly, an scan room in which the angiography is performed), generally a level of lighting intensity similar to that in an operating room is sought, and as an example, is let to be a bright environment having a shadow-less lamp (surgical lamp) of about 20,000 lux installed, and the lighting intensity of 750 lux to 1,500 lux for the overall operation room. The display of the injection head of the present embodiment with such high contrast is advantageous from points that it is easy to display contents of the display even in such bright scan room, and it can also contribute to reduction of occurrence of an error in medical treatment.

Figure 6:
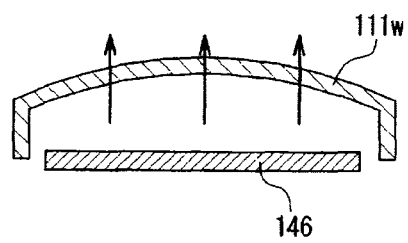
FIG. 6 is a cross-sectional view showing schematically a display on a head and a window which covers the display (state of being cut in a vertical direction along a line of section extended in a direction of width of the head)

Although the description was made by citing an example of the organic EL display, it may be of another type (such as a liquid crystal display) provided that it satisfies the above-mentioned condition of contrast ratio. Regarding a relationship of the display 146 and the housing 111 of the injection head, as shown in FIG. 6 for example, a window 111w which is colored or transparent or semitransparent may have been disposed. The window 111w may be a component made of a resin.

Although an example in which the display with a high contrast ratio has been provided integrally to the head was described above, the invention related to the display is not limited to the abovementioned example. This is because, an action and effect of such display, that it can be used appropriately in the scan room of a high lighting intensity can be achieved similarly even when the display has not been provided integrally to the head. Accordingly, there may be another sub-display separate from the injection head for example, which satisfies such condition of contrast ratio. The sub-display may be electrically connected to injection head and/or console by wire or by wireless, and may display various information (various information related to contrastradiography. Moreover, it is preferable to adopt such display which satisfies the condition of contrast ratio for other equipment disposed in the scan room, such as a stand-alone display device, a wireless communication equipment, or a device that displays an image captured of a patient.

Next, although the contents to be displayed on the display 146 are not limited in particular, it may be at least one of the following:

predetermined state-display before start of injection,
predetermined display related to a posture of the head,
predetermined display related to loading of the syringe,
predetermined display of a state during an injection operation,
display of chemical-liquid injecting conditions scheduled for injection,
display of chemical-liquid injecting condition for injection that has been carried out.

Figure 7:
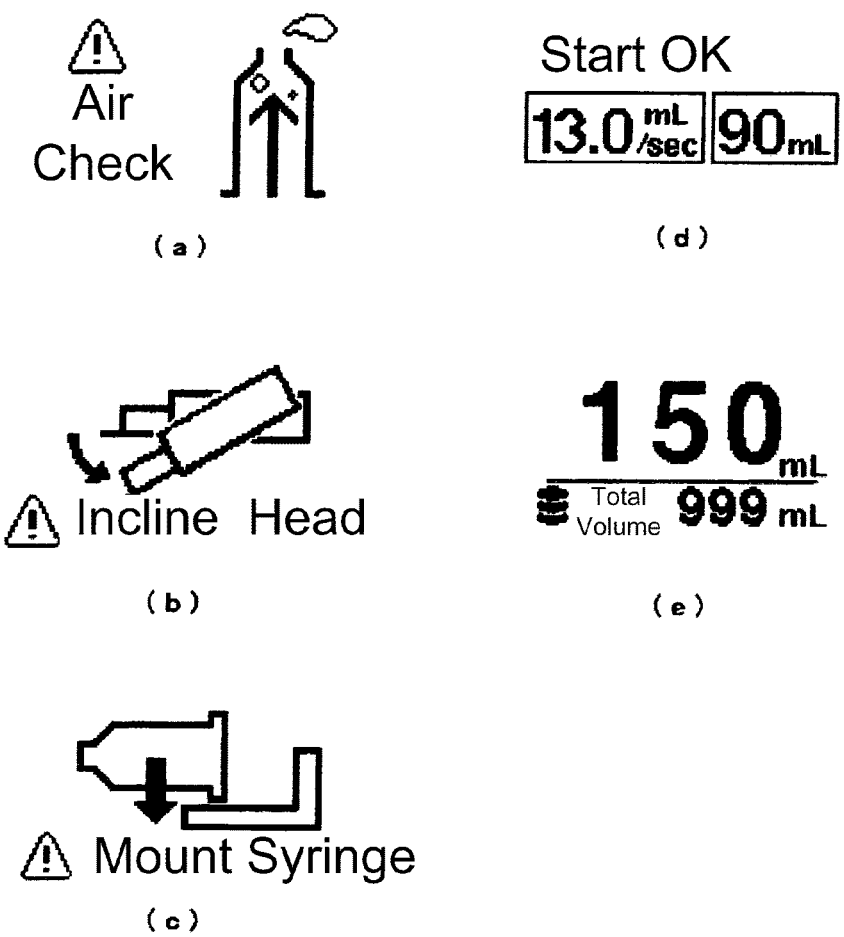
FIG. 7 is a diagram showing a number of examples of images that can be displayed on the display.

FIG. 7 shows an example of an image displayed on the display 146. FIG. 7(a) is a display of 'air check', and includes an image of a syringe and an image of an air bubble in the syringe. This is a display for helping an operator to check and eliminate the air bubble in the syringe, before the start of injection. By displaying such image, it is possible to induce check and elimination of an air bubble, and to reduce a possibility of the air bubble entering into a body of a person examined. The display in FIG. 7(a) may be after completion of setting of an injection protocol, and may be displayed automatically by an apparatus at a predetermined tinning before injecting the chemical liquid.

FIG. 7(b) is a display related to the posture of the head, and is for helping the operator to change the posture of the head. An image of the head (specifically, an image of the head in a posture in which a distal-end side of the head is directed downward and/or an image of the head in a posture in which the distal-end side of the head is directed upward) may be included in this display. Moreover, the display may include a text display indicating tilting of the head. In a case of angiography for example, a chemical liquid is sucked into an empty syringe, and thereafter, the chemical liquid is injected. Moreover, at the time of sucking the chemical liquid, the distal-end side of the head is let to be directed downward, and at the time of injecting the chemical liquid, the distal-end side of the head is let to be directed upward. Therefore, the display in FIG. 7(b) may be displayed after the completion of the suction operation, and may be displayed automatically by the apparatus (injector) at a predetermined timing before injecting the chemical liquid. In the abovementioned description, 'directed downward' refers to a posture in which the distal-end side of the syringe is at a lower side of the rear-end side of the syringe to an extent that it enables to prevent air from being accumulated at the distal-end side of the syringe, and is not necessarily limited to a posture of being directed directly below.

FIG. 7(c) is a display related to mounting of syringe, and is for helping the operator to mount the syringe. An image of the syringe may have been included in this display. Moreover, the display may include a text display indicating mounting of the syringe. The display in FIG. 7(c) may be displayed automatically by the apparatus (injector) at a predetermined timing of a state of a judgment that the syringe has not been mounted is made, from a detection result of the syringe sensor.

FIG. 7(d) is a display related to chemical-liquid injecting conditions that have been set, and includes a text display of an injecting rate (flow rate) and an injection volume to be injected. Both of the injecting rate and the volume to be injected may be displayed, or one of the two may be displayed. Moreover, the display may include a text display of 'start OK' (for example) indicating that it is possible to start injection. The display in FIG. 7(d) may be after completion of setting of the injection protocol, and may be displayed automatically by an apparatus at a predetermined timing before injecting the chemical liquid.

FIG. 7(e) is a display related to chemical-liquid injecting condition for injection that has been carried out, and includes a text display of the volume of chemical liquid injected in this example. Moreover, the display may include a text display related to a total volume of a plurality of chemical-liquid injections. The display in FIG. 7(e) may be after completion of injecting the chemical liquid, and may be displayed automatically by an apparatus (injector) at a predetermined timing.

(a6) Heater

In the injection head of the present embodiment, the transparent heater in which the ITO film has been used is provided as mentioned above.

(a7) Interface

An interface 169 is a connecting portion for exchanging information with the console 210. A connection of the console 210 and the injection head 110 may be by wire or may be wireless.

(a8) Storage Section

The storage section 168 may be any storage section provided that it is a storage medium capable of storing data, and may include a memory and a hard disc. Information (such as operation algorithm) and data tables related to a basic operation of the injection head may have been stored in the storage medium. Such information may have been stored in a memory (not shown in the diagram) in the control circuit. Moreover, such information may have been stored in a memory area (memory in a control section, storage section) in the console connected to the head.

(a9) Physical Buttons

The physical buttons are not limited in particular, and may be as follows:

advance-button for making the ram member advance,
retreat-button for making the ram member retreat, accelerator-button (speed-up button) which increases a moving speed (velocity) of the ram member by being pressed simultaneously with the advance button or the retreat button, return-button which returns the ram member up to a retreat position, stop-button which stops the operation of the head.

It is possible to dispose the physical buttons appropriately on an upper surface, a side surface, a lower surface, and a rear-end surface of the injection-head housing. In the present embodiment, as shown in FIG. 1A, a stop button 161a, an advance button 161b, an accelerator button 161c, a retreat button 161d, and a return button 161e are disposed on the upper surface of the housing.

Figure 8:
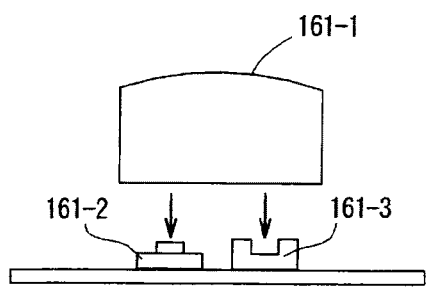
FIG. 8 is a diagram showing an example of a redundant design of a physical button.

For detecting assuredly that at least one of the physical buttons has been pressed, it is preferable to adopt a redundant design. Specifically, two or more than two devices for detecting that a key 161-1 has been pressed as shown in FIG. 8, may have been provided. For example, switches or sensors of different types may have been provided, and in the example, a switch 161-2 of contact type, and a sensor 161-3 which detects that the key 161-1 having a light-emitting element and a light-receiving element has been pressed, are provided. Specifically, it is possible to use a photo-interrupter. As another embodiment, two or more than two switches or sensors of non-contact type may be provided, or two or more than two switches or sensors of contact type may be provided. According to such configuration, even in a case in which one of the switches or sensors malfunctions, since the other one or a plurality of switches or sensors can carry out the detection, it is possible to improve further a reliability and safety of the apparatus.

(a10) Light-Emitting Portion;

The indicator 173b in FIG. 4 is an LED (light emitting diode) for example, and is for informing an operation state of the injection head to a user. Specifically, as shown in FIG. 1A, the indicator 173b may have been provided as a light source of the light-emitting portion 173 disposed adjacent to the operating knob unit 170. The light-emitting portion 173 may have any external shape, and may have a light-emitting portion cover 173a which is formed to be circular cylindrical-shaped or semicircular cylindrical-shaped as shown in FIG. 1A. The light-emitting portion cover 173a may be a member made of a transparent resin or a semitransparent resin. In a case of disposing a plurality of light sources at an interior, the plurality of light sources may have been disposed inside the same cover in a direction along a peripheral direction of the light-emitting portion cover 173a.

By changing a color of light emitted or a light-emitting pattern of the light-emitting portion 173, it is possible to inform the user various situations (states) of the injection head. Changing the light-emitting pattern of the light source in accordance with an operation of rotating (turning) the operating knob 171 will be described later. Although, an example of LED was cited as the indicator 173b, as a matter of course, a type of the light source is not limited in particular, and it is possible to adopt a light source of another type.

(a11) Operating Knob

The operating knob unit 170 is for moving the ram member back and forth manually by operating (rotating operation, turning operation) the operating knob unit. The operating knob unit 170 includes the operating knob 171 that is to be operated by the operator, and a rotation sensor 171s which is connected to the operating knob 171 (refer to FIG. 4).

The operating knob unit 170, not being a unit for transmitting physically a rotational power to the piston-driving mechanism 130, is not required to be mechanically connected to the piston-driving mechanism 130, and basically, it is reasonable to dispose at any position of the injection head 110. Regarding a position at which the operating knob unit 170 is to be disposed, in one of the embodiments, the operating knob unit 170 may be disposed at a posterior side of an intermediate position of a length in a frontward-rearward direction of the injection head (including the syringe holding portion). More preferably, the operating knob unit 170 may be disposed at a rear-end portion of the injection head.

Regarding a relationship with a direction of width of the injection head, although it is possible to dispose on a side surface of the housing 111, sometimes, to be disposed at a position at an inner side of a width of the housing 111, when viewed from a head upper surface is preferable from a point that it does not lead to an increase in the size of the apparatus (injector). In terms of a positional relationship with the piston-driving mechanism 130, to be disposed such that a central axis of the ram member 131 of the piston-driving mechanism or a line parallel to a line parallel to the same central line, and an axis of center of rotation of the operating knob are aligned, is preferable in one of the embodiments.

Figure 1D:
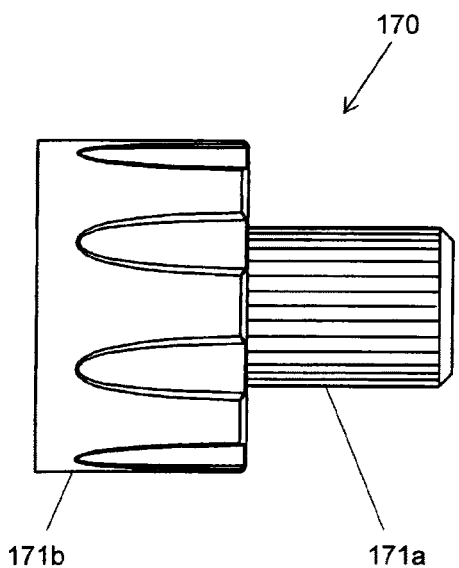
FIG. 1D is a side view of an example of an operating knob.

The operating knob 171, although not limited, may be formed to be substantially circular cylindrical shaped as a whole, and specifically, may include a circular cylindrical portion 171a having a first diameter, and a circular cylindrical portion 171b having a second diameter larger than the circular cylindrical portion 171a as shown in FIG. 1D. As a matter of course, the operating knob 171 may not be such stepped knob, and may be let to have simple substantially circular cylindrical shape. Grooves may have been formed with a predetermined pattern on one or both the circular cylindrical portions 171a and 171b in order to make it easy to turn the knob. Another example of the operating knob 171 may be an operating member which is not circular cylindrical shaped but is columnar with a rectangular or a polygonal shape, or may be an operating member such as a substantially star-shaped handle.

The rotation sensor 171s may be a rotary encoder which is capable of detecting a direction of rotation and the rotational speed (velocity) of the operating knob 171. The rotary encoder generates a pulse signal as a detection result.

Regarding a torque for rotating the operating knob 171, it is preferable to set a rotation torque to be low, and to turn the operating knob 171 lightly. As another aspect, taking into consideration that the torque for rotating a knob in a case of a conventional mechanical knob was comparatively higher, the torque may be of the same level, such as the torque with a lower limit of 0.2 (kgf·cm) or more, 0.3 (kgf·cm) or more, and 0.4 (kgf·cm) or more. The upper limit may be let to be in a range of 2.0 (kgf·cm) or less, or 1.0 (kgf·cm) or less. As a reason for adopting such configuration, in a case in which the rotation torque of the operating knob 171 is lighter than required, there would be a possibility that an operator who is used to operate the conventional mechanical knob, operates the knob erroneously, whereas in a case in which the rotation torque is excessively heavy, it is difficult to turn the knob, and there is a possibility of posing a problem in a series of treatment.

It is possible to set appropriately the rotation torque by using a clamper component such as a slipping clutch that carries out an adjustment of torque by using a frictional force between the members, or a rotary damper that carries out an adjustment of torque by using a viscous property of oil. Such damper component is to be connected directly or indirectly to the operating knob 171. As the slipping clutch, 'MINI-KEEPER' manufactured by SAFCON Co may be used. It is preferable that the product is capable of adjusting the rotation torque, and may be able to adjust freely the torque in a range of 0.2 (Kgf·cm) to 1.0 (kgf·cm).

(Motor-Drive Control by Operation of Operating Knob)

As shown in the block diagram in FIG. 4, the operating knob unit 170 is electrically connected to the control circuit 150. The control circuit 150, on the basis of the pulse signal from the rotation sensor 171a, calculates at least one of a direction of rotation, a speed of rotation, and an amount of rotation of the operating knob. Moreover, the control circuit 150 carries out at least one of the following:

- processing of applying a control signal related to the direction of rotation to the motor, in accordance with the direction of rotation of the operating knob,
- processing of applying a control signal related to the speed of rotation to the motor, in accordance with the speed of rotation of the operating knob, and
- processing of applying a control signal related to the speed of rotation (the amount of rotation) to the motor, in accordance with the amount of rotation of the operating knob.

According to such configuration, when the operator has operated the operating knob 171, it is possible to operate the motor 139 in real-time, and to make the ram member 131 advance or retreat, in accordance with the operation carried out by the operator. The processing described above may have been executed by a combination of a computer program and an electric circuit, or may have been executed only by the electric circuit.

(Control Example 1)

Moving the ram member 131 by operating the operating knob 171 will be described below. As the operating knob 171 is rotated, the rotation sensor 171s generates a pulse signal, and the control circuit 150 controls an operation of the motor 139 on the basis of the pulse signal. An arrangement may have been such that in a case in which the rotating knob 171 is rotated in a clockwise direction, the ram member 131 advances in real-time, and in a case in which the rotating knob 171 is rotated in a counterclockwise direction, the ram member 131 retreats in real-time. A relationship of the amount of rotation of the operating knob 171 and the amount of movement of the ram member 131 may have been set to be such that when the knob is rotated through one rotation, the amount of movement of the ram member is L1 [mm] (R1 [rotations] in terms of the amount of rotation of the motor). Although the amount of movement L1 is not limited in particular, it is preferable that the amount of movement L1 has been set to be at the same level as the amount of movement of the ram member when the convention mechanical knob is rotated through one rotation.

(Control Example 2)

Figure 9:
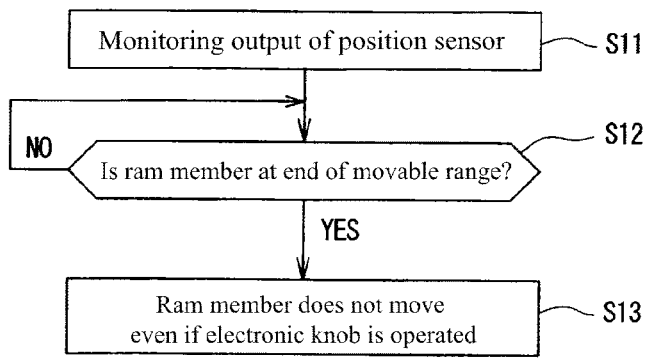
FIG. 9 is a flowchart related to an example of a control in which characteristics of the operating knob are used.

In the present embodiment, the following control may be carried out by using the features of the operating knob 171. As shown in a flowchart in FIG. 9, the control circuit 150, to start with, monitors a detection result of the position sensor 162 (refer to FIG. 4) (step S11). Moreover, the control circuit 150 makes a judgment of whether or not the ram member 131 has moved up to an end portion (most advanced position or most retreated position) of the movable range thereof (step S12). It is possible to carry out this judgment on the basis of a detection result of the first position sensor and the second position sensor.

Next, in a case in which a judgment has been made that the ram member 131 has moved up to the end portion of the movable range, the motor 139 is not let to rotate even when the operating knob 171 is rotated further (here, 'rotated further' refers to the ram member rotated in a direction of advance toward outside of the movable range) (step S13).

In such manner, according to a configuration of inhibiting the movement in a case in which the ram member is not in the movable range, it is possible to prevent an occurrence of malfunction caused due to the ram member 131 moving up to an unanticipated position. An arrangement may be such that such type of control is executed for both of an advance-end and a retreat-end of the movable range of the ram member, or is executed for one of the advance-end and the retreat-end of the movable range of the ram member.

(Control Example 3)

In the present embodiment, the following control may be carried out by using the peculiarities of the operating knob 171. The operating knob 171, as mentioned above, is to be operated in a case such as of filling up an inside of the chemical-liquid tube with a chemical liquid at the time of connecting the chemical-liquid tube for example. As a specific example, this is an operation of feeding (discharging) a small volume of the chemical liquid by making the ram member 131 advance a little, thereby filling up the chemical-liquid tube by the chemical liquid fed (discharged). In a case of the mechanical knob, the amount of movement of the ram member, when rotated through one rotation, being fixed physically, cannot be changed. However, the following control may be carried out by using the features of the operating knob.

Figure 10:
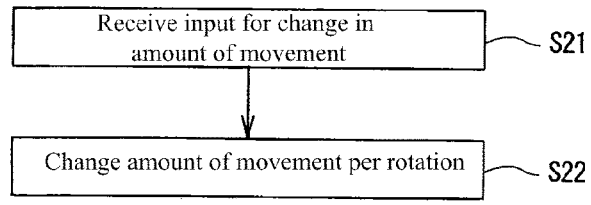
FIG. 10 is a flowchart related to another example of a control in which characteristics of the operating knob are used.

To start with, the control circuit 150, as shown in a flowchart in FIG. 10, receives an input for a change in the amount of movement (step S21). This input may be by operating (pressing, touching, or moving) some sort of a physical button provided to the chemical-liquid injector or an image button displayed as a graphical user interface, by the operator.

In a case in which there has been the input, the control circuit 150 receives that input, and changes the amount of movement of the ram member per rotation of the operating knob. In other words, the control circuit 150 switches a first setting (the amount of movement L1 [mm] of the ram member (R1 [rotations] in terms of the amount of rotation of the motor) when the operating knob is rotated through one rotation) to a second setting (the amount of movement L2 [mm] of the ram member (R2 [rotations] in terms of the amount of rotation of the motor) when the operating knob is rotated through one rotation, and here, L2<L1 and R1<R2). According to such arrangement, by switching to the second setting, since the amount of movement of the ram member per rotation of the operating knob becomes small, the operator is able to feed the chemical liquid more precisely. Such function is effective particularly in a case of filling up the chemical liquid up to a distal-end of a tube having a fine diameter.

In the description made above, although the first setting and the second setting have been exemplified, an arrangement may have been made to enable switching to three or more stages. An arrangement may be made such that the amount of movement of the rain member per rotation of the operating knob becomes smaller or larger, as compared to that in a default setting. An arrangement may have been made such that the fact that the amount of movement per rotation of the operating knob has been changed is displayed on the display 146 or a display unit other than the display 146.

(Control Example 4)

The conventional mechanical knob (not shown in the diagram) being mechanically connected to the part of the piston-driving mechanism, while the ram member is moved by pressing the physical button of the injection head for example, the mechanical knob (not shown in the diagram) would also rotate in conjunction with the movement of the rain member. In a case of the operating knob, the operating knob not being mechanically connected to the piston-driving mechanism, such movement in conjunction (interlocked movement) does not occur. Considering this point, it is preferable that an idea has been devised not to give an odd filling to the operator who is used to an apparatus (injector) with the conventional mechanical knob (not shown in the diagram). In a case in which there is no problem from a view point of a manufacturing cost and a set up space, an arrangement may be made such that an actuator (such as a motor) is built-in, and the operating knob is rotated by operating the actuator in conjunction with the operation of the piston-driving mechanism.

Moreover, in a case in which the light-emitting portion 173 has been provided as in the present embodiment, it is preferable to make an arrangement such that, a fact that the piston-driving mechanism is in operation is indicated by making the light-emitting portion 173 emit light in a predetermined pattern, instead of moving the operating knob. Examples of the 'predetermined pattern' are flashing with a first pattern corresponding to the rotation of the operating knob in the clockwise direction and flashing with a second pattern corresponding to the rotation of the operating knob in the counterclockwise direction. The first pattern and the second pattern may be differentiated by using different colors of light emitted, or by using different patterns, or by using a combination of different colors and different patterns.

In a case in which the plurality of light sources is built-in along a peripheral direction of the operating knob, an embodiment in which, the plurality of light sources is lit in order such that the direction becomes same as the direction of rotation of the operating knob, is preferable.

As described above, the injection head of the present embodiment converts the rotation of the operating knob to the electric signal, and controls the operation of the piston-driving mechanism electrically on the basis of the electric signal. Consequently, as compared to the case of the conventional mechanical knob, a displacement flexibility of the operating knob unit becomes high, and it becomes possible to carry out the operation of the piston-driving mechanism diversely.

Moreover, since such operating knob unit does not require the mechanical connection (coupling) as in the mechanical knob, it is extremely effective for noise reduction at the time of operation, and is preferable from a point that it is possible to reduce a psychological stress on a person examined in this type of medical equipment in particular.

In the abovementioned description, although the 'control example 2' to 'control example 4' in which the peculiarities of the operating knob are used have been exemplified, all of these controls are not necessarily required to be installed as functions of the injection head, and one control or two or more than two arbitrary controls may have been installed according to the requirement.

Although one embodiment of the injection head has been described above, other than the arrangements disclosed above, various modifications are possible as the injection head. For example, the injection head may include one or plurality of the following components: an inclination sensor, a motor-current detector, an RFID (radio frequency identification) communication device, a data receiver, a data transmitter and so on.

The inclination sensor detects an inclination of the injection head. Generally, in the injection head of this type, the suction of chemical liquid into the syringe is executed in a posture in which a distal-end side (in other words, a syringe-side) of the injection head becomes upward. Whereas, the injecting of chemical liquid is executed in a posture in which the distal-end side of the injection head becomes relatively downward (posture in which the tip-end side is directed somewhat downward). By using a detection result of the inclination sensor, it is possible to prevent the suction of chemical liquid or injecting of chemical liquid in a posture which is not desirable.

Motor-current detector monitors a motor current while the motor is in operation, and the control circuit calculates an estimated value of a pressure of the chemical liquid on the basis of the motor current.

The RFID communication device is a device which, by a non-contact method, reads information of IC tags attached to the syringe, the protective case, or other members. A writing function may have been provided according to the requirement.

The data receiver is for receiving predetermined information transmitted from external equipment.

The data transmitter is for transmitting predetermined information from the injection head to external equipment.

(Details of Light-Emitting Portion and Light-Emitting Pattern etc.)

Figure 23:
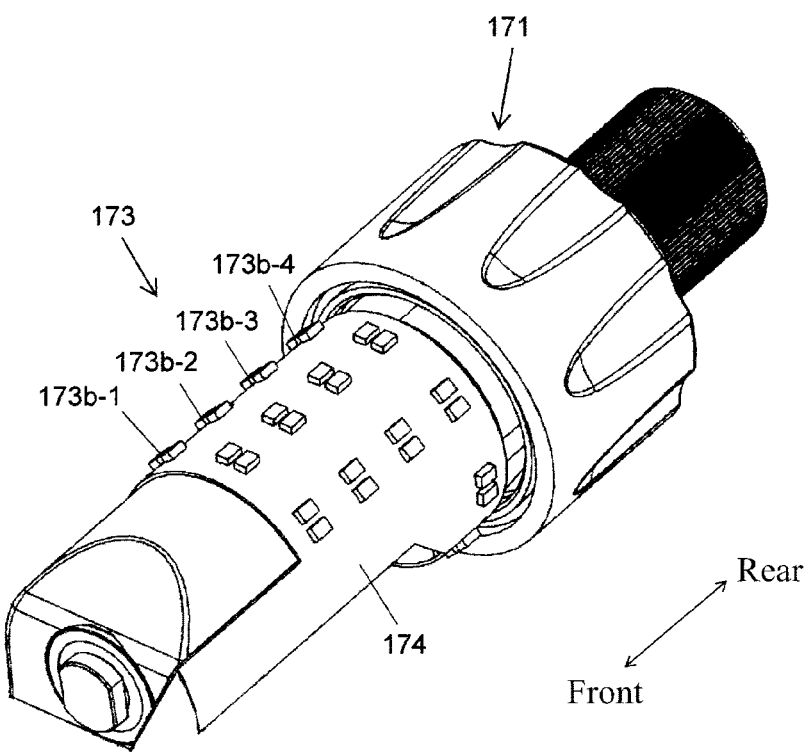
FIG. 23 is a perspective view of a specific arrangement of light-emitting portions near the operating knob.

The injection head may include the light-emitting portion 173 having an arrangement as shown in FIG. 23. The light-emitting portion 173 includes a plurality of light sources 173b-1 to 173b-4 disposed in a matrix form. Specifically, the plurality of light sources is disposed on a circumferential surface having a predetermined axis as a center. The 'predetermined axis' may be an axis same as a central axis of the operating knob 171. Or, the 'predetermined axis' may not be the same axis as the central axis, but may be a parallel axis. The plurality of light sources is not required to be disposed on the circumferential surface necessarily (details will be described below).

The light sources 173b-1 to 173b-4 can also be provided as one, two, three, or more than three light-emitting elements (such as LED elements). In this example, the light sources are provided as a pair of first light-emitting element and a second light-emitting element of different colors. Although the colors are not limited in particular, a blue color and a green color may be used.

The light sources 173b-1 to 173b-4 are disposed to form a plurality of columns leaving a distance mutually in a frontward-rearward direction (axial direction). It is possible to change the number of columns appropriately, and the number of columns may be let to be two, three, four, or more than four, or may be let to be only one.

The light sources 173b-1 to 173b-4 are disposed leaving a predetermined distance (equal distance for example) mutually in a circumferential direction. The light sources 173b-1 to 173b-4 may have been disposed over the entire periphery to surround the axis (shaft). Or the light sources 173b-1 to 173b-4 may have been disposed at least only on a portion of the circumference (for example, a range in which a center angle of a sector becomes at least 45° or more, a range in which the center angle of the sector becomes at least 60°, or a range in which the center angle of the sector becomes 90° or more).

The light sources 173*b*-1 to 173*b*-4 may have been mounted on a flexible substrate 174. The flexible substrate 174 may be fitted upon bending on a holding member (having an outer peripheral surface which is curved, for example) disposed in the injection head.

Figure 24:
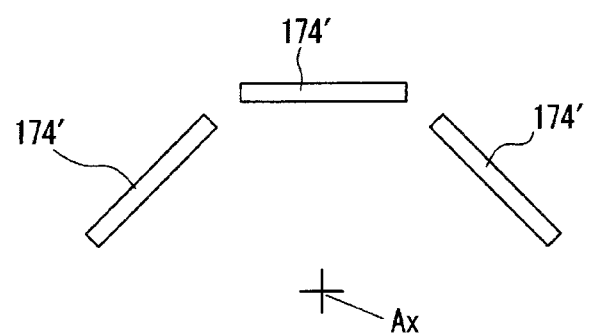
FIG. 24 is a diagram showing another example of an arrangement of substrates in the light-emitting portion.

As another aspect, the light sources 173*b*-1 to 173*b*-4 may be disposed to be dividing, on a plurality of substrates 174' as shown in FIG. 24. Even in such arrangement, by disposing the plurality of substrates 174' (may be substrates that are not flexible) around an axis Ax, as a result, the plurality of light sources is disposed in a circumferential direction of the axis Ax.

An example of control of the light-emitting portion 173 is as follows:

(1) Regarding Color of Light Emitted

An arrangement may be made such that while injecting a chemical liquid (while the ram member is advancing), the light-emitting element having a first color emits light, and when the operating knob 171 is turned while the chemical liquid is not being injected, the light-emitting element having a second color emits light. In one aspect, such operation control is carried out by the control circuit 150. As a matter of course, an arrangement may be made to change the color of light emitted in such manner at the time of retreat (while the ram member is retreating), without limiting to the advance.

As another example, this is also while the ram member is advancing, an arrangement may be made such that the color of light emitted differs for the main injection and an injection other than the main injection. A specific example includes an arrangement in which the color of light-emitted differs for the main injection and a pre-injection (such as a test injection or an injection for discharging an air-bubble). An arrangement may be made such that the color of light emitted differs for the movement of the ram member as an automatic injection (while injecting automatically) and the movement of the ram member in the manual operation.

(2) Pattern of Light-Emission (2-1) In order to know the direction of rotation of the operating knob 171, an arrangement may be used such that, according to the direction of rotation of the operating knob 171, the light sources 173*b*-1 to 173*b*-4 (may be in one column or in a plurality of columns) lined up in the peripheral direction emit light to be lit (to glow) in order in the peripheral direction. Such light-emission control is carried out at least in one of the clockwise and counterclockwise directions. An arrangement may be used such that the light sources go on emitting light with a substantially same speed as the rotational speed of the operating knob, or an arrangement may be made such that the light sources go on emitting light with a speed faster than or slower than the rotational speed of the operating knob. Such light-emission control for indicating the direction of rotation may by executed for only one of the plurality of columns, or may be executed simultaneously for two or more columns.

Figure 25:
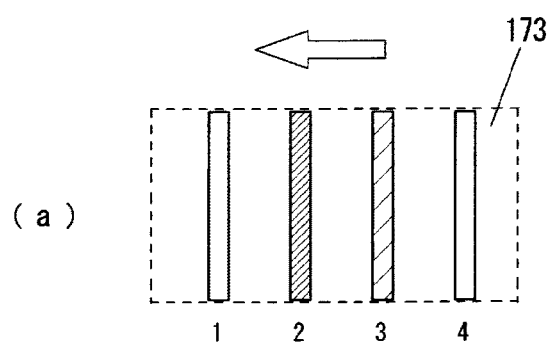
FIG. 25 is a diagram showing schematically an illumination pattern of the light-emitting portion.
Figure 25:
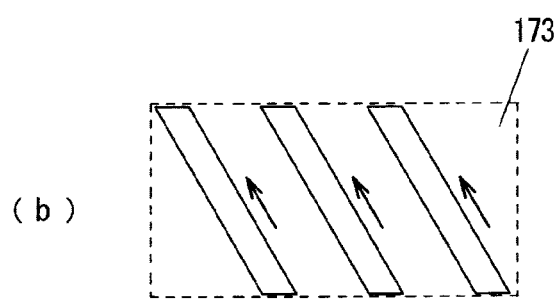

(2-2) A light-emission pattern which can reveal the advance and/or retreat of the ram member may be adopted. In other words, as a first example, as shown in FIG. 25(*a*), the light-emission pattern may be let to be such that the light sources are lit in order for each column from a rear side to a front side, and light in a circular shape or substantially semi-circular shape goes on advancing forward (sequential light-emission pattern, light-emission pattern in order). According to the requirement, the light sources may be made to emit light with a similar light-emitting pattern (however, the direction is opposite) even when the ram member retreats.

As a second example, as shown in FIG. 25(*b*), an arrangement may be made such that the light sources go on emitting light in order, to form a spiral trajectory. This light-emission pattern is also applicable both during the advance and retreat of the ram member.

(2-3) ON and OFF of Light Emission

As to how the light-emitting elements are made to emit light according to the rotation when the operator turns the operation knob has been described above, and the following control may be carried out as well. For a series of operations of the injection head, a timing preferable for inhibiting temporarily the movement of the ram member is also to be envisaged. An arrangement may be used such that at such timing, when the operating knob 171 is turned, the control circuit 150 does not rotate the motor, and also does not let the light-emitting elements emit light. According to such arrangement, since the light-emitting elements do not emit light even when the operating knob 171 is turned, the operator is able to make out visually that an input by turning the operating knob has been invalid.

Various light-emission patterns described above may be used appropriately for operations such as the following operations:

an automatic injection operation in which the ram member is moved with a predetermined speed to carry out the injection with set conditions, an operation of moving the ram member while the button on the head is being pressed, an operation of moving the ram member by turning the operating knob, an operation of moving the ram member up to a predetermined retracted position.

[4. Console]

As the console 210, it is possible to use for example, a console that is used in a conventional type of chemical-liquid injector. As shown in FIG. 4, the console 210 may include a control section 250, a storage section 261, a communication section 262, a slot 257, a touch panel 253, and a display 251. For example, the console may be of an integrated type in which the control section 250 is disposed in a housing, and the display 251 is disposed on a front surface of the housing. It may be a system using a plurality of consoles instead of using one console.

A shape of the housing is not limited in particular, and may be let to be a housing shape that is appropriately preferable according to a situation in which the console 210 is to be used. The housing shape may be as follows:

a floor-standing type housing shape suitable to be used by being disposed on a table in the operating room, a housing shape that can be fixed preferably to a wall or a predetermined supporting member (such as a thin housing of which a rear surface is formed to be substantially flat), etc.

The display of the console may be a display section in which an LCD (liquid crystal display) or an organic EL (electro-luminescence) display has been used. Moreover, the display may be a touch-panel display.

The control section 250 includes a CPU (central processing unit) which carries out arithmetic processing, a memory, and an interface, and which realizes various functions by executing computer programs stored in the memory. The control section 250 may include a processor having hardware such as a CPU, a ROM (read only memory), a RAM (random access memory), and an I/F, in which various computer programs are installed.

The control section 250 has a number of functions according to the computer programs installed, and following are examples as a function of the console: injection-protocol setting GUI (graphic user interface) display function, injection-protocol setting function, function of screen display during injection, function of screen display after injection, input detection function, injection control function.

The computer programs may have been stored in advance in the storage section of the console, or may have been downloaded from outside via the network, and stored in the storage section, or may be read from an information storage medium. Similar is the case for a computer program that controls the operation of the injection head, and the computer program may have been stored in a storage section of the injection head or a storage section of the console, or may be read from outside.

Each of the abovementioned functions will be explained briefly. The injection protocol setting GUI display function displays a GUI screen for setting the injection protocol, on the display. As a specific example, the injection protocol setting GUI display function displays at least one of icons such as a body-section icon, imaging-portion icon, and shows predetermined chemical-liquid injection conditions when that icon is selected.

The injection protocol setting function sets contents of check/correction after the chemical-liquid injection conditions shown above are checked/corrected by a physician or a medical staff.

The function of screen display during injection displays still images or animation images during injection of chemical-liquid, on the display. Moreover, the function of screen display during injection displays a pressure of the chemical liquid during injection of the chemical liquid.

The function of screen display after injection displays information related to the chemical-liquid injection that has been executed.

The input detection function receives an input from the physician or the medical staff, which was carried out via the touch panel or the physical buttons (for example).

The injection control function operates the piston-driving mechanism according to the input protocol that has been set, and executes the injection of the chemical liquid. Information related to conditions for operation of the piston-driving mechanism may be transmitted to the injection head from the console, and the control circuit of the injection head may control the piston-driving mechanism on the basis of the information transmitted.

The control section 250 may further have an injection-history generating function. The injection-history generating function is a function of generating injection-history data. The 'injection-history data' may be one or plurality of the following for example:
  data related to the operation of the heater (heating-start time and heating-end time),
  an injection operation ID which is unique identification information for each operation,
  date and time of start and end of injection,
  identification information of chemical-liquid injector,
  information of chemical liquid or imaging site that are injection conditions,
  information of chemical liquid or injection pressure as injection result.

Referring back to FIG. 4, the slot 257 is a portion into which a predetermined information storage medium is to be inserted, and the console 210 is capable of reading predetermined data from the information storage medium. An interface 269 is a connecting portion for making connections with the injection head 110. The console 210 may be connectible to an external network (such as a hospital system or the Internet) via the communication section 262. Although it is not shown in FIG. 4, the console unit 210 may have a hand-switch or a foot-switch as an inputting means. The hand-switch may be connected by wire or by wireless to the console, and operated at hands of the user, or may include a push-button type switch. The foot-switch may be connected to the console, or as shown in FIG. 2B, may be a foot switch 258 (refer to FIG. 2) connected to the power-supply unit 190. The operation of the injection head 110 and/or the console 210 may be controlled by operating the foot-switch 258. The foot-switch, in another aspect, may be connected to the injection head 110. The console may include a speaker (not shown in the diagram) for outputting a sound and/or voice. The console may include a microphone (not shown in the diagram) for inputting voice.

[5. Imaging Apparatus]

As the imaging apparatus 300, as shown schematically in FIG. 2A, it is possible to use a heretofore known imaging apparatus. As the imaging apparatus 300, an X-ray CT imaging apparatus 300-1 and an angiographic imaging apparatus 300-2 may have been provided. The angiographic imaging apparatus may have a C-arm.

The imaging apparatus 300 is communicably connected to the chemical-liquid injector 100, and exchanges predetermined information reciprocally. A start of operation or an end of operation of one of the imaging apparatus 300 and the chemical-liquid injector 100 may be synchronized with a start of operation or an end of operation of the other.

[Other Configuration Examples of Chemical-Liquid Injector]

Although, the present invention was described above by referring to the accompanying diagrams, as a matter of course, the technical items disclosed in the present specification can be appropriately combined, unless contradictory. Moreover, the present invention is not limited to the abovementioned content, and various modifications are possible.

(i) In a case of the type in which a chemical liquid is sucked into an empty syringe, the chemical-liquid injector may be configured as follows:

The syringe is set in the injection head, and in a state of a suction tube connected to a chemical-liquid bottle, when a predetermined button is pressed, a gasket (the a piston member and the plunger) moves forward, thereby carrying out the air extraction. Here, a specific example of the predetermined button may be an auto-fill button.

Next, suction of the chemical liquid is carried out.

As a step of suction of the chemical liquid, to start with, the chemical liquid is sucked up to part-way (in other words, instead of sucking the whole of the target volume, to suck only a part thereof).

Next, the operation of extracting air is carried out once again.

Thereafter, the suction of the chemical liquid is continued till the target volume is sucked. The suction speed may be same as the suction speed in the beginning, or may be faster (speed such that no air bubble is sucked into the syringe) than the suction speed in the beginning. Thereafter, by letting the piston member of the syringe to advance by a small volume, the preparation is completed.

(ii) In a case in which, the inclination sensor is built-in in the injection head, the control circuit 150 or the control section 250 carries out a part of or the whole of the following processing:

Making a judgment of whether or not the injection head is in a substantially vertical state (in other words, a state in which a front side of the injection head having the syringe loaded, is directed substantially vertically upward).

In a case in which the injection head is in the substantially vertical state, to allow execution of auto-fill operation. In a case in which the injection head is not in the substantially vertical state, to inhibit the auto-fill operation.

Making a judgment of whether or not the injection head is in a horizontal posture or in a posture in which the front side is relatively lowered.

In a case in which the injection head is in the abovementioned posture, to allow the operation of injecting chemical liquid. In a case in which the injection head is not in the abovementioned posture, to inhibit the injection operation.

Various components (such as devices, apparatuses, units, means, sections) in the present specification need not be independent individually, and a plurality of components may have been formed as one member. One component may have been formed of a plurality of members. A certain component may be a portion of another component. A portion of a certain component may be same as a portion of another component.

(6-1. Protective Case)

Figure 11:
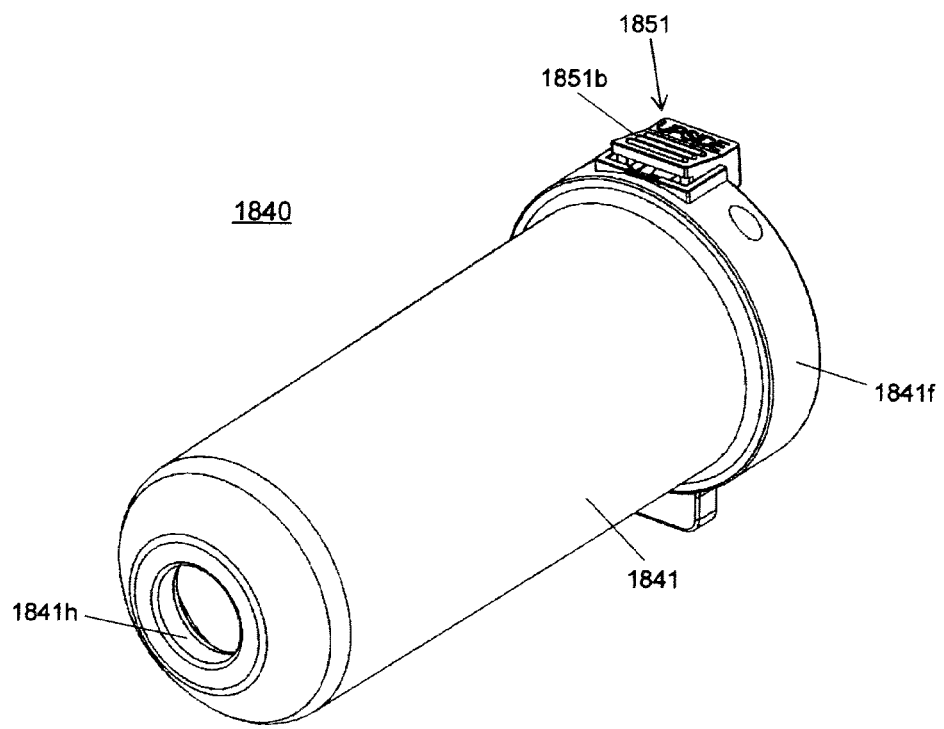
FIG. 11 is a perspective view of another protective case.
Figure 12:
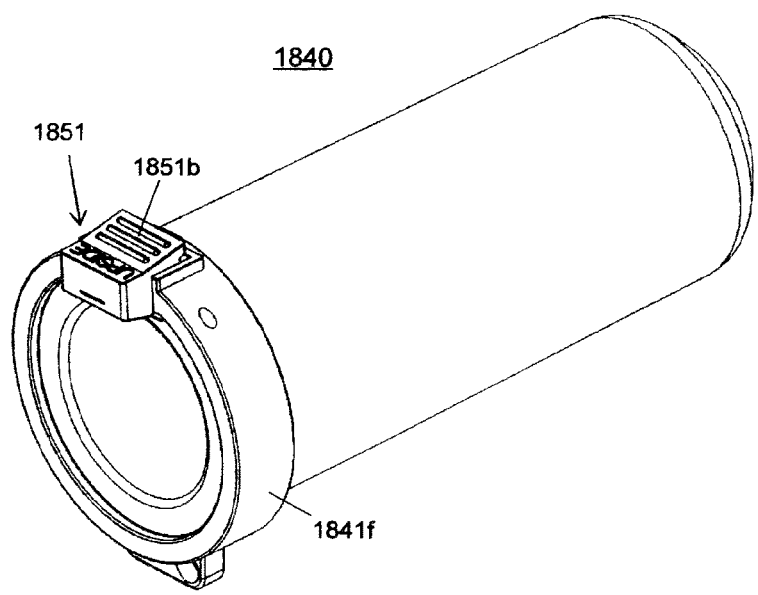
FIG. 12 is a perspective view of the another protective case.

It is possible to use a protective case as shown in FIG. 11 and FIG. 12. This protective case 1840 has a structure in which, an engaging member for preventing the syringe from falling off, is provided to the protective case 840 shown in FIG. 3. The protective case 1840 includes a main-body member 1841 having a substantially circular cylindrical shape into which a syringe is to be inserted. Regarding a material of the protective case 1840, since it is possible to use a material similar to that of the protective case in FIG. 4, the repetitive description thereof is omitted.

Moreover, a structure that an opening portion 1841h is formed in a distal-end surface of the main-body member 1841, and a structure that a flange portion 1841f is formed in a proximal-end portion of the main-body member 1841 are similar to those in the protective case in FIG. 3. As shown in a cross-sectional view in FIG. 13, an inner diameter d1841 of the main-body member 1841 may be substantially constant throughout, except for a part at a distal-end side and a proximal-end side. A recess 1843 which receives the flange portion 811f of the syringe (refer to FIG. 3) is formed in the proximal-end portion of the main-body member 1841. A contour shape (shape viewed from an axial direction) of the recess 1843 is circular for example, and an inner diameter thereof is formed to be slightly larger than a diameter of the flange portion 811f. Another example of the contour shape of the recess 1843 will be described later.

Figure 13:
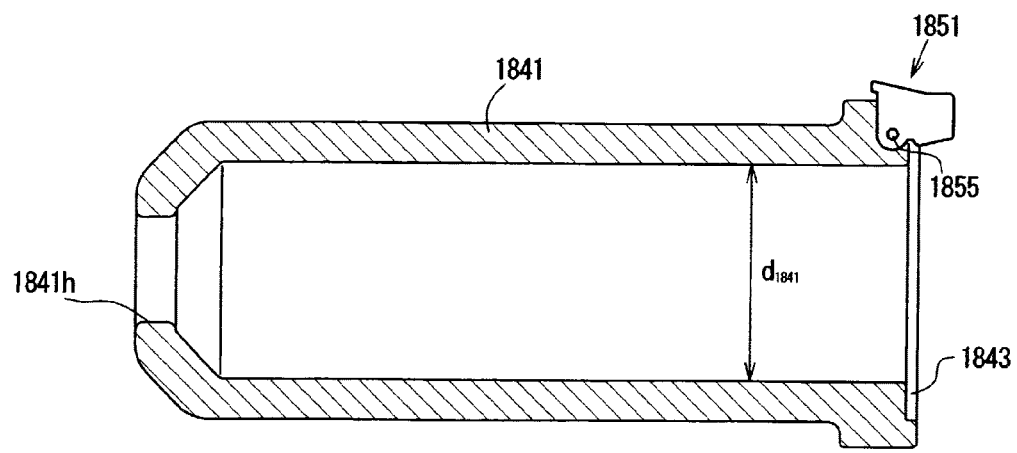
FIG. 13 is a cross-sectional view of the protective case.

An engaging member 1851 is provided to a portion of the flange portion 1841f (FIG. 11 to FIG. 13). The engaging member 1851 is pivotably held with a shaft 1855 as a center. The shaft 1855 may be disposed along a direction orthogonal to an axis line of a syringe inserted, or along a practically orthogonal direction.

Figure 14:
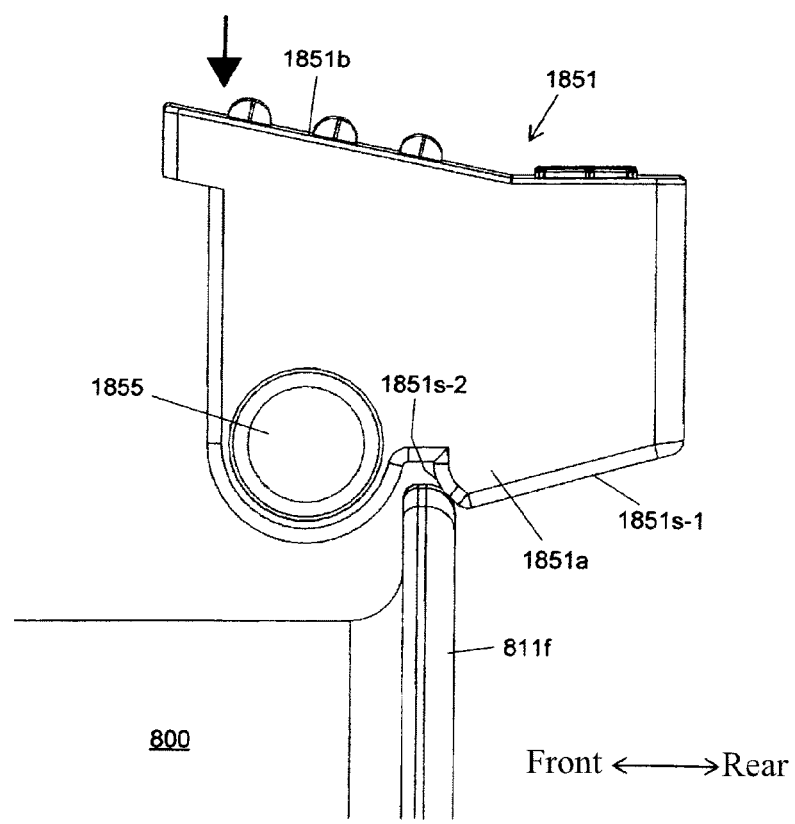
FIG. 14 is an enlarged view of a surrounding of an engaging member.

The engaging member 1851, as shown in FIG. 14, includes a projecting portion 1851a (that will be described later in detail) which is latched with the flange portion 811f of the syringe 800. The projecting portion 1851a can also be called as a ratchet for example.

An operating portion 1851b is formed on an upper-surface side of the engaging member 1851 (also refer to FIG. 14), and by pushing the operating portion 1851b, the overall engaging member 1851 is pivoted around the shaft 1855. The operating portion 1851b is not required to be pushed necessarily by the operator, and may be pushed by a predetermined unit.

A state in which the projecting portion 1851a of the engaging member 1851 locks the flange portion 1851a of the syringe will be referred to as a 'closed position', and a state in which the engaging member 1851 is pivoted around the shaft 1855 and the projecting portion 1851a is raised up will be referred to as an 'open position'. Although it is not limited, a bias applying member (not shown in the diagram) which applies a bias to the engaging member 1851, in a direction such that the engaging member 1851 assumes the closed position, may have been provided to the engaging member 1851. It is possible to use a spring (such as a plate spring or a coil spring) as the bias applying member.

A specific shape of a distal-end side of the projecting portion 1851a is variable to a wide range of shapes. For example, as shown in FIG. 14, the shape may include a tapered surface 1851s-1 at a rear side in the axial direction and a tapered surface 1851s-2 at a front side, with an apex of the projecting portion 1851a as a reference (base). The 'tapered surface' may be a flat surface or a curved surface. In the example in FIG. 14, the tapered surface 1851s-2 is a curved surface, but it may be a flat surface.

In a case in which the tapered surface 1851s-1 is formed on the engaging member 1851 as shown in the example in FIG. 14, at the time of inserting a syringe into the protective case, the flange portion 811f of the syringe abuts with the same tapered surface, and along with being inserted, pushes the engaging member 1851 up and is pivoted toward an open direction. Moreover, as the flange portion 811f surpasses the projecting portion 1851a, the engaging member 1851 returns to the closed position by the bias applied, an edge of the flange portion 811f fits in a recess at a front side of the projecting portion 1851a, and the flange portion 811f assumes a locked state.

The 'locked state' is a state in which the syringe would not come off, and a part (tapered surface 1851s-2) of the engaging member 1851 may or may not abut with the flange portion 811f. In a case of abutting, the flange portion 811f of the syringe is pinched between an inner surface of the recess 1843 of the protective case and the engaging member 1851, and positioning of the syringe in the axial direction is carried out.

The syringe is to be removed from the protective case by the following method:

(i) Push the operating portion 1851b of the engaging member 1851, open the engaging portion, and remove the syringe.

Figure 15:
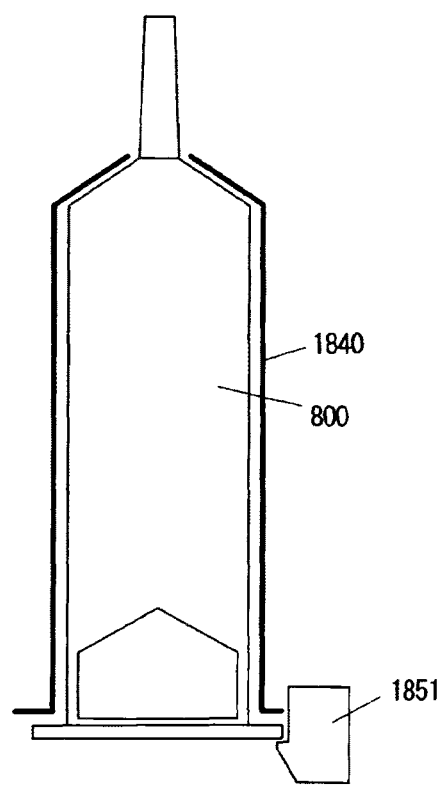
FIG. 15 is a schematic diagram of a state in which the syringe is loaded in the protective case.

Moreover, it is preferable to have an arrangement such that the syringe comes off by the following method:

(ii) Without pushing the operating portion 1851b of the engaging member 1851, by applying a force in a downward direction to the syringe in a direction shown in FIG. 15, the engaging member 1851 opens and the syringe comes off.

In this case, more specifically, the syringe does not come off only by holding the protective cover 1840 and the syringe 800 simply in this direction (in other words, the syringe would not come off only by a weight of the syringe and the content inside), and an arrangement may be used such that the syringe comes off when an external force of a magnitude more than a predetermined magnitude is applied to the syringe by shaking the protective cover 1840 and the syringe 800 in the downward direction. It is possible to realize the abovementioned arrangement by setting appropriately an angle of inclination of the tapered surface 1851 and an amount of overlapping of the flange portion and the projected portion.

Figure 16A:
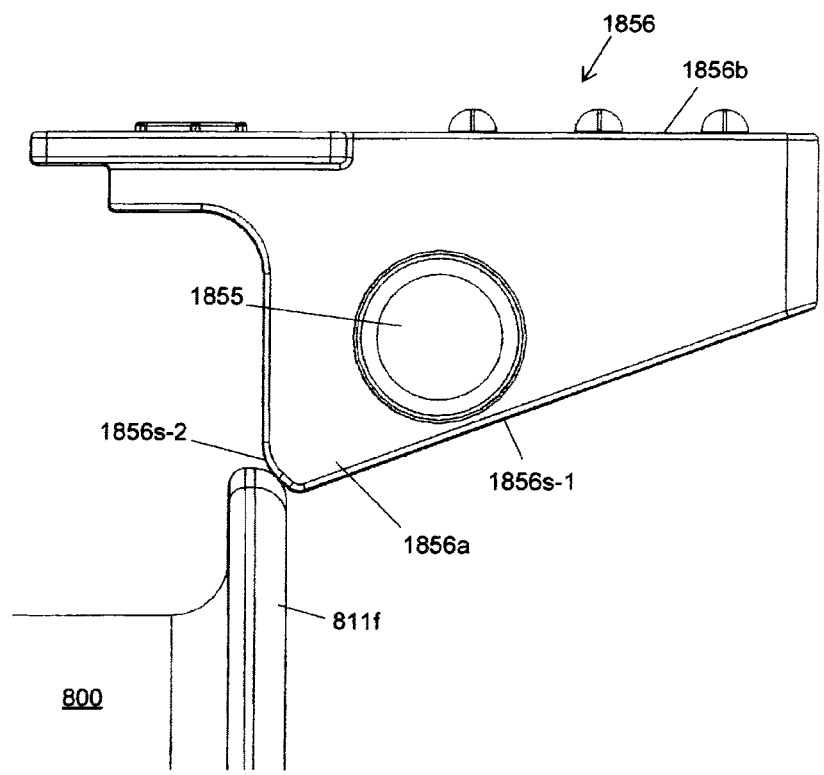
FIG. 16A is an enlarged view of a surrounding of an engaging member of another type.

The engaging member and the surrounding structure thereof is variable to a wide range of arrangements other than that described above. For instance, as shown in FIG. 16A, the structure may be such that an operating portion 1856b of an engaging member 1856 is provided to a rear side of the shaft 1855. In this case, by pushing the operating portion 1856b downward in the diagram, the engaging member 1856 is pivoted clockwise with the shaft 1855 as a center, and an apex of a projecting portion 1856a moves up to an outer side of an edge of the flange portion 811 of the syringe. Accordingly, the flange portion is unlocked, and the syringe is in a state in which it can be removed. Regarding the configuration in FIG. 16A, same or corresponding reference numerals are assigned to structural components having the same function as in FIG. 14, and repetitive description thereof is omitted.

The two examples of the engaging members were described above, but a specific shape and direction of pivoting of the engaging member may be changed appropriately, provided that the function of the engaging member of preventing the syringe from falling is performed:

(i) The tapered surface 1851s-2 may be a flat surface parallel to a rear-end surface of the flange portion 811f of the syringe.

(ii) Two or more engaging members may be provided to the flange portion of the protective case.

(iii) It is preferable to let the contour shape of the recess 1843 of the protective case to be a shape other than the circular shape. Specifically, the contour shape of the recess 1843 may be let to be a so-called I-cut shape or D-cut shape corresponding to the shape of the flange of the syringe. The I-cut shape refers to a shape in which both sides of a circular shape are cut off linearly. The D-cut shape refers to a shape in which a portion of a circular shape is cut off linearly. When a flange shape of the syringe is polygonal, it is preferable to let the recess to have a polygonal contour shape.

In a case in which the contour shape of the recess is formed to be a shape (complementary shape) corresponding to the shape of the flange of the syringe, the syringe is prevented from rotating when set in the protective case. The rotation of the syringe being prevented in such manner, it becomes easy to carry out a job of connecting the chemical-liquid tube to a luer-lock portion (for example) of the distal-end portion of the syringe, and an improvement in efficiency of examination and reduction of mis-connection can be anticipated.

Figure 16B:
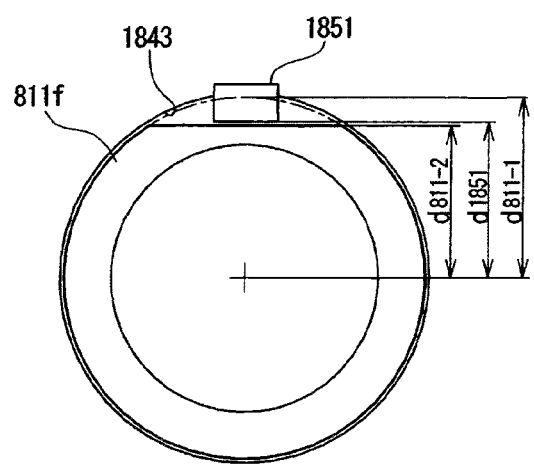
FIG. 16B is a diagram showing a relationship of the engaging member, the syringe, and a flange.

(iv) As a device in a case in which the shape of the syringe is the I-cut shape or the D-cut shape (in a broader sense, a shape in which a portion of an outer periphery may have a straight portion), the following arrangement may be adopted. The description will be made by citing an example of the case in which the shape of the syringe is the I-cut shape. For instance, an arrangement is such that, in a case in which positions of a cut-portion of the flange portion 811f of the syringe (refer to FIG. 16B) and the engaging member 1851 of the protective case are not aligned, the flange portion 811f cannot be inserted into the recess 1843 of the protective case. There are a few specific structures that may be possible, and it is preferable as one of the structures that, a relationship of (a) a radius $d_{811-1}$ of the flange portion 811, (b) a distance $d_{811-2}$ from a central axis up to the cut-portion, and a distance $d_{1851}$ from the central axis up to the lowest end of a flat surface on a frontward side of the engaging member 1851 (also refer to FIG. 12) is, the radius $d_{811-1}$>the radius $d_{1581}$>the distance $d_{811-2}$.

According to this structure, in the case in which the cut-portion is not aligned with the position of the engaging member, even when an attempt is made to insert the syringe, a portion of the syringe abuts with the flat surface on the frontward side of the engaging portion 1851 (a surface on the frontward side of the engaging member in FIG. 12), and the syringe cannot be inserted. An arrangement in which, it is easy for the medical staff to make out that the insertion is not possible obviously, is preferable to prevent effectively the syringe from being loaded erroneously.

(v) Another Example of Protective Case

Figure 26A:
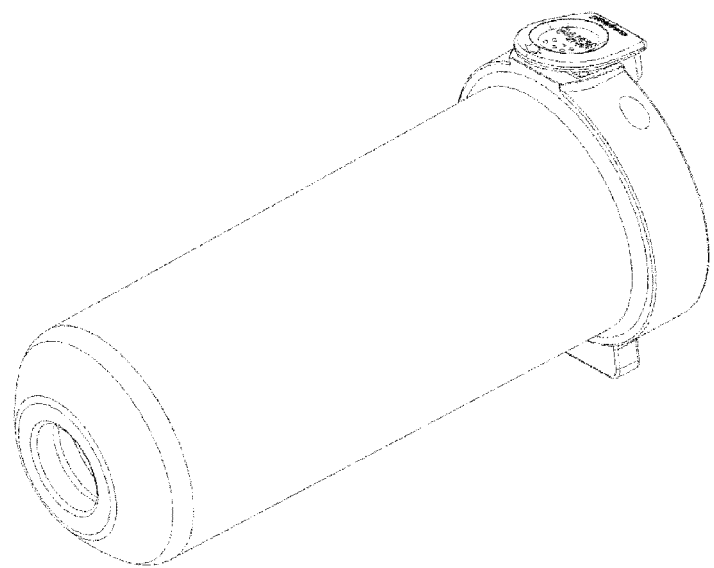
FIG. 26A is a perspective view when the protective case is viewed from a front side.

A protective case as shown in FIG. 26A to FIG. 26F may be used. This protective case, basically, has an arrangement similar to that of the protective case 1840 shown in FIG. 12, except for a point that an outward appearance of an upper portion of the engaging member differs. A portion to be pushed of the engaging member is a recess, in order to make it easy for the operator to push by a finger. Moreover, a plurality of protrusions for anti-slipping are formed inside the recess. FIG. 26A is a perspective view of the protective case viewed from a front-surface side. A function of the engaging member is same as that of the abovementioned engaging member of protective case 1840 in FIG. 11 and FIG. 12.

Figure 26B:
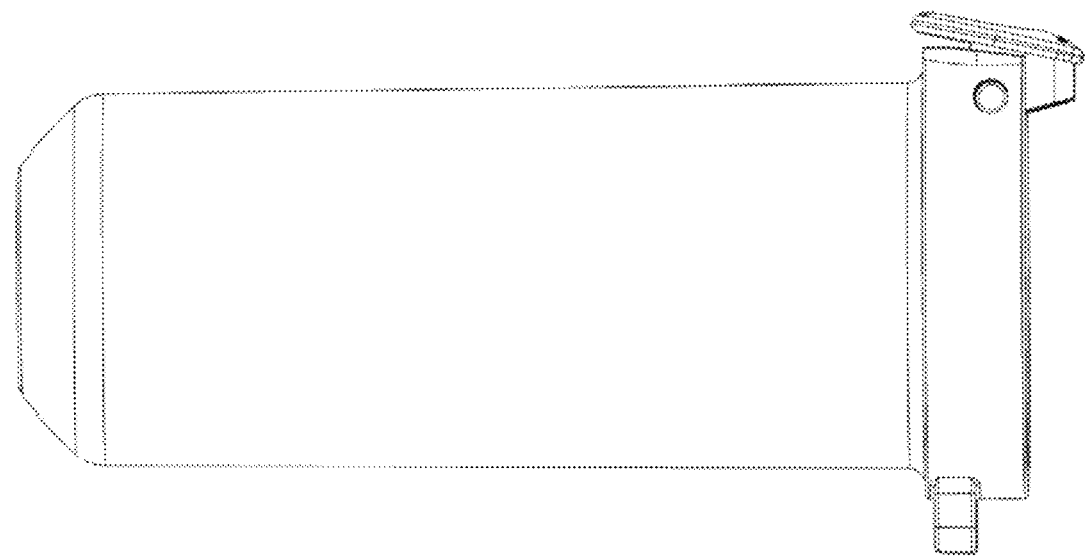
FIG. 26B is a right-side view and a plan view of the protective case.
Figure 26B:
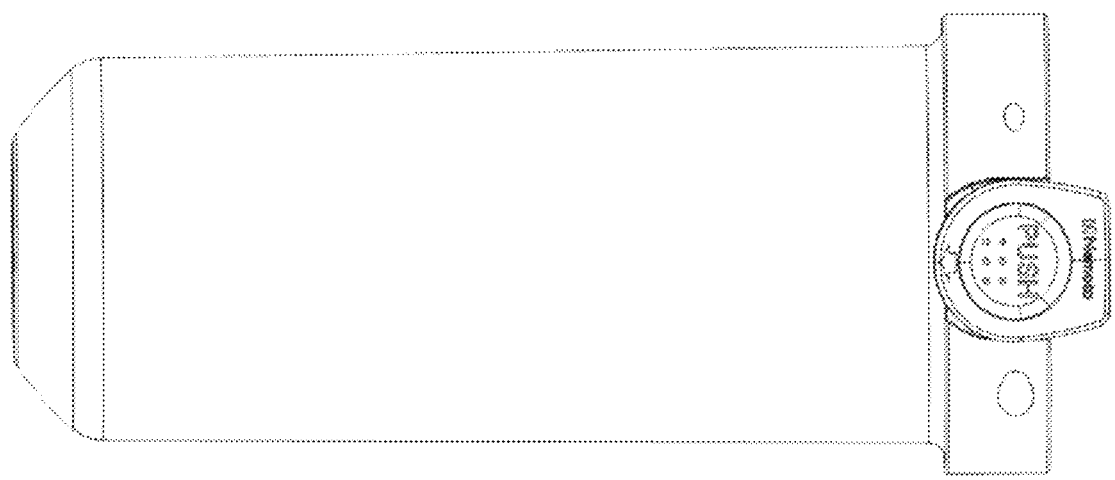
Figure 26C:
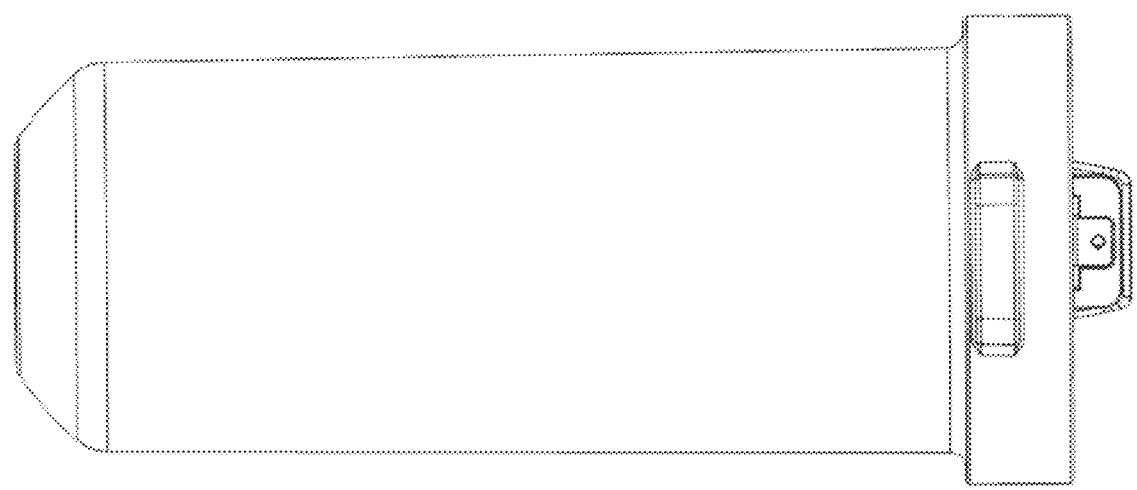
FIG. 26C (a) is a bottom view of the protective case, and (b) and (c) are diagrams showing only the engaging member.
Figure 26C:
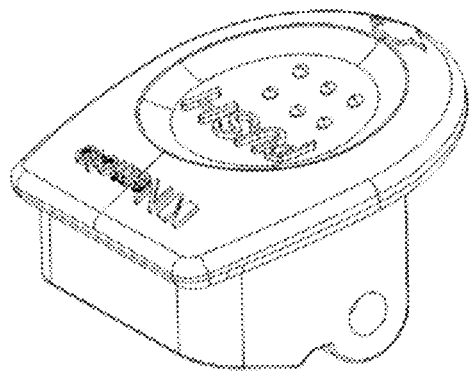
Figure 26C:
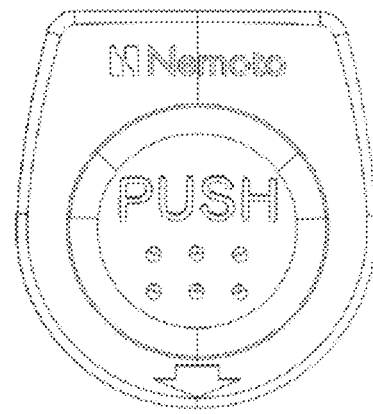
Figure 26D:
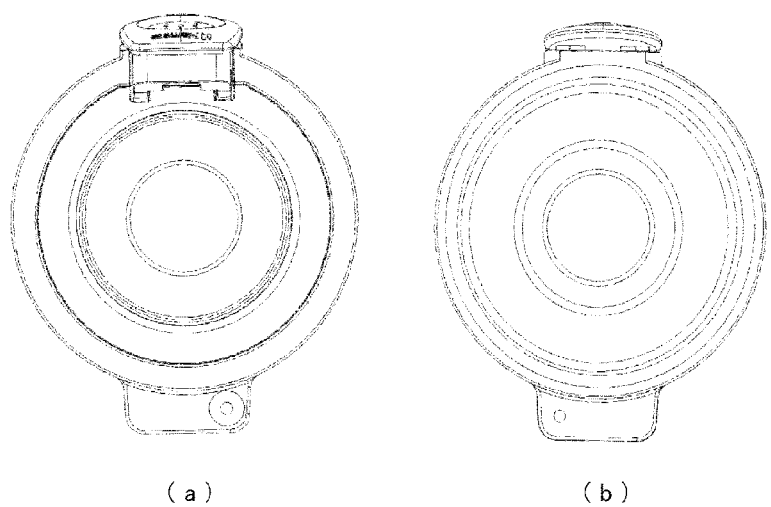
FIG. 26D is a rear view and a front view of the protective case.
Figure 26E:
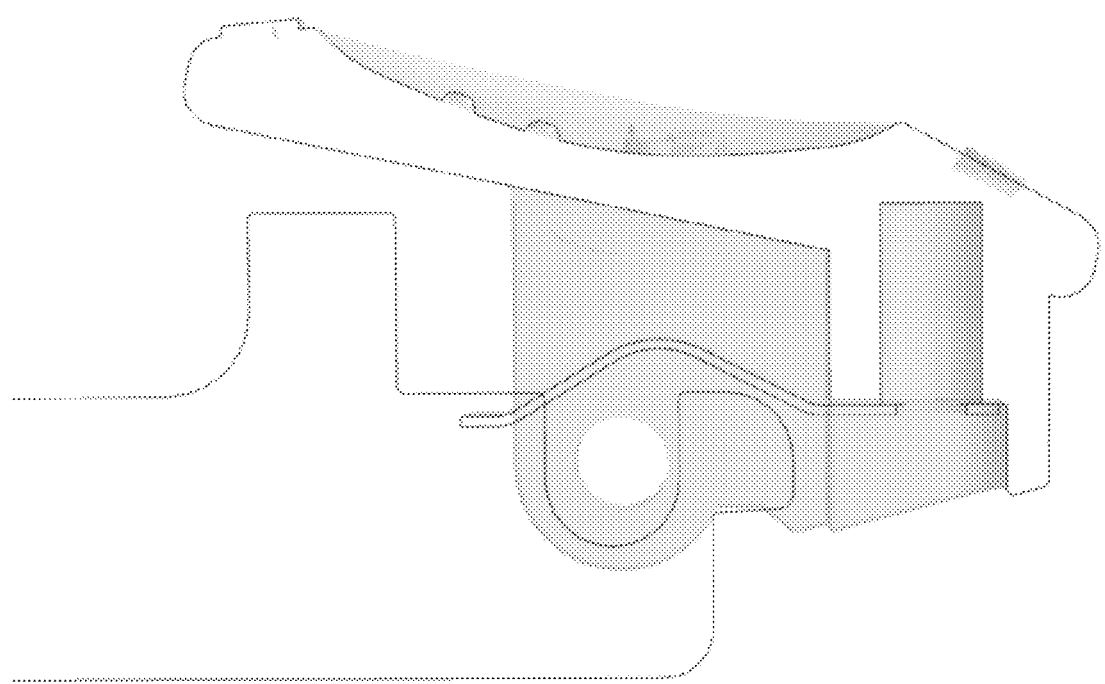
FIG. 26E is a cross-sectional view in which the engaging member is cut along a center line.
Figure 26F:
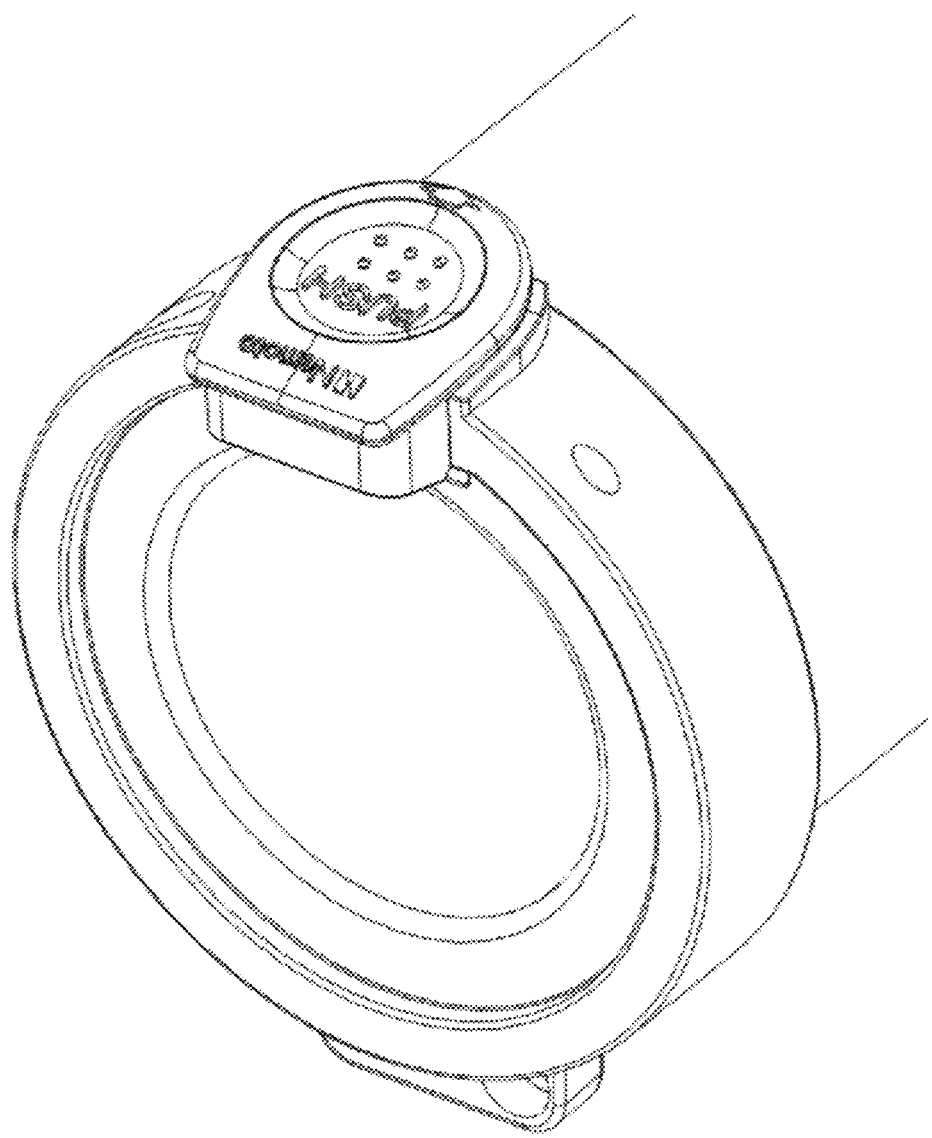
FIG. 26F is a perspective view when a part of the protective case is viewed from a rear-surface side.

FIG. 26B (a) and (b) are a right-side surface view and a plan view respectively of the protective case. FIG. 26C(a) is a bottom view of the protective case, and FIG. 26C(b) and (c) are diagrams showing only the engaging portion. FIG. 26D(a) and (b) are a rear view and a front view respectively. FIG. 26E is a cross-sectional view of the engaging member cut along a center line. FIG. 26F is a perspective view when a portion of the protective case is viewed from a rear-surface side. The present application discloses a design of an overall protective case, and also discloses a partial design for letting a portion of the engaging portion to be 'a portion intended to obtain design registration'. 'The portion intended to obtain design registration' may be identified as an area including both of the engaging member and the flange portion.

(6-2. User Interface)

The chemical-liquid injector may have one or a plurality of data of the screens such as the following screens, and may display that data: a start self-check screen, an angio-mode (angiography-mode) screen, a home screen, an injection-result screen, a protocol-setting screen, and an error screen.

An angio mode may include a portion-selection screen, a procedure selection screen, a condition-setting screen, a standby screen, an injection-on screen, and an injection-end screen. An arrangement may such that it is possible to shift from the home screen to at least one of the injection-result screen, the protocol-setting screen, an environment-setting screen, a user-edit screen, the portion-selection screen, and the condition-setting screen.

Figure 17:
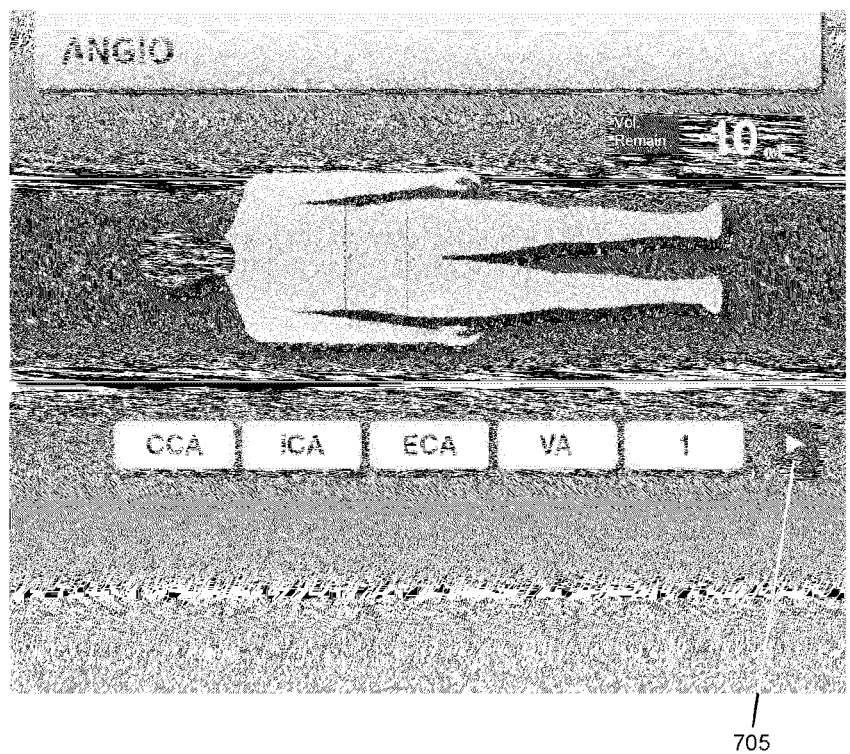
FIG. 17 is one screen (state 1) of a graphical user interface.

The chemical-liquid injector, in addition, may display a user interface images as follows. An image in FIG. 17 is one of the images for protocol-setting, and is a user interface that is displayed on a display. FIG. 17, for example, indicates a state in which head has been selected as a part of patients body, and icons of a plurality of detailed items are displayed accordingly. Here, 'CCA' denotes a common carotid artery, 'ICA' denotes an internal carotid artery, 'ECA' denotes an external carotid artery, and 'VA' denotes a vertebral artery.

Figure 18:
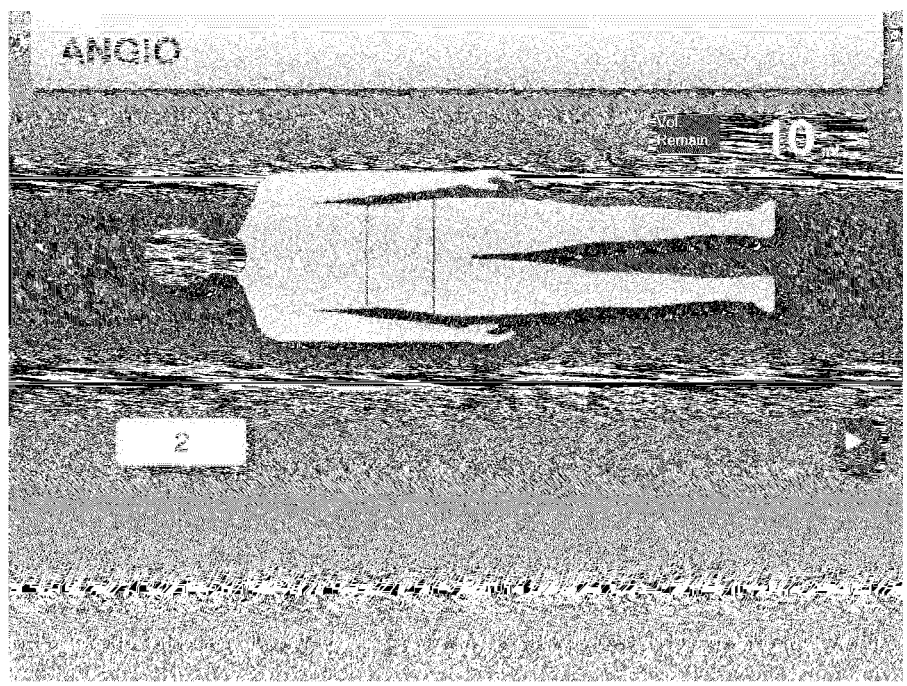
FIG. 18 is another screen (state 2) subjected to transition from the screen in FIG. 17.

In a case in which, the icons of detailed items cannot be displayed in their entirety on one screen, a cursor icon 705 may be displayed. The chemical-liquid injector may receive an input that the cursor icon 705 has been selected, and thereafter, the screen may shift to a screen displaying the remaining icons of detailed items as shown in FIG. 18. The selection of the cursor icon 705 may be by input by the operator via the touch panel or the icon may be selected by a cursor on the screen.

Figure 19:
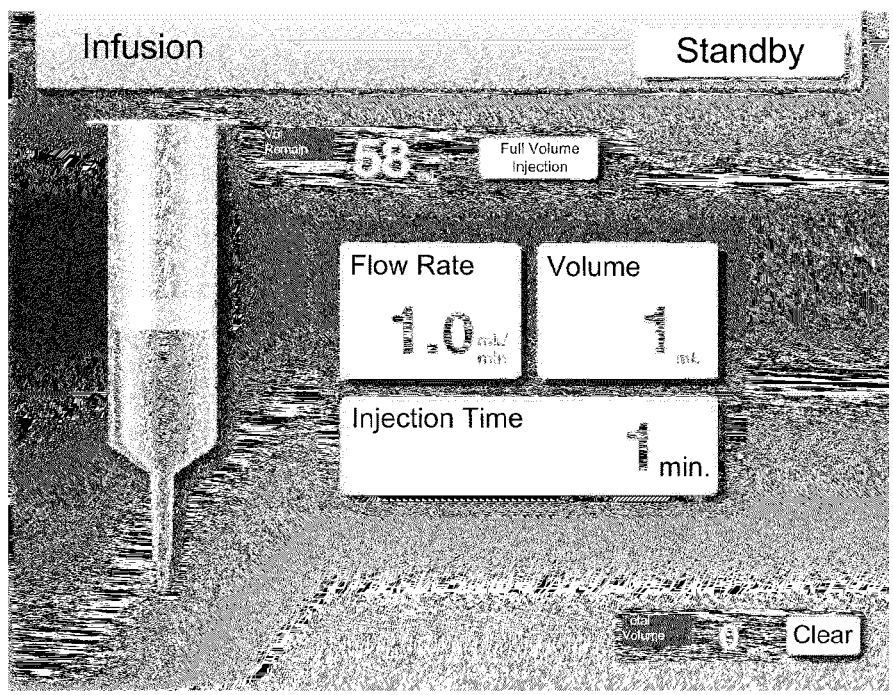
FIG. 19 is a screen for setting conditions.

A screen shown in FIG. 19 may be displayed as the screen for protocol setting. The chemical-liquid injector stores such screen data in a predetermined storage area, and displays on the display as a graphical user interface for condition setting. In this screen, the syringe is vertical. Moreover, in order to be able to input and/or change the rate, the volume, and the conditions, each thereof is displayed in a separate icon (in a box). Since the rate of injecting in angiography is not that fast as compared to that in the CT examination, the unit of rate may be let to be a volume injected per minute (ml/min) and not per second.

When the injection protocol is set via the screen, next, the injection of a chemical liquid is carried out. An arrangement may be such that to start injection, the physical button provided to the chemical-liquid injector (the injection head or the console) is to be pressed, or the injection is started by pushing a screen button.

Figure 20:
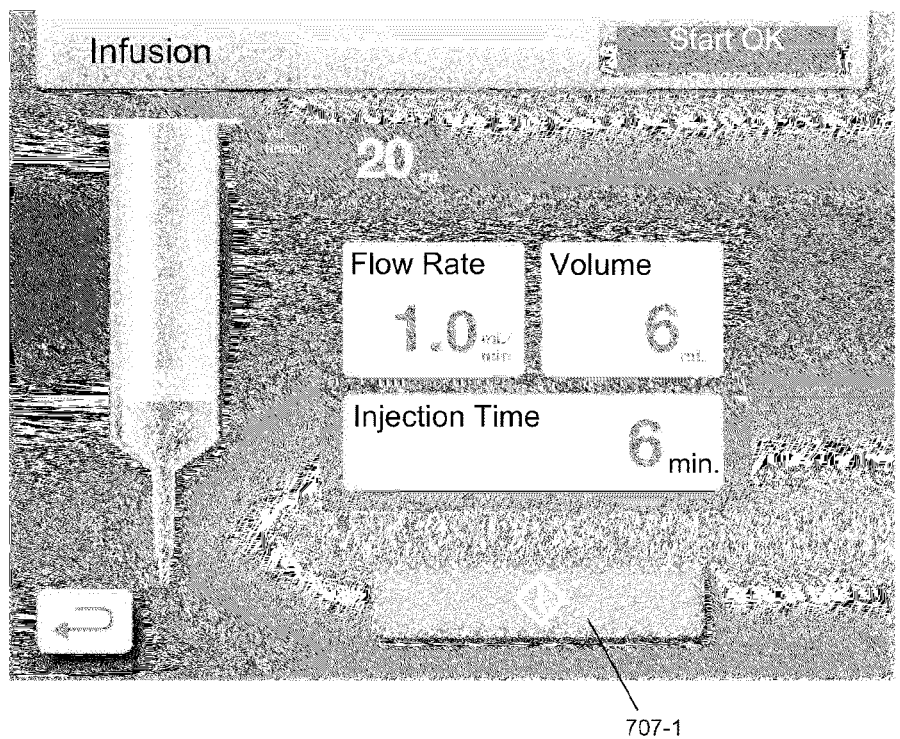
FIG. 20 is an example in which a button to start injection is displayed on the screen.

As a specific example, the screen may be a screen as shown in FIG. 20. FIG. 20 is an example of the standby screen. This screen includes a name of the injection mode (infusion), a syringe image, a remaining volume of chemical liquid, a rate, a volume, and a time. Moreover, a start-key 707-1 and a return key are displayed.

The chemical-liquid injector receives that the start-key 707-1 has been pressed, and starts injection accordingly. Moreover, the screen shifts from the setting screen to the injection-on screen. The selection, similarly as mentioned above, may be by input by the operator via the touch panel or the icon may be selected by a cursor on the screen. The return key icon is for releasing a standby state, and returning to the condition-setting screen.

Figure 21:
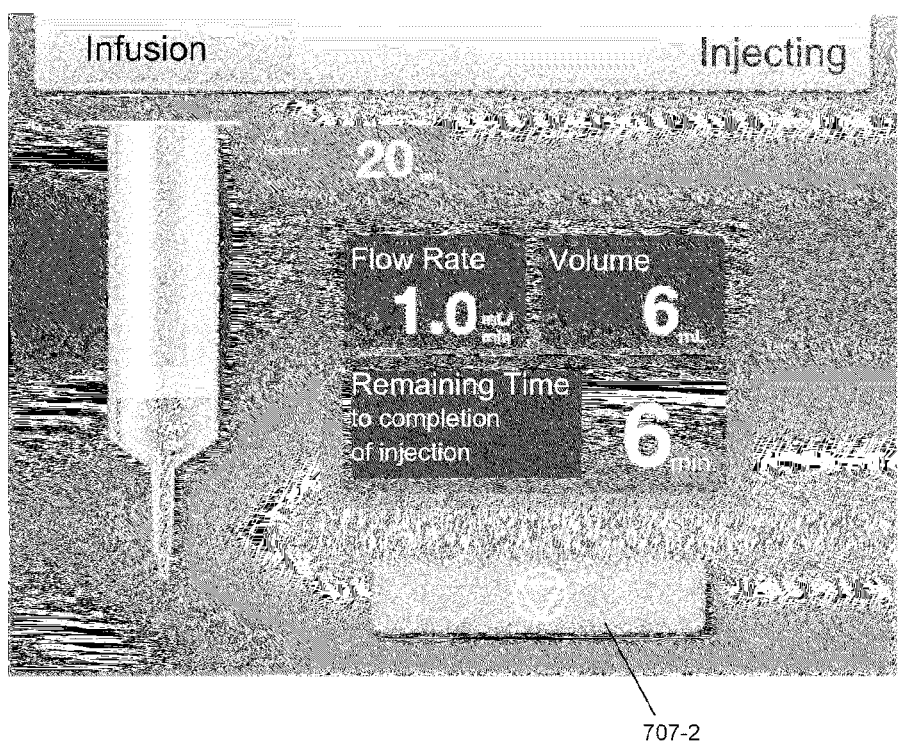
FIG. 21 is an example in which a button to stop injection is displayed on the screen.

The injection-on screen may be a screen as shown in FIG. 21. This screen includes a name of the injection mode (infusion), the syringe image, the remaining volume of chemical liquid, the rate, the volume, and the time. Moreover, a stop-key 707-2 is displayed.

The time display may be a display of time elapsed from the injection-start, or may be a display of countdown (in minutes or seconds).

In order that the injection-on is easy to make out, an animation display of a liquid droplet of a medicine being sent from the distal-end of the syringe may be adopted. Or, a portion of chemical liquid in the syringe may be displayed by a light and dark stripe pattern (for example), and an animation display of the portion of chemical liquid moving may be adopted.

The chemical-liquid injector, upon receiving the selection of the stop-key 707-2, stops the injection accordingly. Moreover, the screen shifts from the injection-on screen to the injection-stop screen. The selection, similarly as mentioned above, may be by input by the operator via the touch panel or the icon may be selected by the cursor on the screen.

As mentioned above, one of the start and stop of the chemical-liquid injection may be carried out with the input by the operator via the graphical user interface as a trigger. The start-key 707-1 for instance, is a display associating the physical button provided to the console, which is preferable in one form. It is preferable that at least one of a shape, a color, and a design of the button is common. Similar is applicable to the stop-key 707-2.

Figure 22:
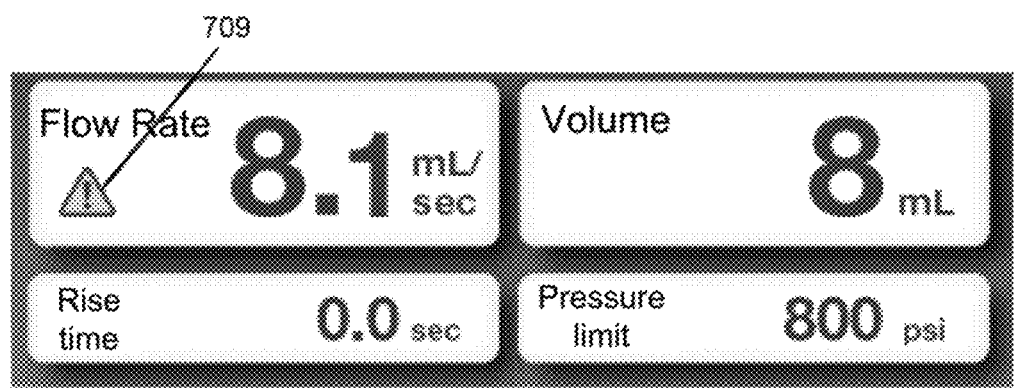
FIG. 22 is an example of a warning display.

A screen as shown in FIG. 22 may be displayed to prevent an inappropriate condition setting. FIG. 22 is a screen which enables to input and/or change conditions of the rate and volume. Although it is not limited, the screen may include an image for inputting and/or changing a 'rise' time, and an image for inputting and/or changing a value of a 'pressure limit'.

The chemical-liquid injector calculates the injection time on the basis of the values of rate and volume that have been input (may be even a value of the default setting). In this example, the volume is 8 ml and the rate is 8.1 ml/sec, and the injection time is less than 1 sec. This numerical value is only a reference value, and in a case in which the injecting time calculated is smaller than a predetermined threshold value (which is '1 sec' in this example), a warning display 709 may be displayed to draw the attention of the operator.

To describe as an operation of the apparatus (chemical-liquid injector), the chemical-liquid injector, first of all, makes a judgment of whether or not the injection time calculated is less than the predetermined threshold value, and in a case in which the injection time is less than the predetermined threshold value, the chemical-liquid injector displays the warning display 709 on the display.

According to such arrangement, since the warning is displayed in the case in which the injection time is less than the predetermined threshold value, it is advantageous from a point that it is possible to prevent such value smaller than the threshold value from being set.

(6-3. Brake Operation)

The chemical-liquid injector may carry out a brake operation as follows after the completion of injecting. The brake operation is for dealing with the following problematic points.

In other words, in the chemical-liquid injector, with an arrangement such that, after the completion of injecting, an electric power supply to the motor is simply stopped and no particular braking movement is carried out (such as opening of power-feeding terminals), a case in which the syringe piston is pushed back due to a residual pressure inside the syringe is envisaged. Whereas, in an arrangement in which the brake is applied thoroughly to stop at the injection-end position, there is a possibility that a chemical liquid is pushed out by the residual pressure inside the syringe, and the volume is such that it cannot be accepted.

Therefore, in an embodiment of the present invention, the control of the motor may be carried out such that a gradual braking effect is achieved. Specifically, an electrical braking such as a dynamic braking, which is a method of allowing the rotation of motor, may be carried out intentionally.

According to such control, after the injection-end, since the syringe piston is pushed back gradually, it is possible to either prevent or reduce a chemical liquid from being dripped from the distal-end of the syringe by the residual pressure of the chemical liquid being released. Moreover, it is also possible to prevent the syringe piston from retreating energetically.

[7. Still Another Embodiment]

(7-1. Support Shaft)

Figure 27:
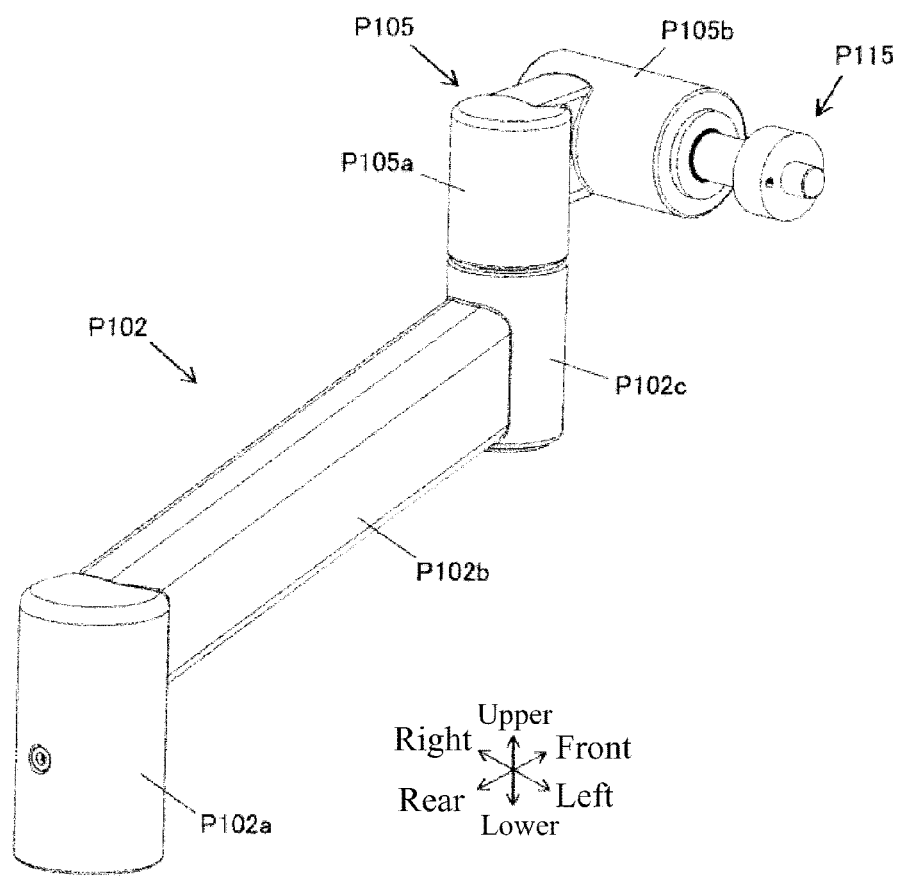
FIG. 27 is a perspective view showing an example of a holding structure for holding the injection head.

FIG. 27 is a perspective view showing an example of a holding structure holding the injection head. The holding structure, in this example, includes an arm member P102, a connecting member P105 which is connected to the arm member P102, and a support shaft P115 which is supported by the connecting member P105.

The holding structure of the injection head in FIG. 27 pivotably holds the injection head, and particularly, has a structure that prevents the fixing of the injection head from being loosened gradually due to being pivoted repeatedly.

The arm member P102 is not limited in particular, and is mounted to the supporting column 102a of the movable stand shown in FIG. 2C. The arm member P102, other than the supporting column 102a in FIG. 2C, may be fixed to a supporting column of a type provided to a bed of an imaging apparatus. The arm member P102 may be rotatably mounted (is rotatable around a vertical axis) to the supporting column.

The arm member P102 includes a first connecting portion P102a that is to be fixed to an object, an arm portion P102b extended from the first connecting portion P102a, and a second connecting portion P102c which is provided to a distal-end side of the arm portion 102b. The arm portion P102b, for instance, is extended from the first connecting portion P102a toward an upward inclined direction.

The connecting member P105 includes a first connecting portion P105a which is connected to the second connecting portion P102c of the arm member P102, and a second connecting portion P105b which is a portion that supports the support shaft P115.

A portion of the support shaft P115 is supported by the connecting member P105, and the other end portion is to be fixed to a frame (such as a metallic frame, not shown in the diagram) of the injection head. Here, the 'end portion' does not necessarily refer only to an end of the member, but is a concept including a certain area near the end.

Figure 28:
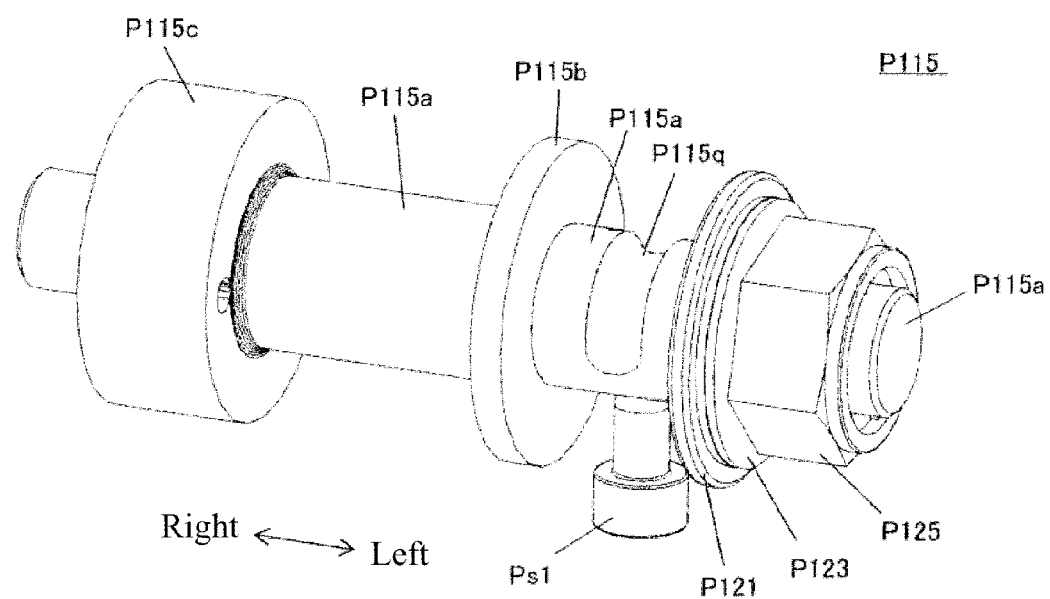
FIG. 28 is a perspective view of a support shaft (in a state of a nut fitted)
Figure 29:
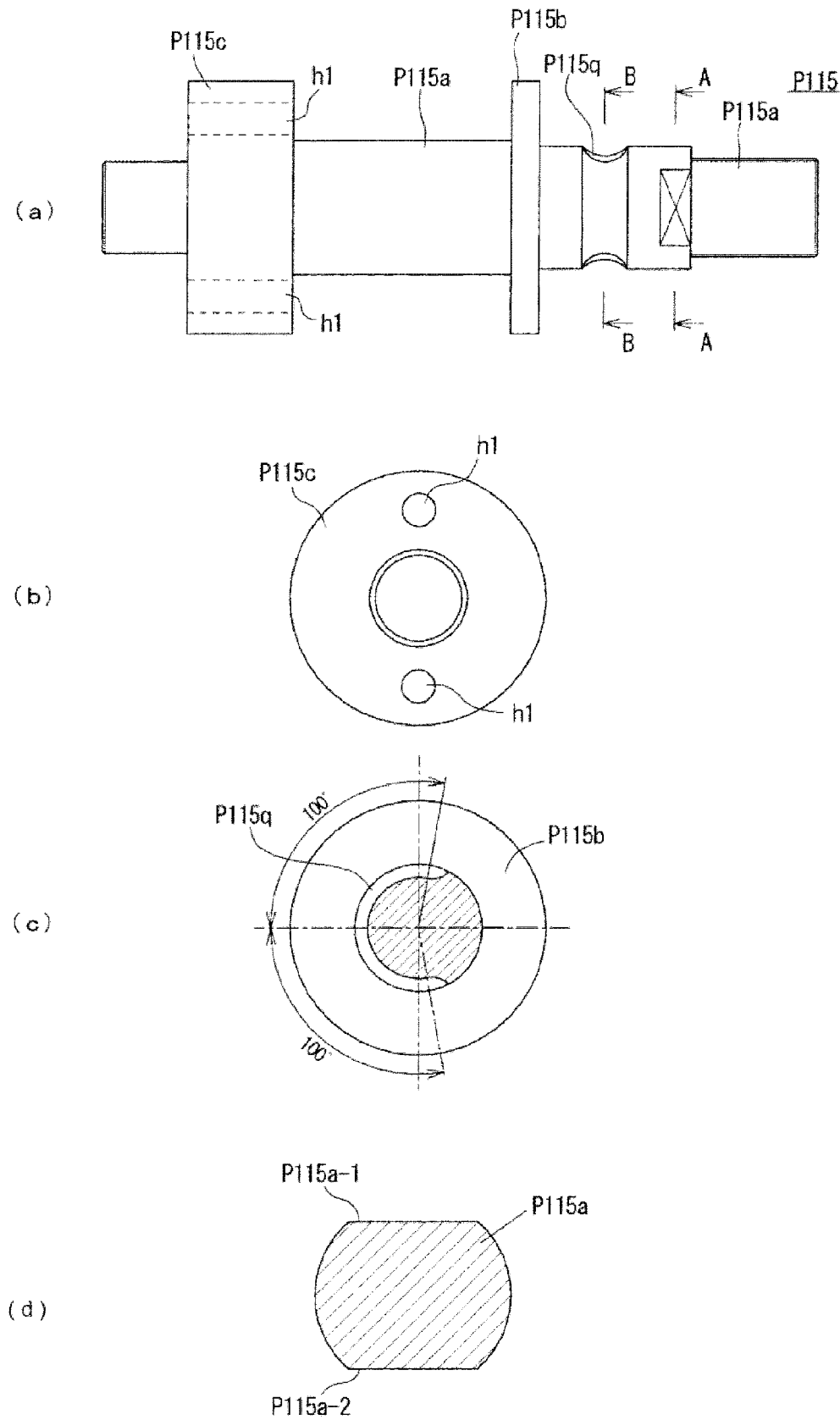
FIG. 29 is a plan view, a left-side view, a cross-sectional view along a line B-B, and a cross-sectional view along a line A-A.

The support shaft P115 has a shape as shown in FIG. 28 to FIG. 31. Specifically, the support shaft P115 includes a round shaft P115a, and a flange portion 115b and a fitting portion P115c are formed on the round shaft P115a. In FIG. 28, a state in which a collar P121, a plate spring P123, and a nut P125 are fitted to the round shaft p115a is shown.

A recess P115q is formed on a side opposite to the fitting portion P115c (right side of the flange portion P115b in FIG. 28), of the support shaft P115. The recess P115q is formed along an outer peripheral surface of a round rod, and is formed not on the entire circumference of the round rod, but over a predetermined range (such as a range of 200° in a peripheral direction as shown in FIG. 29(c). The recess P115q may have a quadrangular cross-section, and in the present embodiment, the recess P115q is a substantially semi-circular groove. A function of the recess P115q will be described later.

As shown in FIG. 29(a) to (d), at a portion of a section line A-A, the round shaft P115a has a cross-sectional shape having an upper and lower surface cut to be flat surfaces P115a-1 and P115a-2. An end portion of the round shaft P115a is formed as a screw portion, and a bolt is to be fastened to the screw portion, as it will be described later.

The flange portion P115b is a flat plate having a circular shape for example. The fitting portion P115c is a portion which is comparatively thick in order to be able to hold stably the injection head which is a heavy load. A plurality of through holes h1 through which a fixture such as a bolt is passed, is formed in the flange portion P115b.

Assembling of the support shaft P115 will be described below in further detail while referring to cross-sectional views 30.

An end portion on the opposite side of the fitting portion P115 is inserted into the connecting portion P105b of the connecting member. The connecting portion P105b is a structural portion in which a bottomed tubular body is placed sideways, and includes a tubular portion 105b-1, and a side wall P105b-2 formed on an end portion of the tubular portion 105b-1. An interior of the tubular portion 105b-1 is a column-shaped space. A through hole is formed in the side wall P105b-2, and the round shaft P115a of the shaft is passed through the through hole.

Sliding members P129-1 and P129-2 are disposed on both sides of the side wall P105b-2 for improving sliding. The sliding members P129-1 and P129-2 may be disc-shaped collars made of a resin. The material is not limited in particular, and it is possible to use a resin (such as POM (polyoxymethylene)).

The support shaft P115 is inserted into the connecting portion P105b up to a position where the flange portion 115b of the support shaft P115 abuts (or substantially abuts) with the sliding member P129-2. In this state, the round shaft P115a is passed through the through hole in the side wall P105b-2, and is in a state of being protruded into the interior of the tubular portion. Although it is not limited, the round shaft P115a may be inserted through the through hole while interposing a sleeve.

Figure 30:
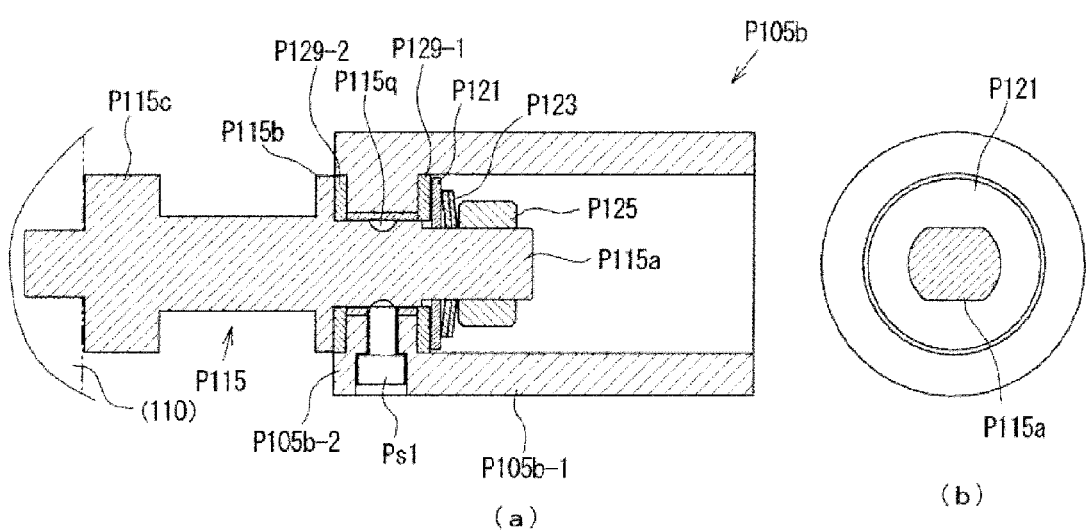
FIG. 30 is a cross-sectional view of a support shaft in assembled state and a surrounding structure thereof (present embodiment)

In a state of the support shaft P115 inserted, the recess P115q of the support shaft P115 is positioned in the through hole of the side wall P105b-2. The function of the recess P115q is as follows. In other words, as shown in FIG. 30, a fixing screw Ps1 is fitted into a hole formed at a position of the side wall P105b-2. When the fixing screw Ps1 is extended along a radial direction of the round shaft P115a, and is tightened fully, a distal-end of the fixing screw Ps1 enters into the recess P115q (although the recess is drawn upward in the diagram, the description above takes precedence over the diagram). According to such arrangement, an angle of pivoting (in other words, an angle of pivoting around an axis of the support shaft) of the round shaft P115a is regulated, and it is also possible to regulate an angle of pivoting of the injection head within a predetermined angle range.

(Tightening Structure at Distal-End Side of Shaft)

At the distal-end of the shaft, the round shaft P115a is provided with a collar P121, a disc spring P123, and a nut P125 in order.

The collar P121 is a washer, and a hole in the middle is formed to have the D-cut shape as shown in FIG. 30(b) and not a circular shape. The 'D-cut shape' typically refers to a shape in which one or two locations of a circular shape are cut off. Although it is usually preferable that lines to cut are straight lines, it is not necessarily limited to straight lines. In the present embodiment, it is a cut shape in which both end portions of a circular shape are cut off at two parallel straight lines.

A portion on which the collar P121 is mounted has a shape corresponding to a shape of the hole in the collar as shown in FIG. 29(d) and FIG. 30(b). The collar P121, in a state of being mounted on the shaft, rotates together with the shaft all the time, and cannot rotate relatively.

When the nut P125 is tightened up to a predetermined fixing position, the disc spring P123 (may be one or in plurality) is deformed in a direction of thickness, and by a bias due to deformation of the disc spring P123, the collar P121 is pressed against the sliding member P129-1. Moreover, also the flange portion P115b of the support shaft makes a close contact with the sliding member P129-2 on the outer side. In other words, the collar P121 and the flange portion P115b resiliently sandwich the side wall and the sliding member.

As shown schematically in FIG. 30(a), the fitting portion P115c of the support shaft P115 is connected to the frame (refer to reference numeral 110) of the injection head. Although it is not limited, the fitting portion P115c may be fixed by using a fixture such as a bolt.

According to the abovementioned arrangement, of the present embodiment, even equipment such as the injection head 110 which is comparatively heavy can be pivotably held with stability via the support shaft P115. Moreover, the merit of a structure in which the collar P121 with a non-circular hole as mentioned above has been used, is the following point. The description will be made while comparing with an arrangement in FIG. 31.

Figure 31:
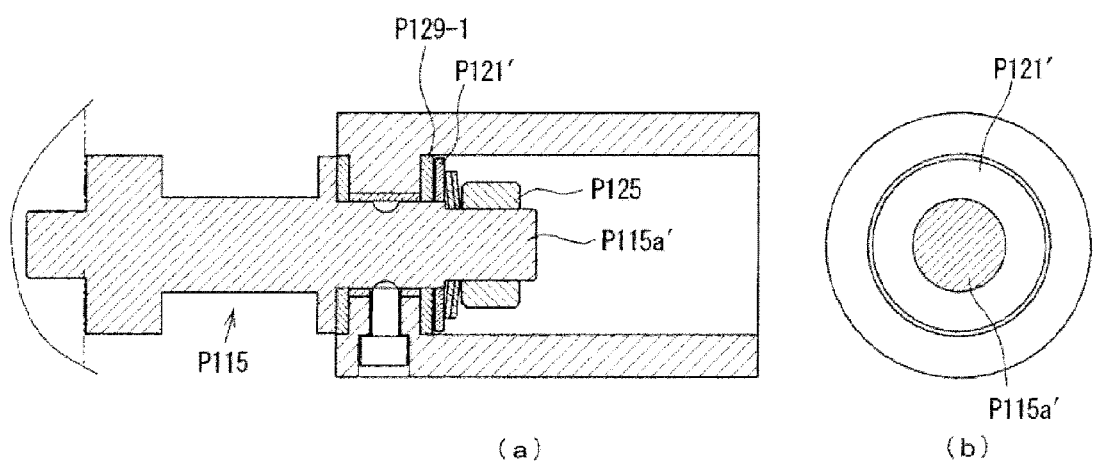
FIG. 31 is a cross-sectional view of a support shaft in assembled state and a surrounding structure thereof (embodiment for reference)

FIG. 31 is a cross-sectional view of a structure in which a collar P121' which is a normal washer, has been used. A hole at the center of the collar P121' is formed to be circular. In this structure, at a portion on which the collar P121' is installed, a cross-section of a round shaft P115a' is formed to be circular-shaped as shown in FIG. 31(b).

In a case of the structure in FIG. 31, the collar P121' being relatively pivotable with respect to the round shaft P115a', even if the nut P125 has been fastened firmly when the product was assembled initially, there is a possibility that the nut P125 is gradually loosened while the pivoting of the injection head is repeated. The reason being that, while a force in an axial direction (rightward direction in the diagram) is applied to the nut P125 via the disc spring P123, and the nut 125 is in a state of being pressed, since the support shaft P115 is pivoted in conjunction with the pivoting of the injection head, as a result, a force in a direction of loosening is applied to the nut P125.

Whereas in the present embodiment, unlike the structure in FIG. 31, since the rotation of the collar P121 with respect to the round shaft is mechanically regulated, and the relative rotation is not possible (in other words, the collar P121 and the round shaft P115a are interlocked invariably), no force in the direction of loosening is applied to the nut P125, and consequently, there is loosening of the nut P125. As a result, over a long period of time, the injection head can be pivotably held with stability, and highly reliable medical equipment is provided.

A means to resolve the issues of the holding structure of the present embodiment is a point to inhibit the relative rotation of the collar with respect to the round shaft, and not to let the force in the direction of loosening to be applied to the nut. Accordingly, other than using the collar in which the hole having the D-cut shape is formed, it is possible to change appropriately the shape of the hole in the collar and the cross-sectional shape of the shaft, provided that the arrangement shows such effect. The shape may be a quadrangular shape and a polygonal shape, or a groove may be provided in the shaft (circular), and the rotation of the collar (circular hole) may be inhibited by interposing a key.

All of the specific components shown in FIG. 30 are not necessarily indispensable for the holding structure of the present invention. Moreover, it is possible to make various modifications (changes) without departing from the scope of the present invention.

In the description above, the following invention is disclosed:

1. A holding structure including,
    a shaft P115 (or may be an extended shaft which is fitted to the object side) which is connected to an object (medical equipment such as an injection head), and which is pivoted together with the object,
    a holding member P105b which holds the one end side of the shaft, and
    a fixing member (nut) which is fitted by being screwed to one end of the shaft, wherein
    the shaft is pivoted with respect to the holding member, and
    a collar (washer) and a bias applying member (which generates a bias in the axial direction of the shaft, the disc spring P123 in the abovementioned example) are disposed between the nut and the holding member (specifically, a portion thereof through which the shaft passes, the side wall P105b-2 in the abovementioned example), and the collar does not rotate relatively with respect to the shaft. The number of disc springs may be one or in plurality.

2. Moreover, the member (disc-shaped member made of resin for example) for improving the sliding is disposed between the side wall and the collar.

3. Furthermore, a means (P115q and Ps1) which regulates the angle of rotation of the shaft is provided.

(7-2. Specific Light-Emission Mode)
(Display of the Tight-Emitting Portion on the Rear-End Side of the Head)

Figure 32:
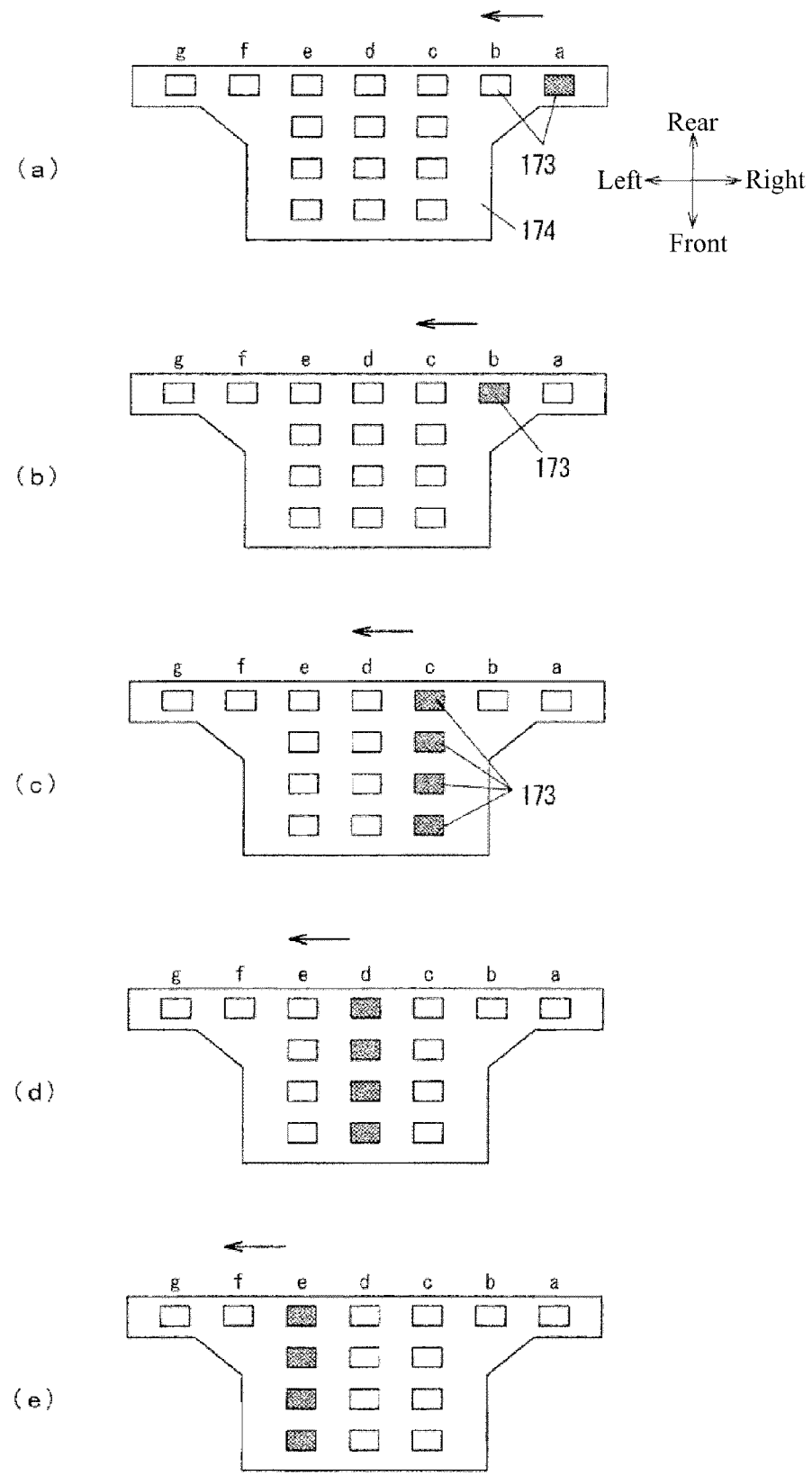
FIG. 32 is a diagram of a state in which a flexible substrate having a plurality of light sources disposed thereon is unfolded (one of light-emission patterns)

Specific aspects of light-emission by the light-emitting portion 173 will be described below by citing a number of examples. FIG. 32 is a diagram of a state in which the flexible substrate 174 having a plurality of light sources disposed thereon is unfolded. The plurality of columns from a to g of the light-emitting portions 173 are provided on the flexible substrate 174, and the columns from c to e in particular, are disposed in the matrix form. The matrix may have two or more rows and two or more columns, and in this example, the matrix has four rows and three columns. As a matter of course, the light-emitting portions may be disposed in three rows and three columns.

In a case of making the ram member of the piston-driving mechanism advance, the light-emission pattern may be let to be such that the light sources in a vertical column glow in order from right to left (or in the opposite direction), as shown in FIG. 32. The 'case of making the ram member advance' includes a case of making the ram member advance by pressing a jog button (advance button) of the injection head when an automatic chemical-liquid injection according to the set injecting conditions is carried out, and a case of making the ram member advance by a manual operation of the operating knob.

Although only up to a state in which the light-emitting portions in the column e are lit is shown in FIG. 32, thereafter, the column f and column g are lit in order, and returns to a state in FIG. 32(a).

Different light-emission patterns may be used when the automatic chemical-liquid injection is carried out and when the ram member is made to advance by pressing the jog button. For instance, at the time of injecting automatically, all (or some) of the light-emitting portions 173 may be made to blink simultaneously.

In a case of making the ram member retreat, the light-emission pattern may be such that the light-emitting portions are made to glow in order in the opposite direction of the direction mentioned above. This light-emission pattern may be used in cases such as making the ram member retreat by pressing the job button of the injection head.

Although it is not shown in the diagram, as another light-emission pattern, a pattern in which the light-emitting portions 173 in a horizontal column are lit simultaneously (in other words, light emission in a direction of row), and the light-emitting portions 173 glow in order, frontward or rearward, may be used.

In a case of making the ram member advance by turning the operating knob 171 (in the counterclockwise direction for example), the pattern may be let to be such that the light-emitting portions 173 in a horizontal column glow in order from the rear side to the front side. In a case of making the ram member retreat by turning the operating knob 171 in a reverse direction, contrary to the case of making the ram member advance, the light-emission pattern may be such that light sources in a horizontal column glow in order from the front side to the rear side.

Figure 33:
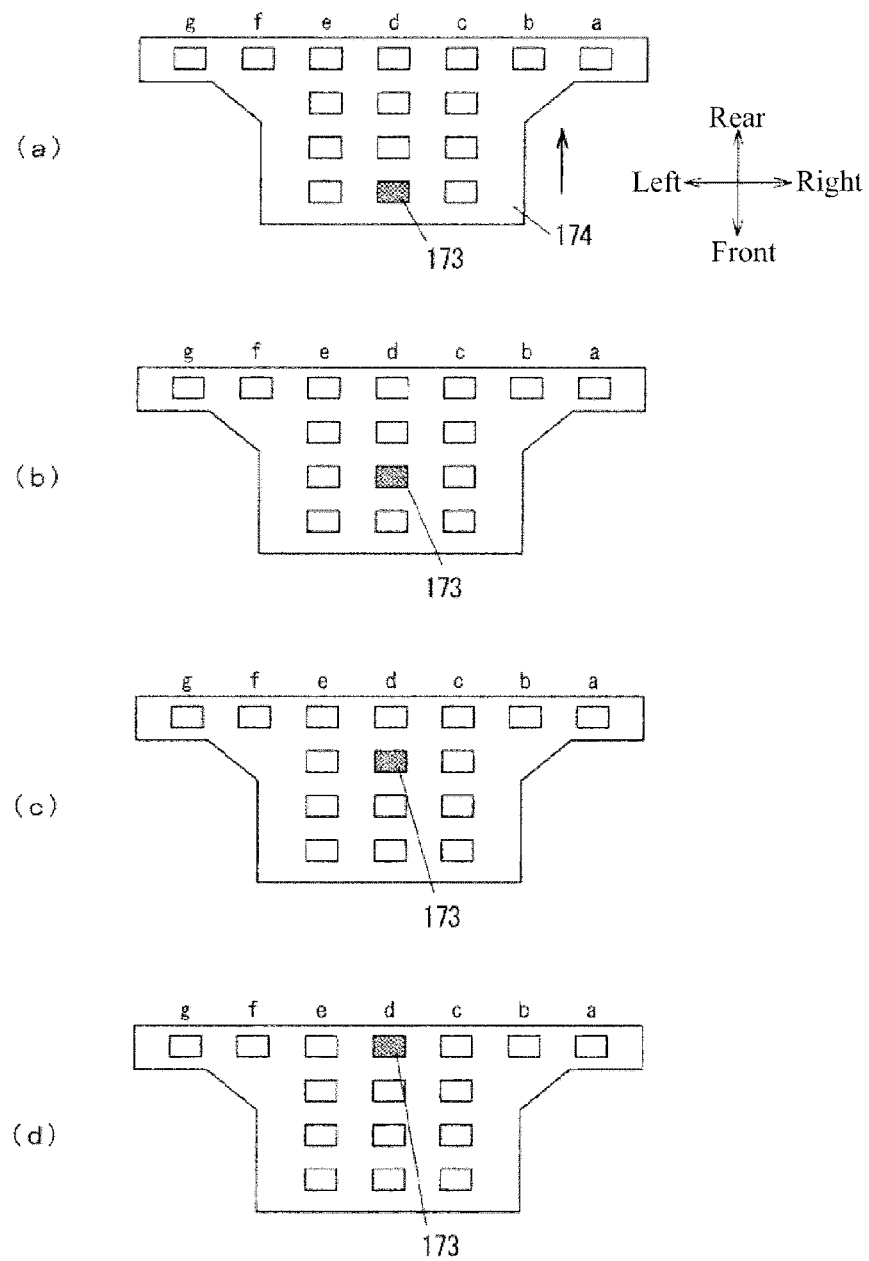

The light-emission pattern in which, only single light-emitting elements 173 and not the light-emitting elements 173 in a horizontal row glow in order from the frontward to the rearward as shown in FIG. 33, may be used (FIG. 33 is an example of the light-emitting elements 173 glowing rearward. The pattern is such that the state returns from the state in FIG. 33(d) to the state in FIG. 33(a)).

Although it is not limited, in a case in which the injection head is equipped with an auto-return function (a function by which, when a predetermined button is pressed, the ram member automatically returns to a predetermined retreat position), such light-emission pattern may be used for an auto-return operation.

In a case in which, each light-emitting portion 173 is an element capable of emitting light of plurality of colors, the color of light emitted may be let to be different according to a difference in the input operation of moving the ram member. For instance, light of a first color may be made to be emitted when the jog button is pressed, and light of a second color may be made to be emitted when the operating knob is turned. Or, the color of light emitted may be let to be different in the case of moving the ram member by an input by the operator, and in a case of automatic injection.

Figure 34:
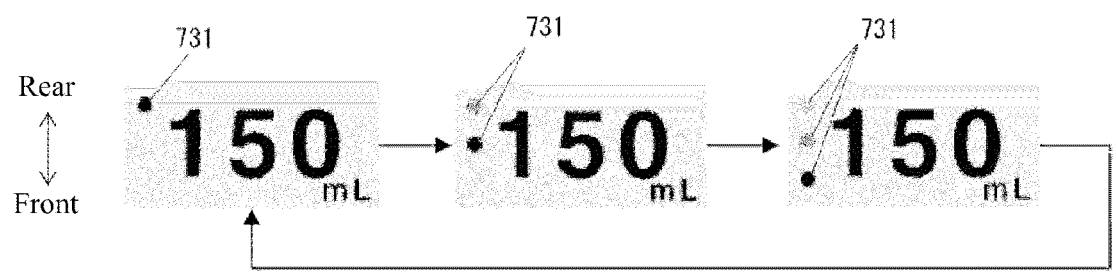
FIG. 34 is an example of information that can be displayed on a head-display portion (chemical-liquid injection)

While the chemical-liquid injection is carried out, the display on the display 146 of the injection head may be a display of the volume of a chemical liquid remained in the syringe. As a specific example, the remaining volume may be displayed as '150 mL' as in FIG. 34. It is preferable that the display is such that the remaining volume decreases gradually with the advance of the ram member. Although it is not limited, a plurality of indicators 731 in the form of round dots near the display of the remaining volume is displayed in FIG. 34. By displaying these indicators 731 in order from frontward toward rearward, it may be made favorably visible that the ram member is advancing.

Figure 35:
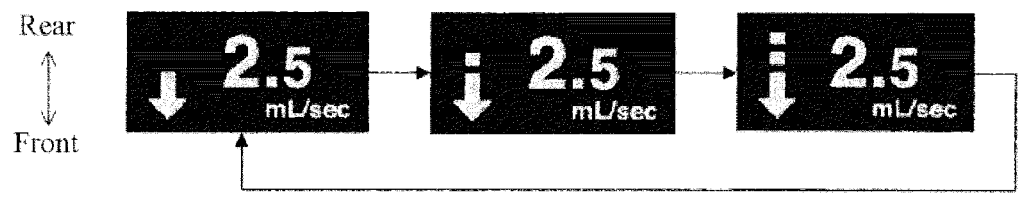
FIG. 35 is an example of information that can be displayed on the head-display portion (manual operation)

In a case of moving the ram member by the operating knob 171, at least one of a display of an arrow indicating the direction of advance of the ram member and a display of the injecting rate may appear as shown in FIG. 35.

In a case of operating the operating knob manually, the advance or the retreat is determined by the direction of rotation, and the injecting rate is determined by the speed or rotation. Therefore, such a display is preferable from a point that it is possible to verify visually, as to whether the ram member is advancing or retreating, and/or as to with what injecting rate the injection is being carried out.

Figure 36:
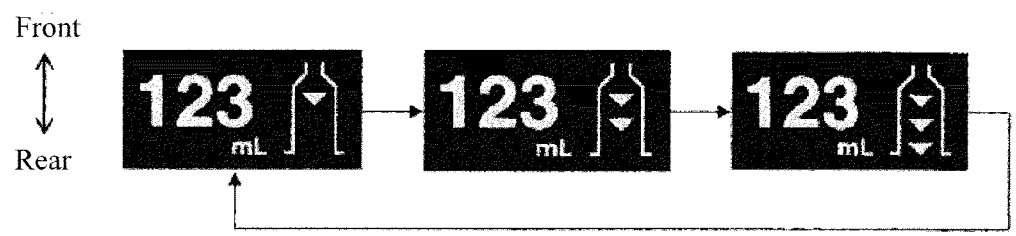
FIG. 36 is an example of information that can be displayed on the head-display portion (automatic retreat)

In a case of returning the ram member by the auto-return function, a display may be made such that one can make out that the piston member of the syringe has been pulled, as shown in FIG. 36.

(7-3. Details of Injecting Operation)

Figure 37:
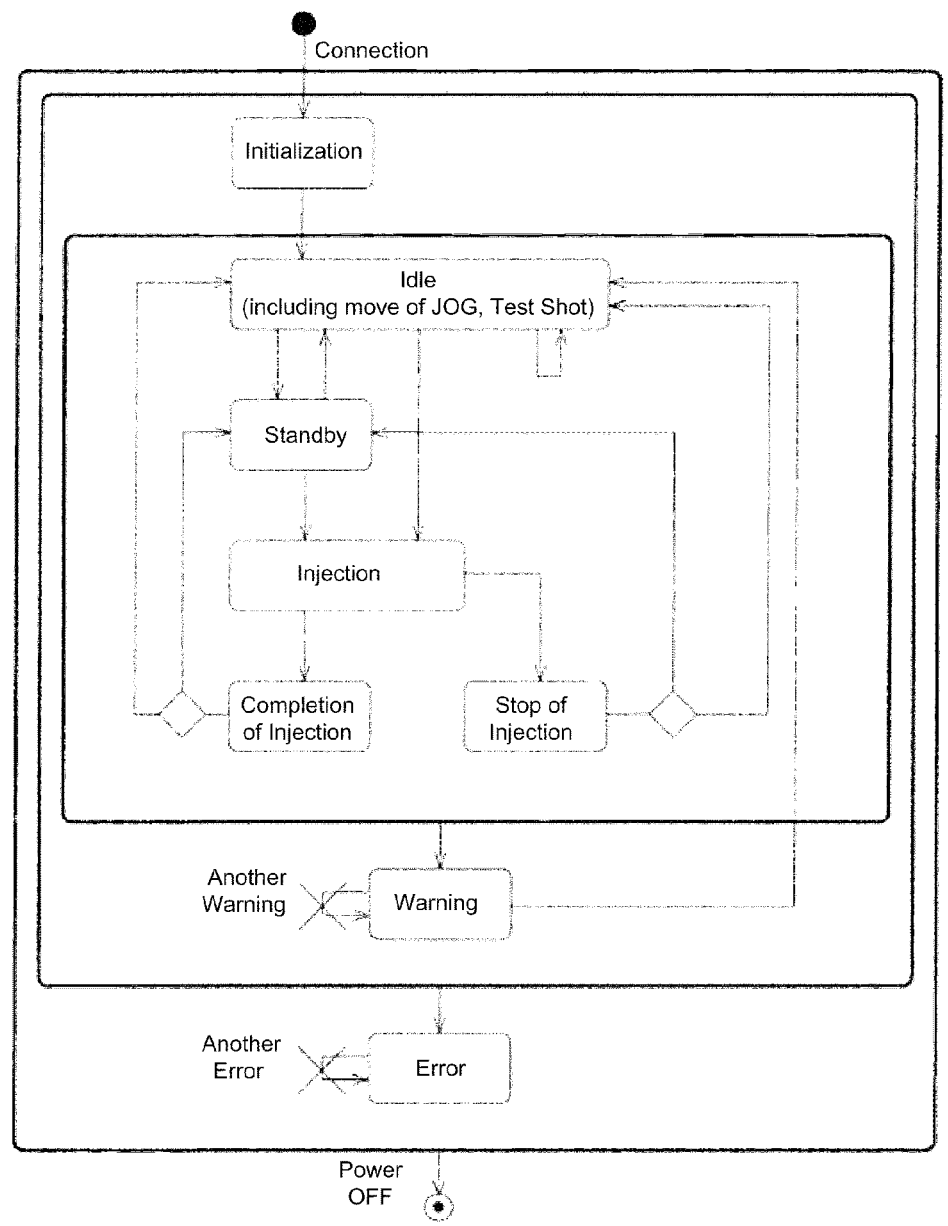
FIG. 37 is an example of a state transition diagram of an operation of the injection head.

FIG. 37 is an example of a state transition diagram of an operation of the injection head. After the electric power supply is put ON, a self-check is carried out as one of the initial operations. The self-check may be carried out for the main unit and/or for the overall system. In equipment having a control circuit, the self-check is executed according to the requirement.

At least one of the following information may be transmitted from the injection head to the console (and/or another unit) at a predetermined timing:
information related to software,
information of a size of a syringe loaded on the head,
information of remaining volume of a chemical liquid in the syringe,
result of the self-check, etc.

A detection of the size of the syringe is carried out by a sensor of the injection head. The sensor may detect the presence or absence of the protective case, and/or a type of the protective case. It may be distinguished as to whether the size of the syringe is a first size (100 ml for example), or a second size (150 ml for example). As a matter of course, the distinction may be made not only between two types but also among three or more types. By knowing the size of the syringe, the calculation of the moving speed of the ram member and the remaining volume according to that size can be carried out accurately.

(Clamper)

In the chemical-liquid injector of the present invention, a state of the syringe clamper may be monitored. When the syringe clamper is closed, or opened, or at a timing of both of the two, the injection head may notify (inform) the closing or opening to the console side.

(Rate, Remaining Volume)

The injection head may measure the injecting rate during the jog movement or automatic injection.

1) The apparatus may measure all the time, the remaining volume of a chemical, and whenever there is a change in the remaining volume, it may be notified from the injection head to the console. Moreover, the notification may be made at a predetermined interval.

2) When the syringe protective case has been installed or not installed, the new remaining volume may be notified to the console.

3) When the ram member is at the most advanced position, the remaining volume may be set to zero.

4) When the ram member reaches the most retreated position and stops, the remaining volume may be reset.

5) The injection pressure of a chemical liquid may be calculated by using a sensor signal of the motor current (for example).

Figure 38:
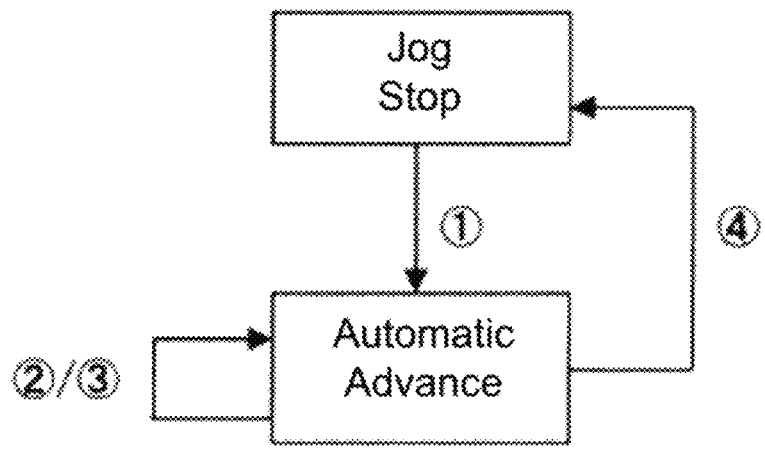
FIG. 38 is a state transition diagram related to an automatic advance.

FIG. 38 is a state transition diagram related to an automatic advance Circled numbers (in the diagram) correspond to numbers shown in half parentheses in the following description.

1) The ram member may advance automatically in a case in which all or some of predetermined conditions mentioned below are fulfilled in a state of the jog stopped:
a presser is at the most retreated position (retreat limit sensor is ON)
the syringe clamper is closed in a state of the syringe protective case installed
the head button has not been pressed
an angio (angiography) hand-switch has not been pressed
the stop-button of the console has not been pressed
a predetermined time has elapsed in a state of the syringe clamper closed an automatic-advance function is in a valid state (set on the console side for example).

2), 3) In a case in which the pressure has reached a limit value, or in a case in which the accelerator button on the head is pressed, rate limiting or acceleration is carried out accordingly.

4) The ram member may stop when any one of the following conditions is fulfilled during the automatic advance:
press the head button other than accelerator button
press the accelerator button twice or more than twice
press the angio hand-switch
press the stop button of the console
presser reaches the most advanced position (advance limit sensor ON)
install or remove the syringe protective case
open or close the syringe clamper.

Figure 39:
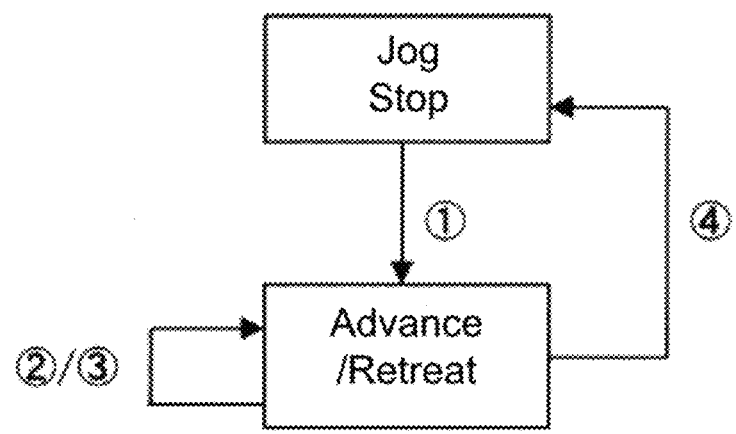
FIG. 39 is a state transition diagram related to an advance and a retreat.

FIG. 39 is a state transition diagram related to the advance/retreat by the operating knob. Circled numbers in the diagram correspond to numbers in half parentheses in the following description.

1) The ram member may move in a case in which all or some of predetermined conditions mentioned below are fulfilled when the operating knob is rotated in a state of the jog stopped.

the ram member is not at the most advanced position (at the time of moving in a direction of advance)
the ram member is not at the most retreated position (at the time of moving in a direction of retreat)
the syringe protective case is installed and the syringe clamper is closed (at the time of advance)
the head button and switches are not pressed
the rotation operation is not excessively slow.

2), 3)

In accordance with the speed of rotation of the operating knob, a speed of the presser is variable in a range of 0.1 to 2.0 (mL/sec) (for example).

As the pressure reaches or exceeds a limit value, a rise in the pressure is to be suppressed by controlling the speed.

4) The ram member may stop when any of the following conditions is fulfilled during the rotation operation of the operating knob:

stop operating the manual knob
press the head button
press the angio hand-switch
press the stop button of the console
the ram member reaches the most advanced position (at the time of moving in the direction of advance)
the ram member reaches the most retreated position (at the time of moving in the direction of retreat)
mount or remove the syringe protective case
open or close the syringe clamper
an amount of continuous movement from the start-position becomes a predetermined amount or more (such as 10 (mL)).

(Standby)

A 'standby', in this example, is basically, one of conditions for the start of injection. The standby state may be assumed when all or some of predetermined conditions mentioned below are fulfilled, and an operation of standby is carried out by the operator:

the syringe protective case is mounted
the syringe clamper is closed
a state of jog stop
the button of head is not pressed
the injection protocol is set at the console side, or the remaining volume is adequate
the angio hand-switch has not been pressed.

(Chemical-Liquid Injection)

For injecting a chemical liquid, it is necessary that a syringe loading portion of the injection head is in a state of being directed downward. In the standby state, when a predetermined button (such as the hand switch) is pressed, the injection is executed.

In an injecting phase, a chemical liquid is to be injected at a predetermined rate set in advance. All or some of predetermined controls mentioned below are carried out:

In a case in which a rise-time has been set, the injecting rate is increased (release brake) from the lowest rate up to the set-rate over a time set.
Periodically notify the injecting rate and/or pressure of the head to the console side.

When a volume that has been set is injected, the injection is completed. After the completion, all or some of the controls mentioned below are carried out:

1) As the execution of the injection protocol is completed, the injection is completed. Completion of injection is notified together with the injection result, to the console side.

Although the brake is released after the completion of injection, when it is valid in the setting on the console side, the brake is applied for a predetermined time.

2) When all or some of the conditions mentioned below are fulfilled, a transition from a state of injection completed to a state of jog-stop takes place.

release (take a finger off) the angio hand-switch (at the time of start by the hand switch),
a predetermined operation from the console
elapsing of time by a timer.

(7-4. Operation Control after Completion of Injection)

Incidentally, in a case of an injection for the angiography examination as in the present embodiment, a chemical liquid being injected through a catheter, the injection pressure of the chemical liquid becomes high. Moreover, after the chemical liquid has been injected, in a case in which the ram member of the piston-driving mechanism is supposedly let to be at that position as it has been, after the catheter is removed from the patient (or as a predetermined connector of a chemical-liquid circuit is removed), due to a residual pressure, there is a possibility that the chemical liquid is dripped from the catheter.

It is heretofore known that for releasing the residual pressure, a control to make the ram member retreat slightly is carried out after the chemical-liquid injection has been completed.

Figure 40:
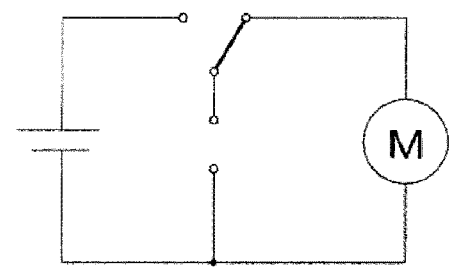
FIG. 40 is a schematic diagram of a circuit for explaining an electric brake of a motor.

On the other hand, in an arrangement in which without applying a mechanical brake, and by letting terminals of the motor to be open as shown in FIG. 40, the motor being rotatable with a comparatively lighter force, there is a possibility that the ram member retreats due to the residual pressure, according to the circumstances.

Therefore, according to one aspect of the present invention, the dynamic brake (electrical brake) is to be used as a braking means. In other words, a motor-driving circuit according to one aspect of the present invention may be capable of letting the motor to be in a short-circuit state by switching a switch C1 as shown schematically in FIG. 41(*a*). The switch C1 is not limited in particular, and may include a relay.

Figure 41:
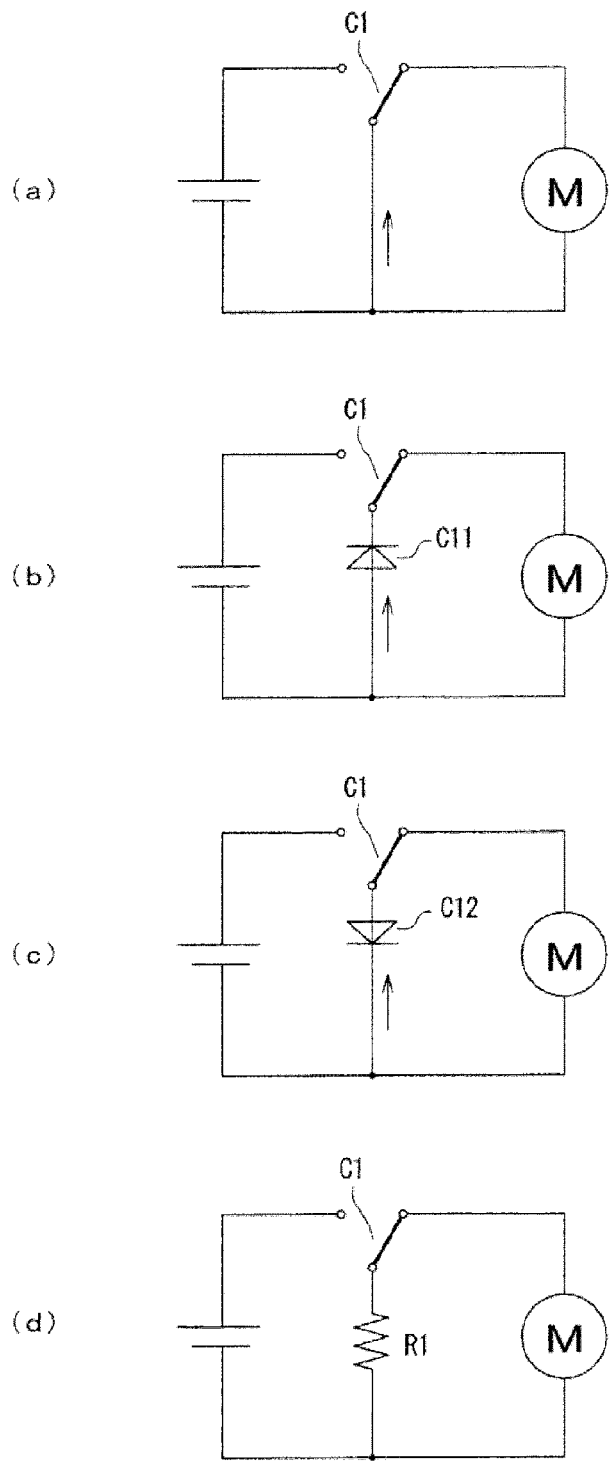
FIG. 41 is a diagram showing schematically a number of examples of a state of a circuit of a brake.

Moreover, as shown in FIGS. 41(*b*) and (*c*), by switching the switch C1, the motor may be connected to a diode C11. FIG. 41(*b*) shows a connection in a forward direction, and FIG. 41(*c*) shows a connection in a reverse direction. Moreover, in order to achieve a predetermined braking force, a circuit provided with a resistance R1 as in FIG. 41(*d*) may be used.

The motor-driving circuit may include only one of circuits shown in FIG. 41(*a*) to (*d*), or may be provided with a plurality or all of the circuits in FIG. 41(*a*) to (*d*). The motor-driving circuit may be switched automatically to any one of (or any two of) connecting states of a 'short-circuit', a 'forward connection', and a 'reverse connection'. Furthermore, the open state shown in FIG. 40 may also be selected.

A braking effect by the electrical brake is in order of 'short-circuit'>'forward connection'>'reverse connection'. It is preferable that a type of chemical liquid to be used, a thickness of the catheter, a thickness of the chemical-liquid tube, and a size of the syringe can be selected appropriately. Moreover, it is preferable that these can be selected appropriately according to a desire of the medical staff. Specifically, the chemical-liquid injector has a predetermined graphical user interface, and the selection of the type of the dynamic brake may be possible via a setting screen thereof.

Figure 42:
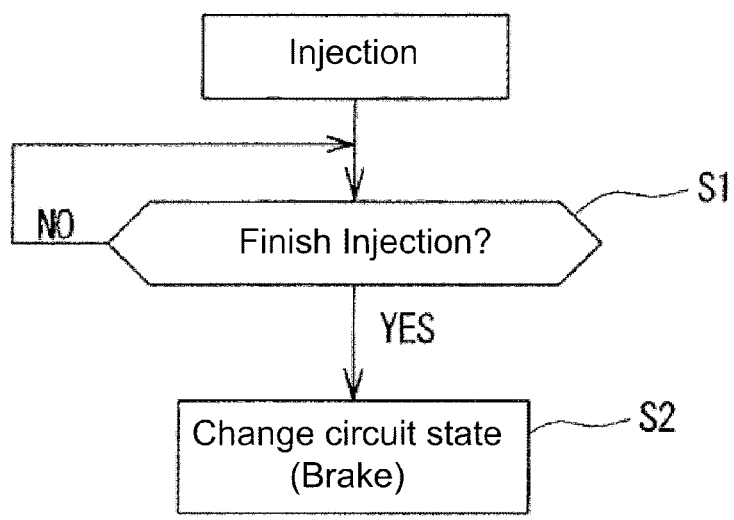
FIG. 42 is a diagram showing an example of an operation flow related to a change in the state of the circuit of the brake.

In the chemical-liquid injector which has been set as mentioned above, as shown in FIG. 42, after the injecting operation, a judgment of whether or not the injection is completed is made at step S1, and when a judgment of injection completed is made, the process advances to step S2, and changes to a circuit state of the dynamic brake. A flowchart in FIG. 42 is shown briefly, and a step of making a judgment of whether or not a predetermined time has elapsed may be inserted after step S1.

Regarding as to which circuit state is to be used, a predetermined circuit step has been set in advance, and other than an arrangement such that the chemical-liquid injector automatically switches to that circuit step at a predetermined time, the following arrangement may be made. In other words, the circuit state to be used is selected appropriately on the basis of information (may be a set value, an actually measured value, or the both) of the injection pressure immediately before the chemical-liquid injection. Specifically, in a case in which the injection pressure is high, a circuit state with a strong braking effect may be selected, and in a case in which the injection pressure is low, a circuit state with a weak braking effect may be used. As a matter of course, a degree of strong and weak of the injection pressure has been divided into three or more levels, and the circuit state associated with the respective level may be selected automatically in advance.

According to the arrangement of using the abovementioned electric brake, even in a state in which the residual pressure of a chemical liquid in the syringe is high after injecting the chemical liquid, since the braking effect is generated in the motor, it is possible to prevent the ram member from retreating energetically (as a result of this, the piston member of the syringe is also drawn with the ram member). The control may be executed to draw the ram member actively, and according to such arrangement, since it is possible to achieve the braking effect by a comparatively simple control of only changing the circuit condition, there is a merit that the control does not become complicated.

In FIG. 41 described above, although the circuit state was depicted briefly, as a matter of course, the specific arrangement can be changed appropriately provided that it is possible to realize the abovementioned technical idea. A plurality of diodes disposed in parallel may be used, and even regarding the relay, as a matter of course, a plurality of relays may be used.

In the description above, the following invention is disclosed:

1. A system including,
   a piston-driving mechanism which includes a ram member that makes a piston (plunger) of a syringe move back and forth, and a motor which is a drive source, and
   a motor-driving circuit, wherein
   the motor-driving circuit is provided to be capable of forming at least two types of electrical-brake circuit states.
2. The electrical-brake circuit states are switchable.
3. The system includes a graphical user interface for selecting the electrical-brake circuit state that is to be used.
4. It is possible to select two types of electrical-brake circuit states, three types of electrical-brake circuit states, or four types of electrical-brake circuit states.
5. After injecting the chemical liquid, the electrical-brake circuit is automatically switched to the predetermined electrical-brake circuit.

The system includes the relay for switching the circuit state.

(7-5. Structure to Prevent Protective Cover from Coming Off)

In the abovementioned embodiment, the chemical-liquid injector in a state of the protective cover put on the syringe had a structure of the injection head supported by the clamper (diagrams such as FIG. 1A, FIG. 1B, and FIG. 3).

In a case of a type of using after sucking a chemical liquid into the syringe, first of all, suction of the chemical liquid into the syringe becomes necessary. This suction operation, in general, is carried out in a posture in which the distal-end portion of the syringe is directed upward.

In a case in which, when the syringe is directed upward in such manner, in a state of the clamper member 145-1 not closed firmly, there is a possibility that the syringe with the protective cover comes off the clamper, and in some cases, falls.

Figure 43:
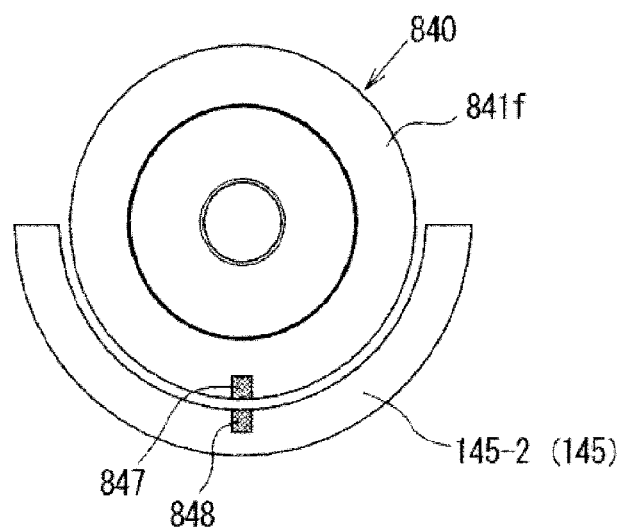
FIG. 43 is a diagram showing an example of a structure for preventing the protective cover from coming off.

Therefore, according to an aspect of the present invention, a mechanism to prevent coming-off as described below may have been provided. In other words, a first magnet 847 may have been provided to a portion of the protective case 840 as shown in FIG. 43. The magnet 847 may be attracted directly to the clamper member 145-2 which is a magnetic body (such as iron).

Or, a second magnet 848 may have been provided to a clamper side, and the first magnet 847 and the second magnet 848 may be attracted mutually. As another aspect, a magnetic body (a member other than the clamper member, such as a screw and a pin) which the first magnet 847 attracts may be provided instead.

A person skilled in the art, from the abovementioned description, would easily understand that a magnet may be provided only on the clamper side, and a magnetic body may be provided on the protective-cover side.

Regarding the first magnet 847, there may be only one, or may have been disposed in plurality. For instance, two or more than two or three magnets 847 may have been disposed in a peripheral direction of the flange portion 840*f* of the protective case 840, leaving a distance mutually.

As a more specific example, as shown in FIG. 43, in a case in which a projecting portion 841*p* has been formed on a portion of the flange portion 841*f* of the protective case 840, a magnet 847 may be disposed on both sides of the projecting portion 841*p*.

The projecting portion 841*p* may be set into a recess or a through hole provided on the clamper-member side. The projecting portion 841*p* is provided with one or a plurality of identification means (such as a magnetic body that is detected by a hall sensor) for identifying the protective cover.

In this case, the second magnets 848 may be disposed at respective positions (the clamper side) facing the first magnets 847.

Although it is not limited, a range of the flange portion 841*f* in which the magnets are provided, may be a within a circular-arc range having a central angle not more than 60°.

Figure 44:
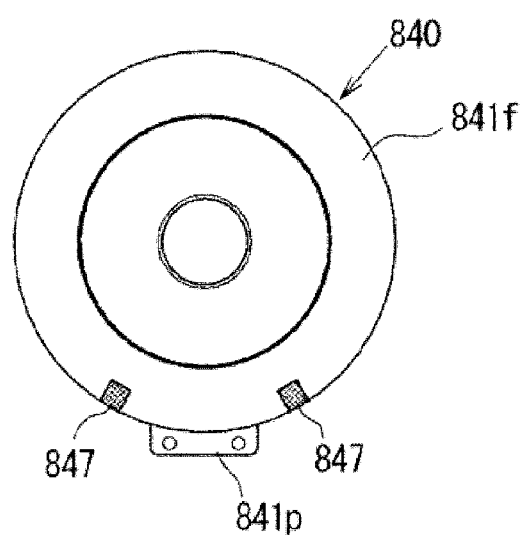
FIG. 44 is a diagram showing an example of another structure for preventing the protective cover from coming off.

The description made below is common for arrangements in FIG. 43 and FIG. 44. Regarding the first magnet, it is preferable that the magnet to be disposed has a structure such that a contour shape of the flange portion 841*f* does not protrude. For instance, a hole extended in a substantially radial direction may be formed in the flange portion 841*f*, and the magnet may be disposed in the hole. A similar structure may be adopted for the second magnet.

The magnets are not limited to be quadrangular column or cylindrical column shaped magnets, and may be magnetized screws. Moreover, an arrangement may be such that one or a plurality of magnets on the protective-cover side is attracted to one or a plurality of screws provided on the clamper side. It is preferable that the respective magnets and screws have a positional relationship of being disposed face-to-face.

According to the arrangement described above, when the syringe having the protective cover put thereon is set in the clamper member 145-2 (FIG. 1A), by a first magnetic attraction member (in some cases, may be a member such as an iron member) on the protective-cover side and a second magnetic attraction member (in some cases, may be a member such as an iron member) on the clamper side, the protective cover is held by magnetic attraction. Accordingly, even in a case in which the injection head is supposedly let to be in a suction posture without closing the clamper member 145-1 on the upper side, it is possible to prevent the protective case and the clamper from coming-off or falling.

A position for disposing the magnet may be let to be a portion of the protective cover, other than the flange portion. Moreover, regarding the injection head, a position for disposing the magnet may be let to be a portion of the injection head (on the head housing, at a portion near the protective cover) other than the clamper.

(Note)

The present application discloses at least the following invention. The present invention should not be construed as being limited by numbers in parentheses.

1. A chemical-liquid injector including,
    a piston-driving mechanism (130) that moves a piston member of a syringe containing a contrast medium which includes an actuator and a ram member which is moved back and forth by the actuator,
    a control circuit (150) which is electrically connected to the actuator, and
    an operating knob unit (170) which includes an operating knob that is to be operated by an operator, and a rotation sensor that outputs an electric signal in corresponding to a rotation of the operating knob, wherein the control circuit operates the piston-driving mechanism accordingly, on the basis of a signal from the rotation sensor.
2. The chemical-liquid injector described above, wherein the control circuit
    makes the ram member advance when the operating knob is turned in a first direction, and
    makes the ram member retreat when the operating knob is turned in a second direction.
3. The chemical-liquid injector described above, further including,
    a position sensor which detects a position of the ram member.
4. The chemical-liquid injector described above, wherein the control circuit makes a judgment of a position of the ram member on the basis of a result of the position sensor, and operates the piston-driving mechanism in accordance with the operation of the operating knob only when the ram member is in a predetermined movable range.
5. The chemical-liquid injector described above wherein the control circuit
    moves the ram member only through a predetermined moving distance corresponding to an amount of rotation of the operating knob, and
    changes the moving distance of the rain member corresponding to the amount of rotation of the operating knob when an input for switching has been received from the user.
6. The chemical-liquid injector described above, further including,
    a light-emitting device which is electrically connected to the control circuit, wherein
    the control circuit makes the light-emitting device emit light at least in one of a case in which the rain member of the piston-driving mechanism is made to advance and a case in which the ram member of the piston-driving mechanism is made to retreat.
7. The chemical-liquid injector described above, wherein a torque for rotating the operating knob is not lower than 0.2 Kgf·cm.
8. The chemical-liquid injector described above for angiography examination, wherein an output torque of the actuator is not lower than 70 W.
9. The chemical-liquid injector described above, including,
    an injection head which includes a syringe holding portion that holds the syringe, and the piston-driving mechanism, and
    a console which includes a display, and is connected to the injection head by wire or by wireless.
10. The chemical-liquid injector describe above, wherein the injection head includes an organic EL display (OLED: organic light-emitting diode).
11. The chemical-liquid injector described above, wherein a heater is provided to the syringe holding portion, and the heater is in the form of a transparent sheet.
12. An operation control method which is a method for controlling an apparatus including a piston-driving mechanism (130) that moves a piston member of a syringe containing a contrast medium which includes an actuator and a ram member which is moved back and forth by the actuator, a control circuit (150) which is electrically connected to the actuator, and an operating knob unit (170) which includes the operating knob that is to be operated by the operator, and a rotation sensor that outputs an electric signal in accordance with a rotation of the operating knob, including
    a step of operating the piston-driving mechanism in which, the control circuit operates the piston-driving mechanism accordingly, on the basis of a signal from the rotation sensor.
13. The method describe above, further including,
    a step in which, the control circuit makes the ram member advance when the operating knob is turned in the first direction, and makes the ram member retreat when the operating knob is turned in the second direction.
14. The method described above, further including,
    a step in which the control circuit makes the judgment of a position of the ream member on the basis of a result of the position sensor that detects the position of the ram member, and
    a step of operating the piston-driving mechanism in accordance with an operation of the operating knob only when the ram member is in the predetermined movable range.
15. The method described above in which the control circuit moves the ram member only through a predetermined moving distance corresponding to the amount of rotation of the operating knob, further including comprising,
    a step of changing the moving distance of the ram member corresponding to the amount of rotation of the operating knob when an input for switching has been received.

16. The method described above for controlling an apparatus further including the light-emitting device which is electrically connected to the control circuit, further including, a step of making the light-emitting device emit light in which, the control circuit makes the light-emitting emit light at least in one of a case in which the ram member of the piston-driving mechanism is made to advance and a case in which the rain member of the piston-driving mechanism is made to retreat.

DESCRIPTION OF REFERENCE NUMERALS 100 chemical-liquid injector
110 injection head
111 housing
130 piston-driving mechanism
131 ram member
132 ball nut unit
135 ball screw
137 transmission mechanism
139 motor
139s rotation sensor
140 syringe holding portion
141 protective case receiver
141a heater
141b holding member
141c thermistor
141d light-emitting device
145 clamper
145-1, 145-2 clamper member
146 display
150 control circuit
161 physical button
161-1 key
161-2 switch (first detector)
161-3 switch (second detector)
162 position sensor
163 clamper sensor
164 syringe sensor
165 pressure sensor
168 storage section
169 interface
173 emitting portion
173a cover
173b indicator
190 power-supply unit
210 console
250 control section
251 display
253 touch panel
257 slot
258 foot switch
261 storage section
262 communication section
269 interface
300 (300-1, 300-2) imaging apparatus
800 syringe
810 cylinder member
811a nozzle portion
811f flange portion
814 engaging protrusion
820 piston member (plunger)
840 protective case
841 main-body member
841h opening portion
841f flange portion
847 magnet
848 magnet or magnetic material
P102 arm member
P105 connecting member
P115 support shaft
P115a round shaft
P121, P121' collar
P123 plate spring
P125 nut
P129-1, 129-2 sliding member
Ps1 fixing screw

The invention claimed is:

1. A chemical-liquid injector, comprising:
a piston-driving mechanism that moves a piston member of a syringe containing a contrast medium, the piston-driving mechanism including an actuator and a ram member which is moved back and forth by the actuator;
a control circuit which is electrically connected to the actuator; and
an operating knob unit which includes an operating knob that is to be operated by an operator, and a rotation sensor that outputs an electrical signal corresponding to a rotation of the operating knob, and
a light-emitting device that is electrically connected to the control circuit,
wherein the control circuit is configured to operate the piston-driving mechanism on the basis of the signal from the rotation sensor, and to make the light-emitting device emit light when the ram member of the piston-driving mechanism is made to advance and when the ram member of the piston-driving mechanism is made to retreat, and
wherein the control circuit is configured so as not to operate the actuator and not to make the light emitting device to emit light even if the operating knob is rotated when the movement of the ram member is inhibited.

2. The chemical-liquid injector according to claim 1, wherein the control circuit is configured to make the ram member advance when the operating knob is turned in a first direction, and make the ram member retreat when the operating knob is turned in a second direction.

3. The chemical-liquid injector according to claim 1, further comprising a position sensor which detects a position of the ram member.

4. The chemical-liquid injector according to claim 3, wherein the control circuit is configured to make a judgment of a position of the ram member on the basis of a result of the position sensor, and to operate the piston-driving mechanism in accordance with the operation of the operating knob only when the ram member is within a predetermined movable range.

5. The chemical-liquid injector according to claim 1, wherein the control circuit is configured to move the ram member only through a predetermined moving distance corresponding to an amount of rotation of the operating knob, and to change the moving distance of the ram member corresponding to the amount of rotation of the operating knob when an input for change has been received from a user.

6. The chemical-liquid injector according to claim 1, wherein a torque for turning the operating knob is not lower than 0.2 Kgf·cm.

7. The chemical-liquid injector according to claim 1, designed for angiography diagnosis, wherein an output torque of the actuator is not lower than 70 W.

8. The chemical-liquid injector according to claim 1, comprising:
- an injection head which includes a syringe holding portion that holds a syringe, and the piston-driving mechanism; and
- a console which includes a display, and is connected to the injection head by wire or by wireless.

9. The chemical-liquid injector according to claim 8, wherein the injection head includes an organic EL display (OLED: organic light-emitting diode).

10. The chemical-liquid injector according to claim 8, wherein a heater is provided to the syringe holding portion, and the heater is in the form of a transparent sheet.

11. An operation control method for controlling the chemical-liquid injector of claim 1 comprising:
- moving the piston-driving mechanism on the basis of an electrical signal from the rotation sensor, and
- making the light-emitting device emit light,
- wherein the control circuit makes the light-emitting device emit light when the ram member of the piston-driving mechanism is made to advance and when the ram member of the piston-driving mechanism is made to retreat,
- wherein the control circuit does not operate the actuator and does not make the light emitting device emit light even if the operating knob is rotated when the movement of the ram member is inhibited.

12. The method according to claim 11, further comprising: a step in which, the control circuit makes the ram member advance when the operating knob is turned in a first direction, and makes a ram member retreat when the operating knob is turned in a second direction.

13. The method according to claim 11, further comprising:
- a step in which the control circuit makes a judgment of a position of the ram member on the basis of a result of a position sensor that detects the position of the ram member; and
- a step of operating the piston-driving mechanism in accordance with an operation of the operating knob only when the ram member is within a predetermined movable range.

14. The method according to claim 11, wherein the control circuit moves the ram member only through a predetermined moving distance corresponding to the amount of rotation of the operating knob, and further comprising a step of changing the moving distance of the ram member corresponding to the amount of rotation of the operating knob when an input for changing has been received.

\* \* \* \* \*